(12) United States Patent
Campbell et al.

(10) Patent No.: US 10,179,033 B2
(45) Date of Patent: Jan. 15, 2019

(54) MAGNETIC-ANCHORED ROBOTIC SYSTEM

(71) Applicant: Bio-Medical Engineering (HK) Limited, Hong Kong SAR (CN)

(72) Inventors: Archibald MacRobert Campbell, Cambridge (GB); David Anthony Cardwell, St. Ives (GB); John Hay Durrell, Cambridge (GB); Yuanhua Shi, Cambridge (GB); Kai Yuan Huang, Cambridge (GB); Kysen Grant Boyd Palmer, Cambridge (GB); Anthony Robert Dennis, Hitchin (GB); Chung Kwong Yeung, Hong Kong (CN)

(73) Assignee: Bio-Medical Engineering (HK) Limited, Hong Kong SAR (CN)

( * ) Notice: Subject to any disclaimer, the term of this patent is extended or adjusted under 35 U.S.C. 154(b) by 565 days.

(21) Appl. No.: 14/927,048

(22) Filed: Oct. 29, 2015

(65) Prior Publication Data
US 2016/0045273 A1    Feb. 18, 2016

Related U.S. Application Data

(63) Continuation-in-part of application No. 13/871,915, filed on Apr. 26, 2013, now Pat. No. 10,065,323.
(Continued)

(51) Int. Cl.
*A61B 34/00*    (2016.01)
*A61B 19/00*    (2006.01)
(Continued)

(52) U.S. Cl.
CPC ........ *A61B 34/73* (2016.02); *A61B 17/00234* (2013.01); *A61B 17/3417* (2013.01);
(Continued)

(58) Field of Classification Search
CPC ... A61B 2034/302; A61B 34/73; A61B 34/76; A61B 17/3417
See application file for complete search history.

(56) References Cited

U.S. PATENT DOCUMENTS

| 4,278,077 A | 7/1981 | Mizumoto |
|---|---|---|
| 4,289,288 A | 9/1981 | Gransberry et al. |

(Continued)

FOREIGN PATENT DOCUMENTS

| CN | 101091665 | 12/2007 |
|---|---|---|
| JP | 2004-321692 | 11/2004 |

(Continued)

OTHER PUBLICATIONS

International Search Report and Written Opinion, PCT/CN2013/000478, dated Jul. 25, 2013, 9 pages.
(Continued)

*Primary Examiner* — Andrew Yang
(74) *Attorney, Agent, or Firm* — Baker & McKenzie LLP

(57) ABSTRACT

Present example embodiments relate generally to a surgical system comprising an internal anchor assembly configurable to be inserted into and positioned inside a cavity of a body. The surgical system further comprises an external anchor assembly configurable to magnetically couple to the internal anchor assembly. The external anchor assembly may comprise a magnetic assembly. The magnetic assembly may include one or more superconducting magnets configurable to generate a magnetic field. The magnetic assembly may further include a conductive housing for receiving the one or more superconducting magnets. The external anchor assembly may further include a temperature control section configurable to control a temperature of the one or more superconducting magnets via the conductive housing. The external anchor assembly may further include an external anchor body configurable to receive the magnetic assembly
(Continued)

and the temperature control section. The external anchor body may be fixably positionable outside of the body.

36 Claims, 37 Drawing Sheets

Related U.S. Application Data

(60) Provisional application No. 61/718,252, filed on Oct. 25, 2012, provisional application No. 61/638,828, filed on Apr. 26, 2012.

(51) Int. Cl.
*A61B 17/34* (2006.01)
*A61B 17/00* (2006.01)
*A61B 34/30* (2016.01)
*A61B 90/00* (2016.01)

(52) U.S. Cl.
CPC .......... *A61B 19/20* (2013.01); *A61B 19/2203* (2013.01); *A61B 34/30* (2016.02); *A61B 34/76* (2016.02); *A61B 17/3423* (2013.01); *A61B 2017/00283* (2013.01); *A61B 2017/00411* (2013.01); *A61B 2017/00876* (2013.01); *A61B 2017/3484* (2013.01); *A61B 2019/2215* (2013.01); *A61B 2019/2253* (2013.01); *A61B 2019/2292* (2013.01); *A61B 2019/5227* (2013.01); *A61B 2034/302* (2016.02); *A61B 2090/371* (2016.02); *Y10S 901/09* (2013.01); *Y10S 901/34* (2013.01); *Y10S 901/41* (2013.01); *Y10T 428/13* (2015.01)

(56) References Cited

U.S. PATENT DOCUMENTS

| | | | |
|---|---|---|---|
| 5,566,268 A | 10/1996 | Radliff et al. |
| 5,604,531 A | 2/1997 | Iddan et al. |
| 5,675,124 A | 10/1997 | Stough et al. |
| 5,696,837 A | 12/1997 | Green |
| 6,078,718 A | 6/2000 | Merriken et al. |
| 6,133,528 A | 10/2000 | Henriott et al. |
| 6,240,312 B1 | 5/2001 | Alfano et al. |
| 6,402,686 B1 | 6/2002 | Ouchi |
| 6,442,435 B2 | 8/2002 | King et al. |
| 6,648,814 B2 | 11/2003 | Kim et al. |
| 6,676,684 B1 | 1/2004 | Morley et al. |
| 6,702,734 B2 | 3/2004 | Kim et al. |
| 6,719,684 B2 | 4/2004 | Kim et al. |
| 6,729,587 B1 | 5/2004 | White |
| 6,776,165 B2 | 8/2004 | Jin |
| 6,936,003 B2 | 8/2005 | Iddan |
| 6,984,205 B2 | 1/2006 | Gazdinski |
| 6,991,627 B2 | 1/2006 | Madhani et al. |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,111,769 B2 | 9/2006 | Wales et al. |
| 7,126,303 B2 | 10/2006 | Farritor et al. |
| 7,169,104 B2 | 1/2007 | Ueda et al. |
| 7,182,089 B2 | 2/2007 | Ries |
| 7,199,545 B2 | 4/2007 | Oleynikov et al. |
| 7,311,107 B2 | 12/2007 | Harel et al. |
| 7,339,341 B2 | 3/2008 | Oleynikov et al. |
| 7,429,259 B2 | 9/2008 | Cadeddu et al. |
| 7,492,116 B2 | 2/2009 | Oleynikov et al. |
| 7,625,338 B2 | 12/2009 | Gilad et al. |
| 7,691,103 B2 | 4/2010 | Fernandez et al. |
| 8,145,295 B2 | 3/2012 | Boyden et al. |
| 8,202,265 B2 | 6/2012 | Boulais |
| 8,343,171 B2 | 1/2013 | Farritor et al. |
| 8,579,957 B2 | 11/2013 | Linder et al. |
| 8,891,924 B2 | 11/2014 | Yeung et al. |
| 9,020,640 B2 | 4/2015 | Yeung et al. |
| 2002/0103417 A1 | 8/2002 | Gazdzinski |
| 2003/0020810 A1 | 1/2003 | Takizawa et al. |
| 2003/0074075 A1 | 4/2003 | Thomas, Jr. et al. |
| 2003/0092964 A1 | 5/2003 | Kim et al. |
| 2003/0114731 A1 | 6/2003 | Cadeddu et al. |
| 2003/0167000 A1 | 9/2003 | Mullick et al. |
| 2004/0050395 A1 | 3/2004 | Ueda et al. |
| 2004/0086238 A1 | 5/2004 | Finona et al. |
| 2004/0176664 A1 | 9/2004 | Iddan |
| 2004/0256138 A1 | 12/2004 | Grubish et al. |
| 2005/0029978 A1 | 2/2005 | Oleynikov |
| 2005/0096502 A1 | 5/2005 | Khalili |
| 2005/0165449 A1 | 7/2005 | Cadeddu et al. |
| 2005/0273139 A1 | 12/2005 | Krauss et al. |
| 2005/0288555 A1 | 12/2005 | Binmoeller |
| 2006/0009785 A1 | 1/2006 | Maitland et al. |
| 2006/0079897 A1 | 4/2006 | Harrison et al. |
| 2006/0119304 A1 | 6/2006 | Farritor et al. |
| 2006/0149135 A1 | 7/2006 | Paz |
| 2006/0153516 A1 | 7/2006 | Napiorkowski et al. |
| 2006/0190034 A1 | 8/2006 | Nishizawa et al. |
| 2006/0196301 A1 | 9/2006 | Oleynikov et al. |
| 2006/0198619 A1 | 9/2006 | Oleynikov et al. |
| 2007/0032701 A1 | 2/2007 | Fowler |
| 2007/0080658 A1 | 4/2007 | Farritor et al. |
| 2007/0123748 A1 | 5/2007 | Meglan |
| 2007/0157937 A1 | 7/2007 | Mikkaichi et al. |
| 2007/0161855 A1 | 7/2007 | Mikkaichi et al. |
| 2007/0241714 A1 | 10/2007 | Oleynikov et al. |
| 2007/0255273 A1 | 11/2007 | Fernandez et al. |
| 2008/0004634 A1 | 1/2008 | Farritor et al. |
| 2008/0051703 A1 | 2/2008 | Thornton et al. |
| 2008/0058835 A1 | 3/2008 | Farritor et al. |
| 2008/0058989 A1 | 3/2008 | Oleynikov et al. |
| 2008/0111513 A1 | 5/2008 | Farritor et al. |
| 2008/0221591 A1 | 9/2008 | Farritor et al. |
| 2008/0249359 A1 | 10/2008 | Abraham-Fuchs et al. |
| 2008/0269779 A1 | 10/2008 | Cadeddu et al. |
| 2009/0043246 A1 | 2/2009 | Dominguez |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0171354 A1 | 7/2009 | Deville et al. |
| 2009/0171373 A1 | 7/2009 | Farritor et al. |
| 2009/0259340 A1 | 10/2009 | Umemoto et al. |
| 2010/0114126 A1 | 5/2010 | Neff |
| 2010/0145306 A1 | 6/2010 | Mickley et al. |
| 2010/0160739 A1 | 6/2010 | Van Lue |
| 2010/0194707 A1 | 8/2010 | Hotelling et al. |
| 2010/0256636 A1 | 10/2010 | Fernandez et al. |
| 2010/0318059 A1 | 12/2010 | Farritor et al. |
| 2011/0087223 A1 | 4/2011 | Spivey |
| 2011/0087224 A1 | 4/2011 | Cadeddu et al. |
| 2011/0112623 A1 | 5/2011 | Schatz |
| 2011/0224605 A1 | 9/2011 | Farritor et al. |
| 2011/0237890 A1 | 9/2011 | Farritor et al. |
| 2011/0283822 A1 | 11/2011 | Cadeddu et al. |
| 2011/0284014 A1 | 11/2011 | Cadeddu et al. |
| 2011/0285488 A1 | 11/2011 | Scott et al. |
| 2011/0313415 A1 | 12/2011 | Fernandez et al. |
| 2012/0035416 A1 | 2/2012 | Fernandez et al. |
| 2012/0065627 A1 | 3/2012 | Ghabrial et al. |
| 2012/0078053 A1 | 3/2012 | Phee et al. |
| 2012/0179168 A1 | 7/2012 | Farritor et al. |
| 2013/0012821 A1 | 1/2013 | Lin et al. |
| 2013/0041360 A1 | 2/2013 | Farritor et al. |
| 2014/0358162 A1 | 12/2014 | Valdastri et al. |
| 2016/0045273 A1 | 2/2016 | Campbell et al. |

FOREIGN PATENT DOCUMENTS

| | | |
|---|---|---|
| JP | 2005-028006 | 2/2005 |
| JP | 2007-143371 | 6/2007 |
| WO | 2007/149559 | 12/2007 |
| WO | 2008/103212 | 8/2008 |
| WO | 2009/014917 | 1/2009 |
| WO | 2009/023851 | 2/2009 |
| WO | 2010/083480 | 7/2010 |

(56) References Cited

FOREIGN PATENT DOCUMENTS

| WO | 2011/044468 | 4/2011 |
| WO | 2011/075693 | 6/2011 |
| WO | 2012/035157 A1 | 3/2012 |
| WO | 2012033925 A1 | 3/2012 |
| WO | 2012/164517 A1 | 12/2012 |

OTHER PUBLICATIONS

International Search Report and Written Opinion, PCT/CN2013/000480, dated Aug. 8, 2013, 11 pages.
Satava, R. M., "Innovation and Advanced Technology for the Future of Healthcare," Innovation Forum, Saskatoon, Sep. 2009, 45 pages.
International Search Report of International Search Authority, for international application No. PCT/CN2016/100378, dated Nov. 29, 2016.
Written Opinion of International Search Authority, for international application No. PCT/CN2016/100378, dated Nov. 29, 2016.

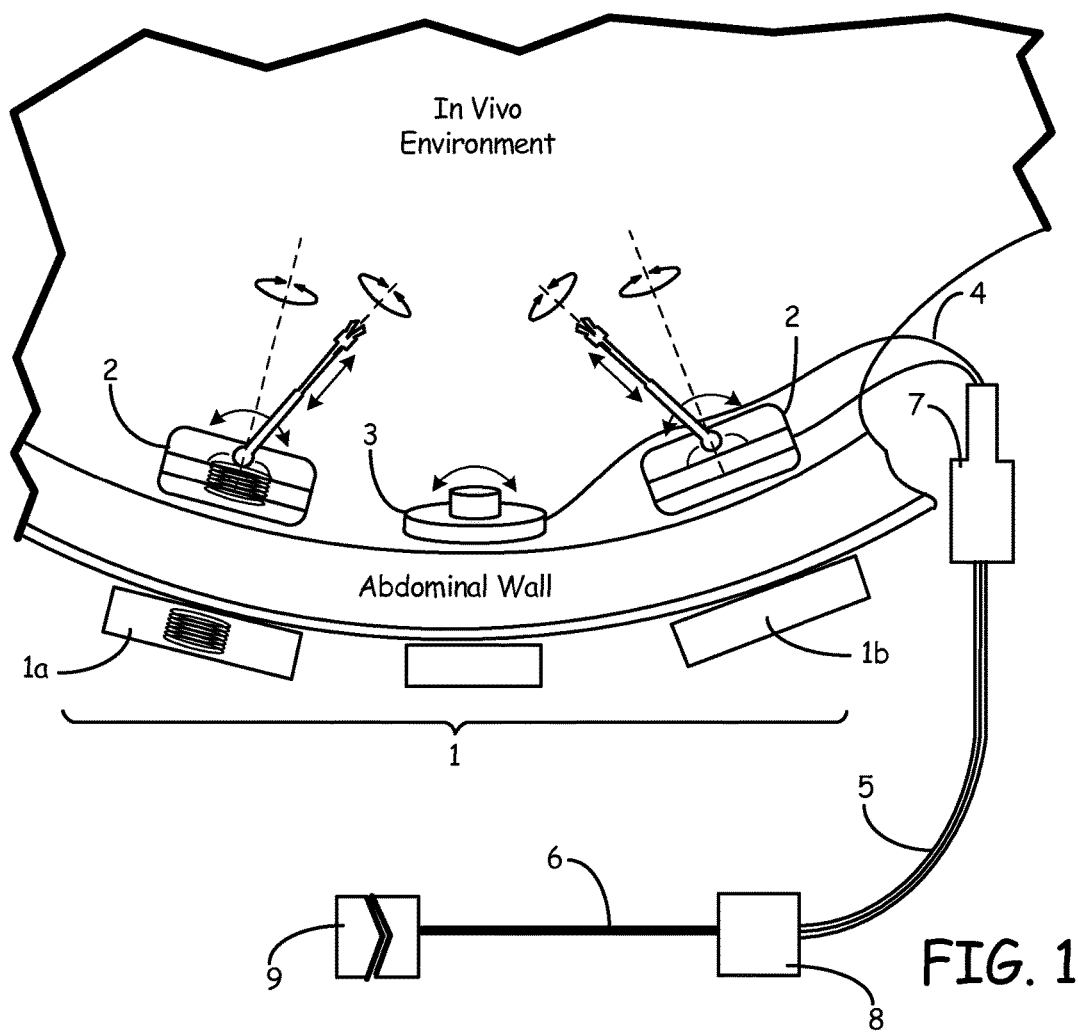
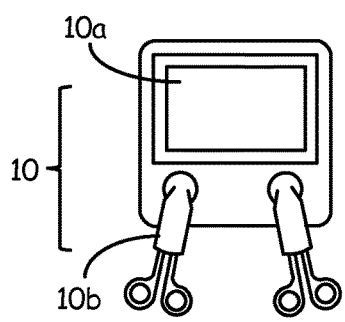
FIG. 1A
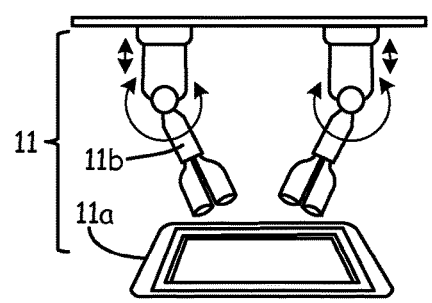
FIG. 1B

MAGNETIC-ANCHORED ROBOTIC SYSTEM

CROSS-REFERENCE TO RELATED APPLICATIONS

This application is a continuation-in-part of U.S. application Ser. No. 13/871,915, filed on Apr. 26, 2013, which claims priority to U.S. Provisional Application No. 61/638,828, filed Apr. 26, 2012, and U.S. Provisional Application No. 61/718,252, filed Oct. 25, 2012, the contents of all of which are hereby expressly incorporated by reference in their entirety including the contents and teachings of any references contained therein.

In addition, this application relates to U.S. application Ser. No. 13/835,653, filed Mar. 15, 2013, U.S. application Ser. No. 13/835,680, filed Mar. 15, 2013, now U.S. Pat. No. 8,891,924, and U.S. application Ser. No. 13/871,926, filed Apr. 26, 2013, now U.S. Pat. No. 9,020,640, titled "Magnetic-Anchored Robotic System," the contents of all of which are hereby expressly incorporated by reference in their entirety including the contents of any references contained therein.

BACKGROUND

Surgeons have traditionally depended on external illumination from the operating room light and adequate exposure to obtain a good surgical view. This often requires large incisions, to provide access for the operation. The introduction of fiber optics in modern endoscopes has allowed surgeons to see clearly with good illumination inside a bodily cavity without having to make a big incision. Minimally Invasive Surgery (MIS) has now replaced most conventional open surgical operations. Computer-assisted or robotic technology has contributed further to the development of MIS as the computer sensors of the robotic machine can reliably and delicately translate the movements of the surgeon's fingers and wrists into movements of the slave laparoscopic instruments inside the body cavities. These developments have allowed good dexterity and precision control of surgical instruments for fine reconstructive surgery in a small confined space.

However, the MIS approach requires multiple incisions for the insertion of the camera and various laparoscopic instruments. Over the past few years, Laparo-Endoscopic Single-Site (LESS) surgery technologies have become available, but these suffer immensely from a lack of proper triangulation between the camera and the working instruments, which is important for good operative ergonomics and hence ease and success of surgery.

Natural orifice translumenal endoscopic surgery (NOTES) is an alternative to open abdominal surgery that uses endoscopic techniques with a view to completely avoid the need for external abdominal wall incisions. Theoretically, NOTES offers advantages by minimizing access trauma and the various complications associated with external incisions including wound infections, pain, hernia formation, unsightly abdominal scars and adhesions.

However, the NOTES approach suffers from significant drawbacks including inadequacy of proper triangulation of surgical instruments and hence poor working ergonomics, an inability to apply off-axis forces, and difficulties in passing multiple instruments into the abdominal cavity for proper surgical manipulations.

BRIEF SUMMARY

In an embodiment, a robotic actuator includes an internal anchor and an instrument. The internal anchor is adapted to be inserted into a body via an entrance port, positioned inside the body, and magnetically coupled with an external anchor positioned outside the body. The instrument is adapted to be inserted into the body via the entrance port and secured to the internal anchor. The instrument includes an end-effector having multiple degrees of movement via multiple axes, and a plurality of actuators that provide the multiple degrees of movement.

In another exemplary embodiment, a surgical system is described. The surgical system comprises an internal anchor assembly. The internal anchor assembly may be configurable to be inserted into and positioned inside a cavity of a body. The surgical system further comprises an external anchor assembly. The external anchor assembly may be configurable to magnetically couple to the internal anchor assembly. The external anchor assembly may comprise a magnetic assembly. The magnetic assembly may include one or more superconducting magnets configurable to generate a magnetic field. The magnetic assembly may further include a conductive housing for receiving the one or more superconducting magnets. The external anchor assembly may further include a temperature control section. The temperature control section may be configurable to control a temperature of the one or more superconducting magnets via the conductive housing. The external anchor assembly may further include an external anchor body configurable to receive the magnetic assembly and the temperature control section. The external anchor body may be fixably positionable outside of the body.

In another exemplary embodiment, an external anchor assembly is described. The external anchor assembly is for use with a surgical system. The surgical system includes an internal anchor assembly configurable to be inserted into and positioned inside a cavity of a body. The external anchor assembly comprises a magnetic assembly. The magnetic assembly includes one or more superconducting magnets configurable to generate a magnetic field. The magnetic assembly further includes a conductive housing for receiving the one or more superconducting magnets. The external anchor assembly further comprises a temperature control section. The temperature control section may be configurable to control a temperature of the one or more superconducting magnets via the conductive housing. The external anchor assembly further comprises an external anchor body. The external anchor body may be configurable to receive the magnetic assembly and the temperature control section. The external anchor body may be fixably positionable outside of the body. The magnetic assembly may be configurable to magnetically couple to the internal anchor assembly via the magnetic field.

In another exemplary embodiment, a method of configuring a surgical system is described. The method comprises providing an internal anchor assembly. The internal anchor assembly may be configurable to be inserted into and positioned inside a cavity of a body. The method further comprises providing an external anchor assembly. The external anchor assembly may include a magnetic assembly, a temperature control section, and an external anchor body. The magnetic assembly may include one or more superconducting magnets configurable to generate a magnetic field. The magnetic assembly may further include a conductive housing for receiving the one or more superconducting magnets. The temperature control section may include a heat rod and a cyro-cooler. The heat rod may be in contact with the conductive housing and the cyro-cooler. The external anchor body may be configurable to receive the magnetic assembly and the temperature control section. The method may further comprise preparing the one or more superconducting magnets. The preparing the one or more superconducting magnets may include providing a charging field. The preparing the one or more superconducting magnets may further include configuring the cryo-cooler to a first temperature. The ambient temperature may be operable to bring a temperature of the one or more superconducting magnets to be lesser than or equal to a second temperature. The preparing the one or more superconducting magnets may further include bringing the magnetic assembly to the charging field. The preparing the one or more superconducting magnets may further include ramping up a magnetic field generated by the charging field at a first rate. The preparing the one or more superconducting magnets may further include configuring the cryo-cooler to a third temperature less than the first temperature. The third temperature may be operable to bring the temperature of the one or more superconducting magnets to be lesser than or equal to a fourth temperature less than the second temperature. The preparing the one or more superconducting magnets may further include ramping down the magnetic field generated by the charging field at a second rate. The preparing the one or more superconducting magnets may further include removing the magnetic assembly from the charging field when the magnetic field generated by the charging field reaches a final magnetic field value.

BRIEF DESCRIPTION OF THE DRAWINGS

FIG. 1 is a general schematic view of an exemplary surgical robotic system.

FIGS. 1A and 1B are front views of exemplary human-machine interfaces.

DETAILED DESCRIPTION

A Magnetic-anchored Robotic System (MRS) allows computer-assisted minimally-invasive surgery using multiple independent in-vivo miniature robots that can have a full seven-degrees of freedom of movement in different axis (note that in addition to the degrees of freedom of movement of the miniature robots discussed below, two more degrees of freedom are available by translating the miniature robots along the abdominal wall). Intra-abdominal operations can be performed under the surveillance of an in-vivo swivel camera under remote control by the surgeon through an external computer console. Each of the miniature robotic instruments, camera and other devices may be inserted into the abdominal cavity via either a single incision (for example, through the umbilicus) or through a natural orifice and may be secured into position by an external electro-magnetic anchoring and positioning device outside the abdominal wall at selected sites to provide operative ergonomics and triangulation between camera and instruments. The control of such miniature robotic system inside the abdominal cavity can be, for example, via a wired or a hybrid combination of wired and wireless communications, depending on the situation and the condition of the patient. In some arrangements, power will be transmitted to the miniature robotic instruments (effectors), by a pair of conductors, while the control signals of the same can be transmitted by wire or wirelessly.

The camera as well as all laparoscopic instruments can be inserted into the abdominal cavity through a single incision or through a natural orifice. The laparoscopic instruments can then be anchored and positioned through an external electro-magnet placed outside the abdominal wall. MRS can therefore allow MIS to be performed with the benefits of both computer-assisted or robotic surgery, as well as using either only a single incision or through a natural orifice. An exemplary MRS may include:

(i) one or more externally-mounted electro-magnetic anchoring and positioning devices;

(ii) multiple internal electro-magnetic anchoring devices, each fitted with an independent miniature robotic surgical instrument capable of, for example, seven-degrees freedom of movements via multiple axis; and (iii) a surgeon's computer console that provides surgical control and manipulation.

Thus, exemplary advantages including minimized access trauma, provision of unrestricted or less restricted and more dexterous movement of instruments inside the cavity and enabling proper or improved triangulation of instruments for optimal or improved operative ergonomics can be achieved.

Figure 23:
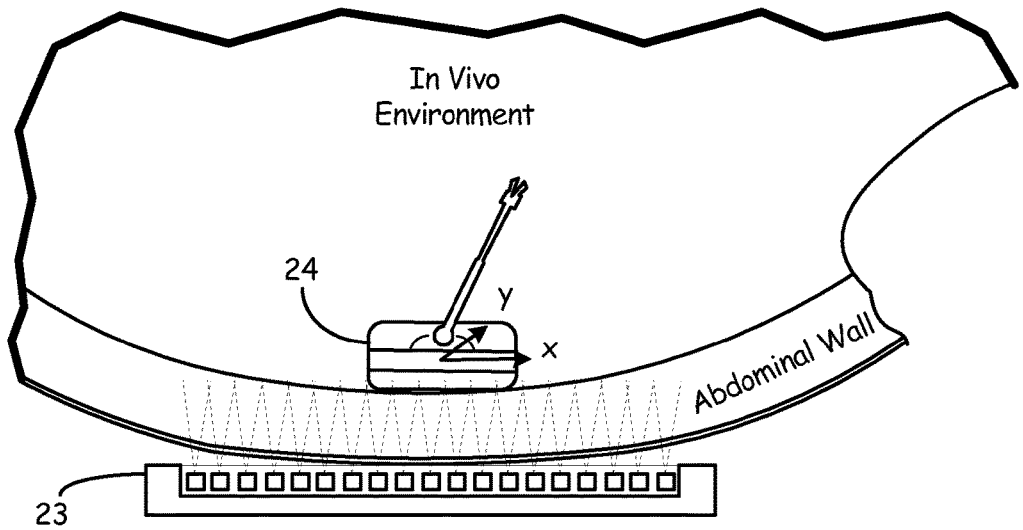
FIG. 23 is a side view of an exemplary micro robotic manipulator in an in vivo environment.
Figure 24A:
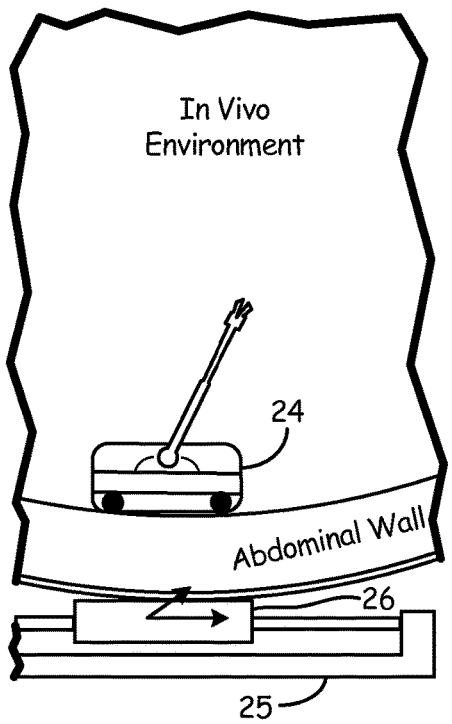
FIGS. 24A and 24B are side views of an exemplary micro robotic manipulator in an in vivo environment.
Figure 24B:
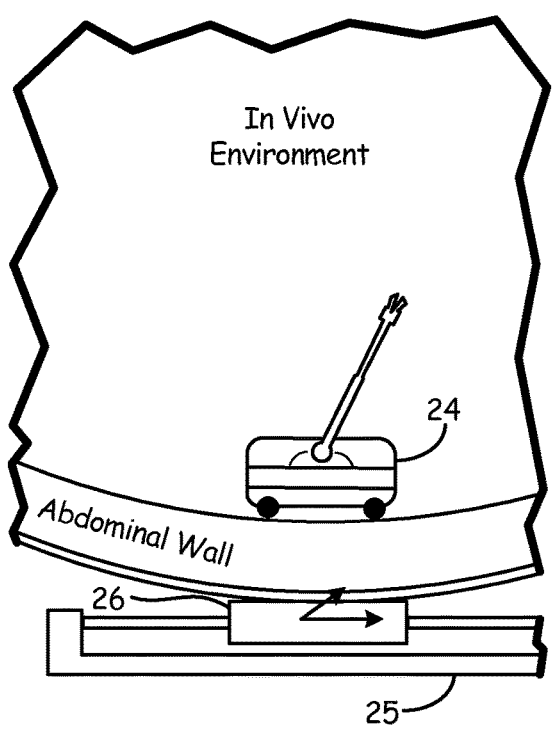

Referring to FIG. 1, the system may include one or more magnetic or electromagnetic location fixing device(s) 1 (hereafter collectively referred to as the electromagnetic location fixing device 1, which includes examples including permanent/non-electric magnets unless otherwise specifically excluded) placed on the outer abdominal wall associated with remotely controlled robotic manipulator(s) 2 inside the body. The electromagnetic location fixing device 1 may include a servo mechanism that is remotely controlled to control the position of the internal electromagnetic anchoring device. The robotic manipulator inside the human body can therefore be moved and be positioned by an externally supplied magnetic field interacting with one or more permanent magnets or electromagnets included in the electromagnetic location fixing device 1 together with the internal electromagnetic anchoring device. Such an externally supplied magnetic field may be moved by a X-Y servo mechanism to a designated position thus relocating the robotic arm 24 to the designated position and then refix again as shown in FIG. 24. As another example, the electromagnetic location fixing device 23 shown in FIG. 23 may be in the form of a linear induction stator on the outside of the abdominal wall such that when an alternating current of appropriate frequency is applied to the stator on the outside of the abdominal wall, the inside flap 24 will levitate and move forward. When such an alternating current is applied in pulse form, the inside flap 24 will move forward in small steps. Such control may also be provided by a control computer.

For illustrative purposes, each location fixing device is shown with one robotic manipulator; however, there may be multiple robotic manipulators for one location fixing device or multiple location fixing devices for one robotic manipulator. For example, each device may detect the current position of the end effector of the corresponding multi-axis micro robotic manipulator 2 inside the human body. The multi-axis micro robotic manipulator 2 inside the body may detect the current position of the end effector. The micro robotic manipulator 2 may include various end effectors such as a gripping device 16 (for example, as shown in FIG. 6) and an imaging device 3 for performing a given treatment and visualizing the in vivo environment respectively.

The manipulator 2 can be folded and inserted into the body cavity through an entrance port 7 in the form of a hollow cylinder mounted on a minimal invasive opening or the like of the patient. It may be connected to a flexible cable 4 passing through the entrance port 7 and linked to a central control computer 8 via an electrical wire 5 or wirelessly. The entrance port 7 is in the range of 1.5-2 cm in diameter in some examples but may vary. The range of 1.5-2 cm is advantageous as it is big enough for equipment (manipulators, etc.) to pass through and small enough to be accommodated by most natural orifices.

Figure 2A:
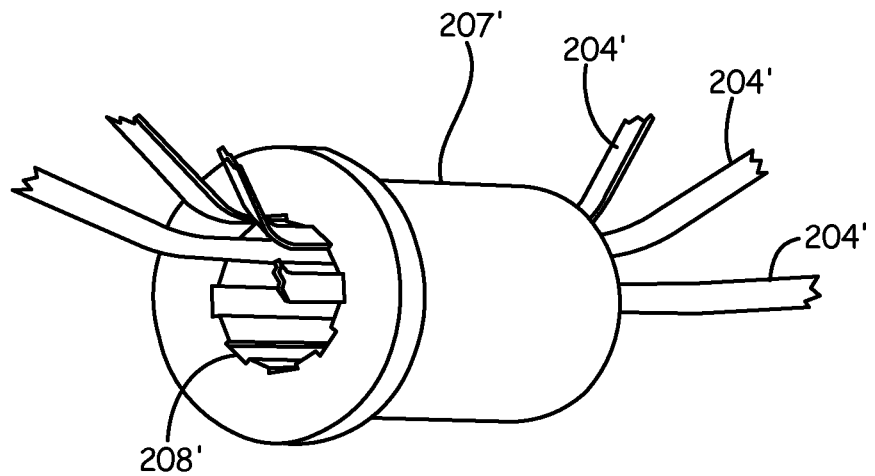
FIGS. 2A and 2B are perspective views of exemplary entrance ports.
Figure 2B:
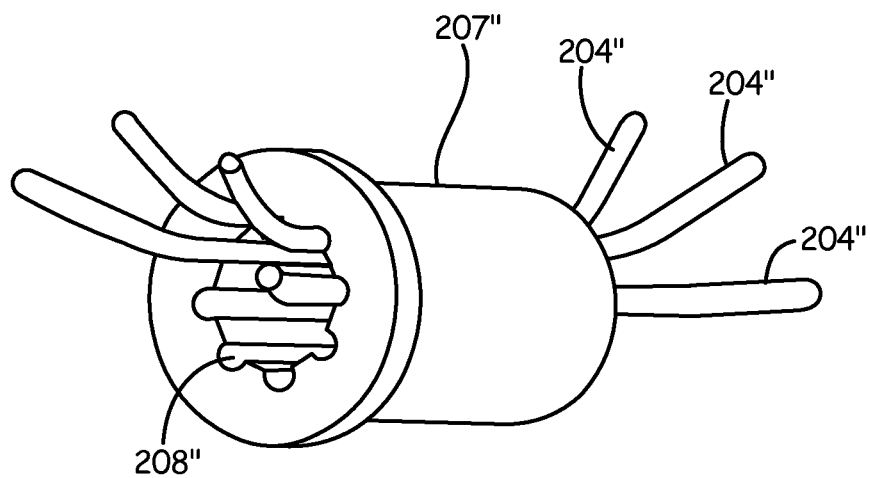

Referring to FIGS. 2A and 2B, the entrance ports 207' and 207" may be shaped to accommodate flexible cables 204' and 204" in a manner that permits multiple of the manipulators 2 to be inserted through the same single entrance port 207. An inner wall of the entrance ports 207' and 207" includes 207" includes one or more recesses of a shape complementary to the wires 204' and 204".

In the example shown in FIG. 2A, the recesses 208' in the inner wall of the entrance port 207' are slot shaped and include a flat surface to accommodate the flat cable 204'. In some examples, a cross section of the inner wall may be in the shape of a polyhedron having the recesses 208' immediately joining an adjacent recess 208'. In other examples, the recesses 208' may be distributed circumferentially about the inner surface of the entrance port 207'. The recesses 208' may be distributed equally or unequally about the inner surface of the entrance port 207'.

In the example shown in FIG. 2B, the recesses 208" in the inner wall of the entrance port 207" are rounded to accommodate the round cable 204". In some examples, the recesses 208" immediately join an adjacent recess 208". In other examples, the recesses 208" may be distributed circumferentially about the inner surface of the entrance port 207". The recesses 208" may be distributed equally or unequally about the inner surface of the entrance port 207".

It will be appreciated that the above described shapes are exemplary in nature and can be selected from a variety of other shapes according to a particular implementation. Providing the recesses 208 allows for the use of the same entrance port for many of the manipulators 2 by clearing the opening of the entrance port 207 of the cables 204 to allow passage of another manipulator 2. In this way, trauma associated with the insertion of entrance ports, trocars, etc., can be minimized by reusing the same single entrance port for several or all of the manipulators 2.

Depending on the application, the signal transmission between the remotely controlled micro robotic manipulator 2 and the central control computer 8 can be performed through a wired connection (for example, via the entrance port 7 over a conductive cable or an optical cable) or a wireless connection (for example, via inductive coupling with a pickup coil incorporated in the location fixing device as shown in device 1a). Power for the manipulator 2 may also be supplied via the location fixing device 1 wirelessly through the abdominal wall. A hybrid such as a wired power supply and wireless control signal may also be used.

Also, in cases where the electromagnetic location fixing device 1 is controllable by the central control computer 8, a wired or wireless connection may be provided from the central control computer 8 to the electromagnetic location fixing device 1. Alternatively, or in addition, electromagnetic location fixing device 1 may communicate wirelessly with the micro robotic manipulator 2, which is connected to the central control computer 8 through a wired connection, for example via the entrance port 7, to provide communication between the electromagnetic location fixing device 1 and the central control computer 8. The central control computer 8 may control positioning servos of the electromagnetic location fixing device 1 as well as activating/deactivating a fixing control. The fixing control may be, for example, activating an electromagnet in the electromagnetic fixing device 1. The fixing control is not necessarily a discrete on/off control and may also be variable.

The central control computer 8 can adjust the positions and actions of the manipulators 2 independently of each other by the corresponding movement of the trigger unit 10b, 11b controlled by an operator through a human machine interface 9 connecting to the controller via a cable 6. The interface 9 may include a display screen 10a, 11a and a pair of trigger units 10b, 11b, which may be different types such as the remote operation type 10 shown in FIG. 1A and multi-axis end-effector simulator type 11 shown in FIG. 1B. In the multi-axis end-effector simulator type 11, the trigger unit 11b has a multi-axis robotic joint that can provide fine position control of the end effector of the manipulator 2 with several degrees of freedom. The movement control can also include force feedback.

Also, the number of inserted miniature robots is not limited to the number that can be controlled by one operator through the human machine interface 9. A second human machine interface may be provided for an assistant operator to also control miniature robots if needed for the operation.

Figure 3:
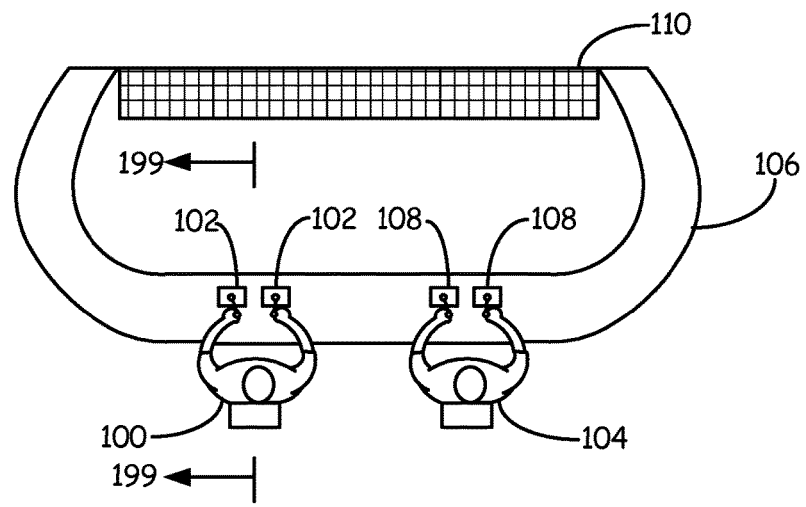
FIG. 3 is a perspective view of an exemplary surgeon console.

Referring to FIG. 3, a main surgeon 100 controls a pair of controls 102 while an assistant 104 working on the same surgeon console 106 or another surgeon console controls additional controls 108. The main surgeon 100 and/or the assistant 104 may also control various cameras. The main surgeon 100 and the assistant 104 can view the same display 110 or they may view separate displays, for example, showing different views of the patient. The display 110 may be a 2D display, a 3D display, a naked eye 3D display, or other type of suitable display. The assistant 104 may simultaneously operate and assist in the operation. Two or more operators may advantageously work on the same patient at the same time while maintaining dialog with each other. It will be appreciated that while a main surgeon and an assistant surgeon have been described, the console 106 may be operated by any one or two (or more) operators generically.

Figure 4A:
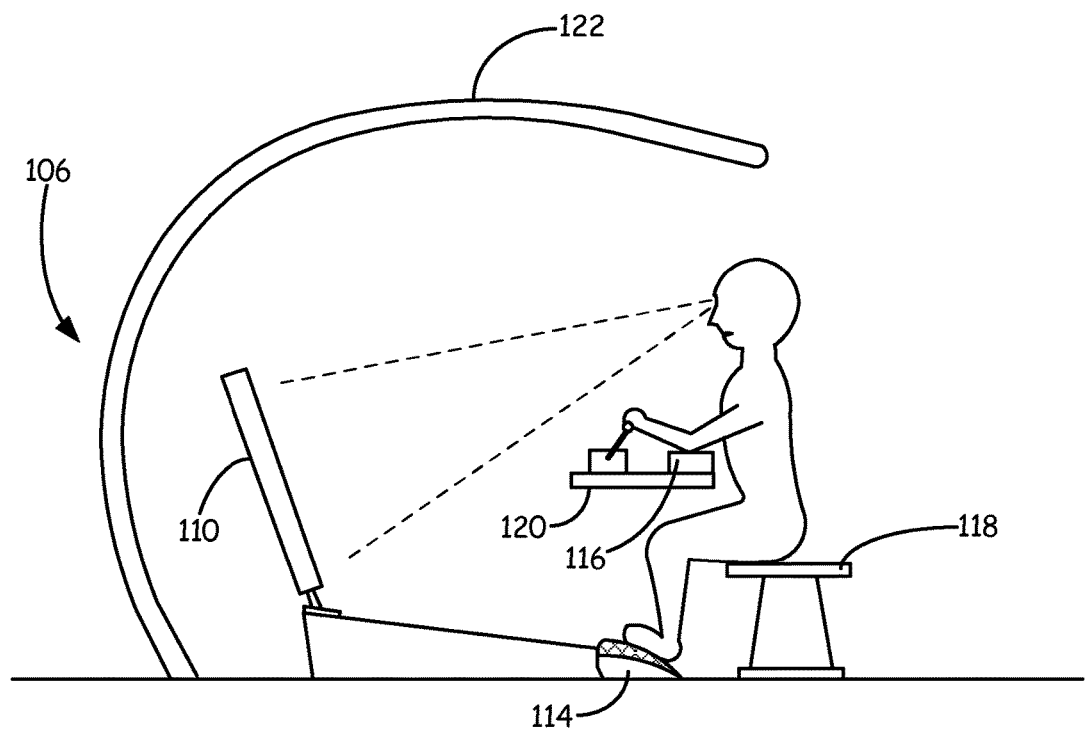
FIG. 4A is a side view of an exemplary surgeon console.

Referring to FIGS. 3 and 4A, the surgeon console 106 may be ergonomically arranged including one or more of the foot rest 114, the arm rest 116 and the seat 118. The foot rest 114 may incorporate switches to switch the controls 102 (and/or the controls 108) to control the camera instead of the manipulators/robots or vice-versa. The foot rest 114 may also incorporate controls to control manual focusing of the camera(s). The foot rest 114, arm rest 116, controls 102, controls 108 and/or any combination thereof may include sensor/actuators to detect the presence of the operator in order to enable/disable the robotic system.

The surgeon console 106 may also be arranged to avoid light reflection. For example, the display 110 may be positioned such that at least a portion is below a height of the table 120 at which the surgeon sits. The display 110 may also be angled such that reflections are not passed or reduced to the viewer at the table 120. The light shelter 122 may also be provided to reduce ambient lighting that may could cause reflections.

Haptic feedback may be provided to the main surgeon 100 and/or the assistant 104. A resisting force may be measured by the in-vivo robotic manipulator 2, for example via an onboard sensor such as a load cell. The resisting force may also be estimated from an amount of energy (e.g., voltage, current or power) used by the manipulator 2. Force feedback based on the resisting force may be provided to the main surgeon 100 and/or the assistant 104 via the manipulators 102 and 108 respectively.

For example, with reference to FIGS. 4B and 4D-4F, a surgeon's manipulator 102 may include motor/encoders 402, 404, 406, 408, 410, 412 and 414. The motor/encoder 402 may detect and provide haptic feedback for pitch. For example, the motor/encoder 402 may be coupled to a joint element 403 with a bushing/washer 405 there between. Thus, the motor/encoder can detect rotation with respect to the joint element 403 and provide haptic feedback to this axis of movement. The motor/encoder 404 may detect and provide haptic feedback for sway. The motor/encoder 406 may detect and provide haptic feedback for wrist yaw. The motor/encoder 408 may detect and provide haptic feedback for extension/retraction. For example, the motor/encoder 408 may be coupled to the linear guide rail 409. As the linear guide rail is extended/retracted by the surgeon/operator, the motor/encoder 408 is rotated. Thus, the motor/encoder 408 can detect extension/retraction and provide haptic feedback to this axis of movement. The motor/encoders 410 and 412 may detect and provide haptic feedback for gripping. The motor/encoder 414 may detect and provide haptic feedback for wrist pitch. The motor/encoders 404, 406, 410, 412 are arranged in a manner similar to described above with respect to the motor/encoder 402.

Manipulator ends 420, 422 correspond with manipulator ends of a robotic actuator. The manipulator ends 420, 422 include contact portions 424, 426 (e.g., cylinders), to provide opposing surfaces by which movement of the manipulator ends by the surgeon in various directions is facilitated. The manipulator ends 420, 422 are respectively coupled to the motor/encoders 410, 412. The manipulator ends 420, 422 may be positioned adjacent to each other with the motor/encoders 410, 412 extending away from the manipulator ends 420, 422 in different (in some cases opposite) directions. Opposing ends of the motor/encoders 410, 412 may be secured to a frame 428, which may be C shaped.

The frame 428 may be secured to the motor encoder 414 via a frame member 430. The frame member 430 may be secured to the frame 428 at a central point of the frame 428 such that a rotational axis is centered. The motor/encoder 414 may also be coupled to a frame member 432. Thus, the motor/encoder 414 may detect rotational movement of the frame member 430 with respect to the frame member 432 thereby detecting rotational movement of the entire assembly including the manipulator ends 420, 422 and the motor/encoders 410 and 412.

The frame member 432 may be coupled to the motor/encoder 406 and may include a bend (for example, approximately 90 degrees). Thus, the motor/encoder 406 can detect rotational movement of the entire assembly including the manipulator ends 420, 422 and the motor/encoders 410, 412 and 414.

The motor/encoder 406 may be secured to a first portion 434 of the linear guide rail 409, which includes the first portion 434, the carriage 435 and the second portion 438, for example via the frame member 436. As described above, the motor/encoder 408 is coupled to the linear guide rail 409 to detect movement of the first portion (e.g., a sliding linear guide rail) 434 via a gear running on the second portion (e.g., a rack) 438 to detect movement of the first portion 434 relative to the carriage 435, which may be stationary, mounted to the frame member 441. Thus, the motor/encoder 408 can detect extension/retraction of the entire assembly including the manipulator ends 420, 422 and the motor/encoders 406, 410, 412 and 414.

The motor/encoder 404 may be coupled to the motor/encoder 408 via the bent frame member 441, which may be bent approximately 90 degrees. Thus, the motor/encoder 404 can detect rotational movement of the entire assembly including the manipulator ends 420, 422 and the motor/encoders 406, 408, 410, 412 and 414. The motor/encoder 402 may be coupled to the motor/encoder 404 via the joint element 403. The joint element 403 may be a frame member or a block that couples the motor/encoders 402 and 404 at different faces thereof. Bushings/washers (e.g., 405) may be provided between the motor/encoders 402 and 404 and the joint 403. The motor/encoder 402 may be secured to a frame member 442, which may be bent, for example at 90 degrees. The frame member 442 may provide the base 440. Thus, the motor/encoder 402 may detect rotational movement of the entire assembly with respect to the base 440.

When a position of the manipulator ends 420,422 is changed by the surgeon, the motor/encoders 402, 404, 406, 408, 410, 412 and 414 can detect movement along the different axis of the manipulator 102 as described above. This movement can be directly correlated to movement along the respective axis of the in-vivo robotic manipulator. For example, extension of the linear guide rail 409 can directly correspond to extension of the robotic manipulator about axis 308; rotation of the motor/encoder 414 can directly correspond to rotation about the axis 314, etc. In particular, the degrees of movement may be constrained in a manner that corresponds to the freedom of movement of the robotic manipulator. Thus, the surgeon can easily control the precise positioning of the entire robotic actuator in addition to the relative location of the manipulator ends to the base. This allows for superior control of the robotic manipulator.

The described haptic feedback may be in the form of resistance, vibration, or other forms of feedback. The motor/encoders may also be capable of setting the manipulator 102 to a specified position. For example, at the beginning of an operation, the manipulator 102 may be driven to a starting position corresponding to the position of a corresponding robot manipulator. In this regard, the motor/encoders may have the capability of determining absolute position (for example, via a potentiometer) or relative position (for example, via a digital rotation segmented input).

Figure 4C:
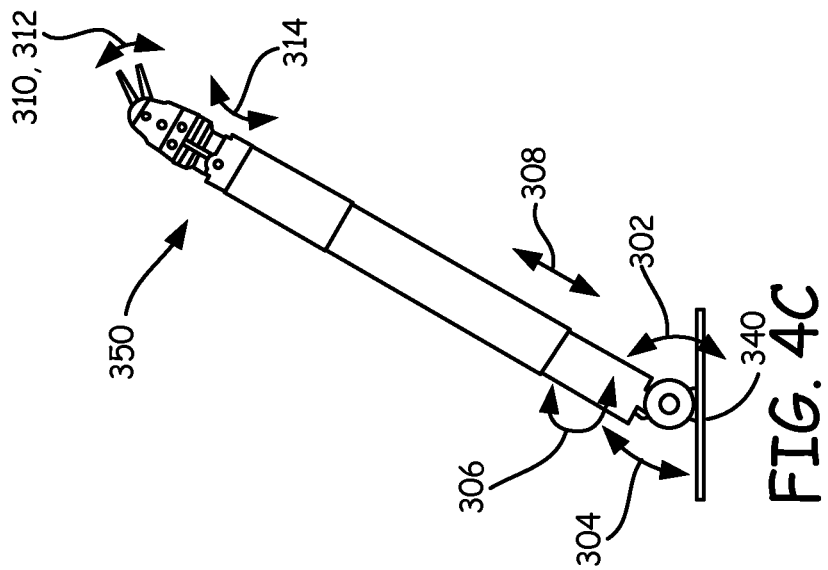
FIG. 4C is a side view of an exemplary micro robotic manipulator.
Figure 4B:
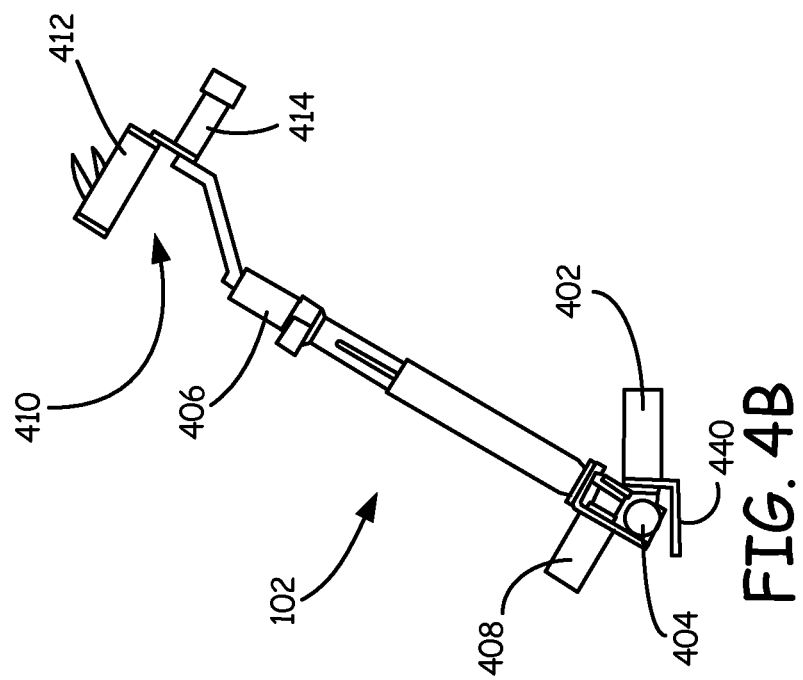
FIG. 4B is a side view of an exemplary surgeon manipulator.
Figure 4D:
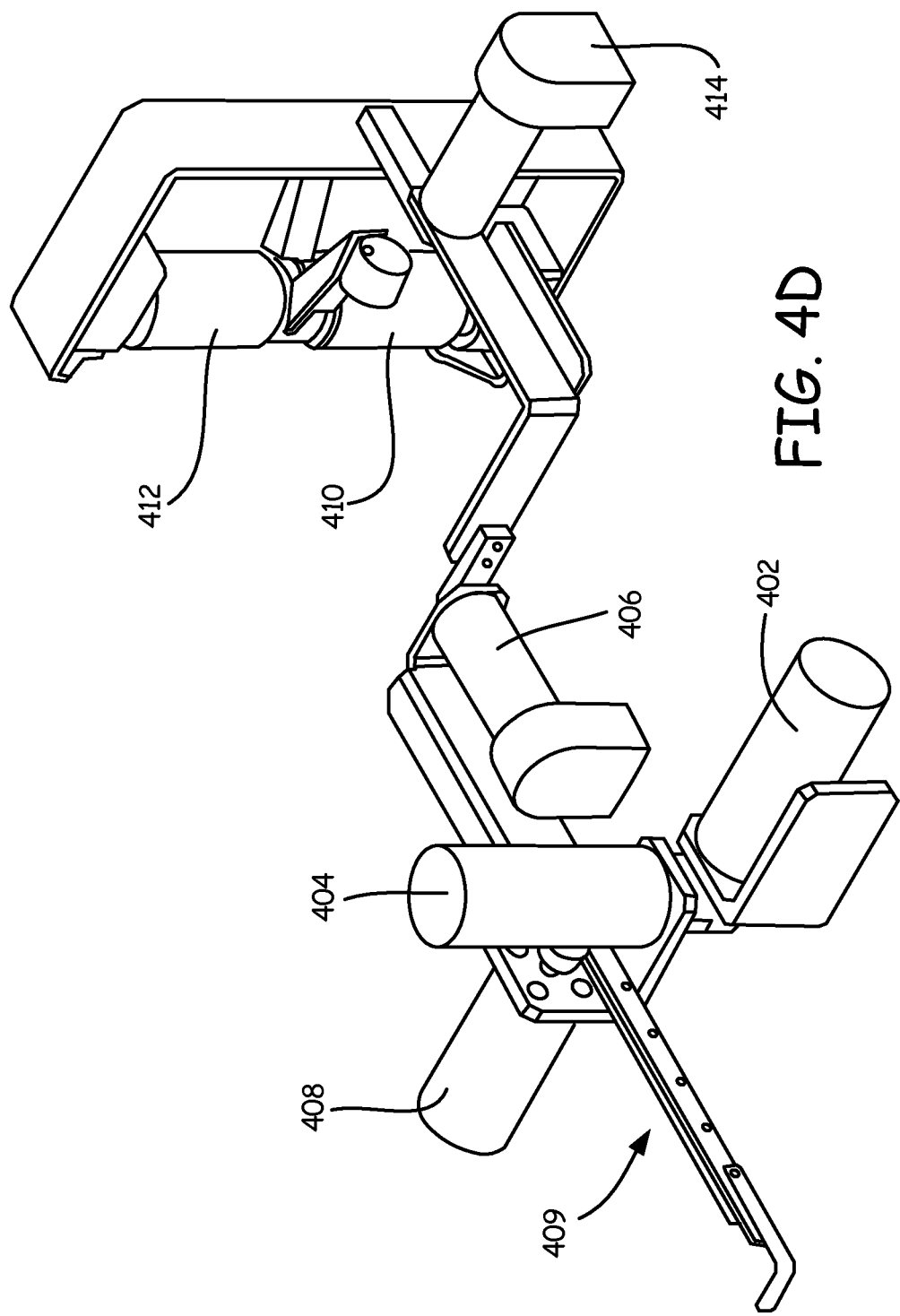
FIG. 4D is a perspective view of an exemplary surgeon manipulator.
Figure 4E:
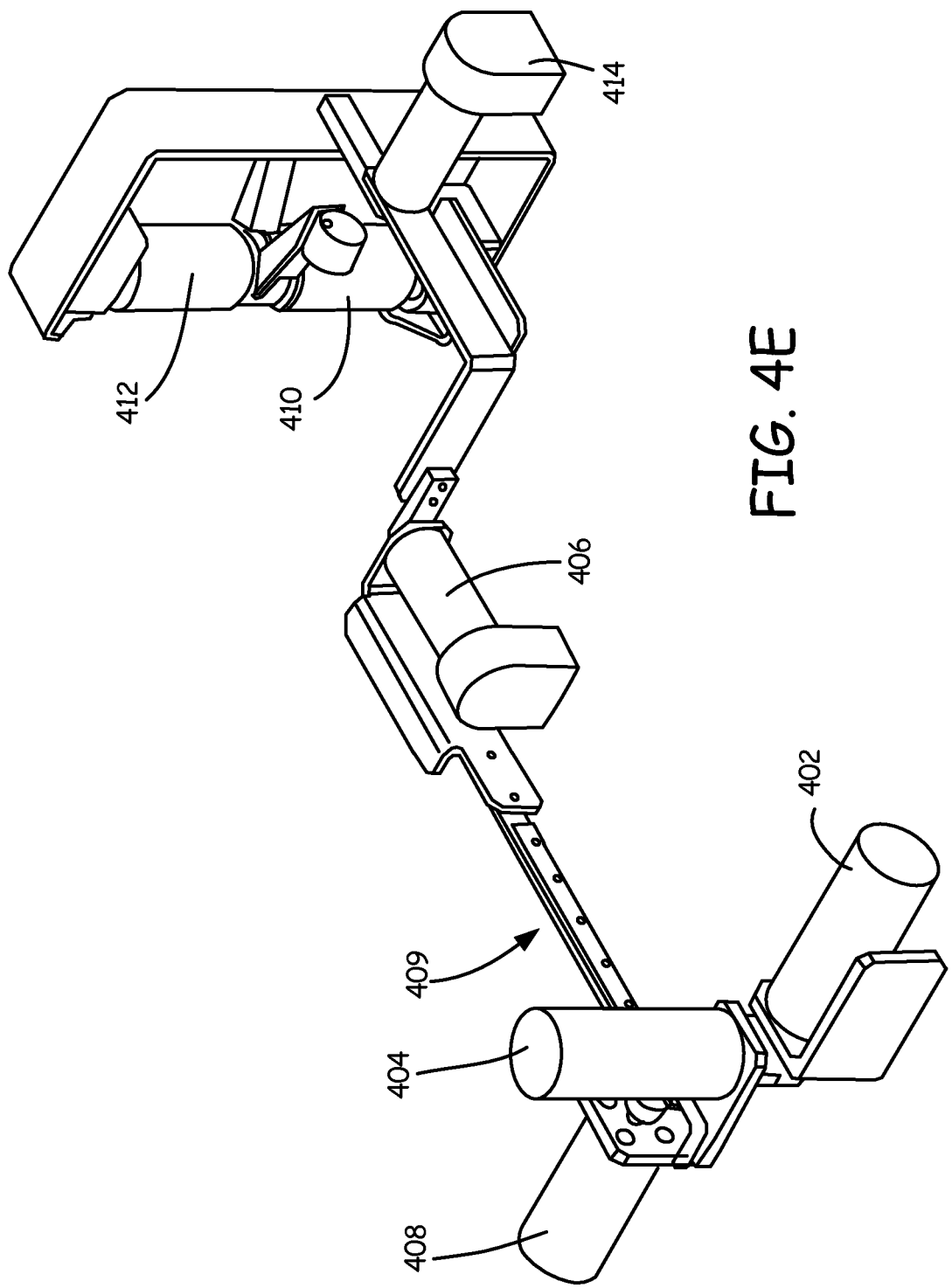
FIG. 4E is a perspective view of the exemplary surgeon manipulator of FIG. 4D in an extended position.
Figure 4F:
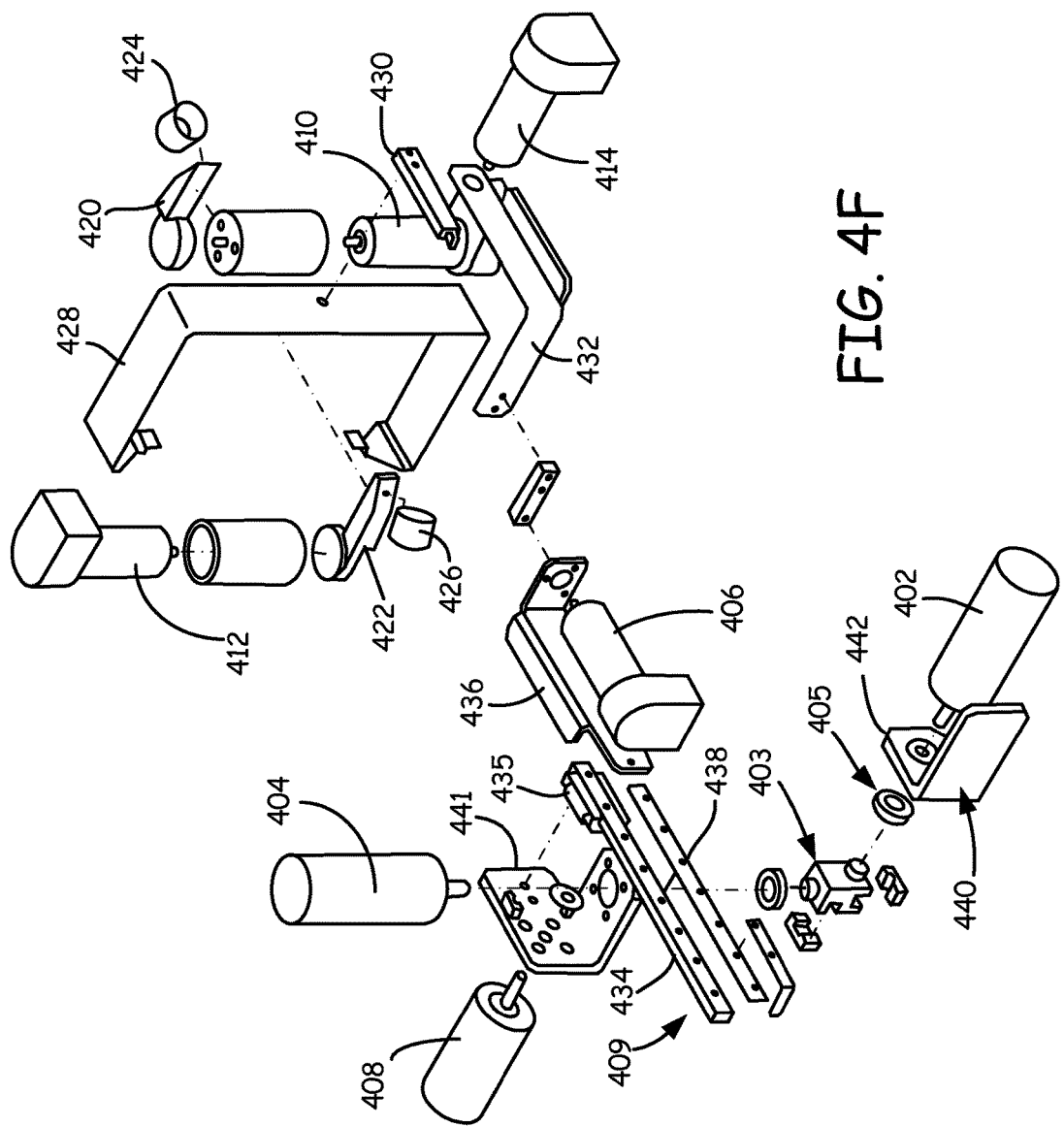
FIG. 4F is an exploded view of the exemplary surgeon manipulator of FIG. 4D.

The motor/encoders 402, 404, 406, 408, 410, 412 and 414 may directly correspond on a one to one basis with the axis of movement 302, 304, 306, 308, 310, 312 and 314 of the micro robotic actuator 350, shown in FIG. 4C. Thus, a surgeon's manipulator may be exactly mimicked for every axes of a corresponding in-vivo robot arm. This allows advantages such as a good feel of control and ergonomics for the surgeon.

Figure 4G:
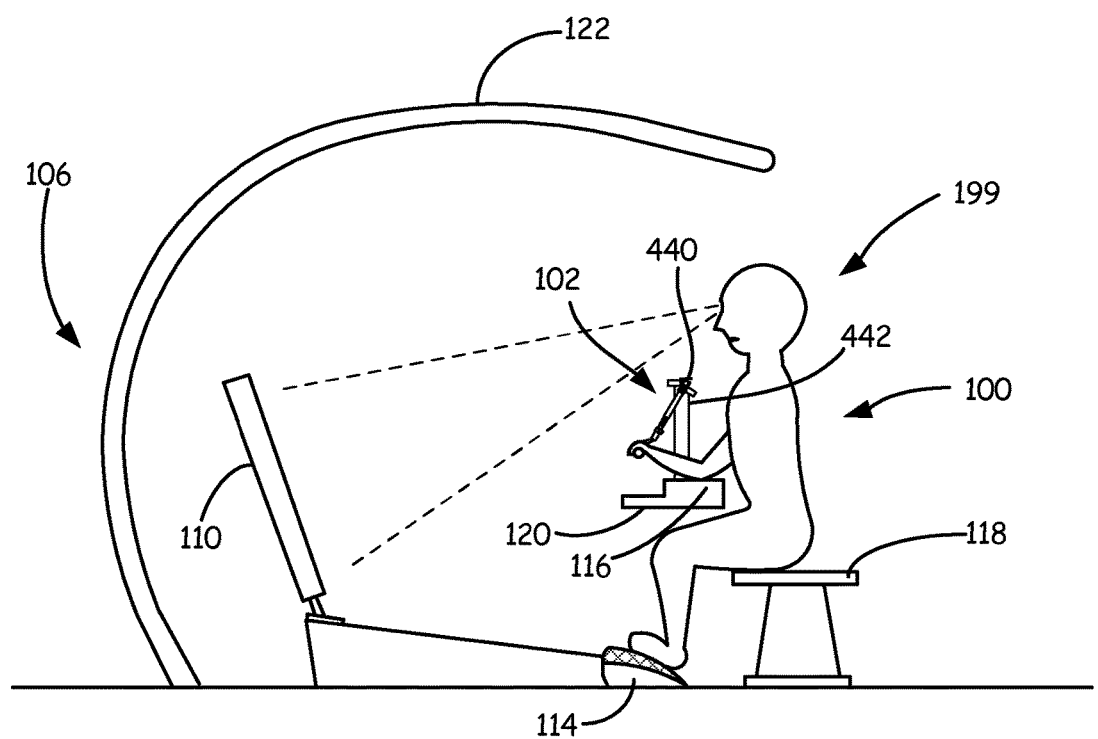
FIG. 4G is a side view of an exemplary surgeon console.

With reference to FIG. 4C, the base 340 of the robot manipulator 350 is generally attached to the inside of the abdominal wall, which in normal surgery will be on top. This arrangement of the manipulator end extending in a downward direction from a base of the robot manipulator may be emulated by positioning the anchor point 440 of the surgeon's manipulator 102 in the configuration as shown in FIG. 4G. The anchor point 440 of the surgeon's manipulator may be secured to a frame having a vertical member that positions the anchor member 442 above the arm rest 116. Thus, the surgeon's manipulator is provided in an orientation that corresponds with the orientation of the robot manipulator 340 during a surgical procedure. This orientation having a direct correspondence between the surgeon's manipulator and the robot manipulator makes direct, precision haptic feedback of each axis of movement to the surgeon possible.

Figure 5:
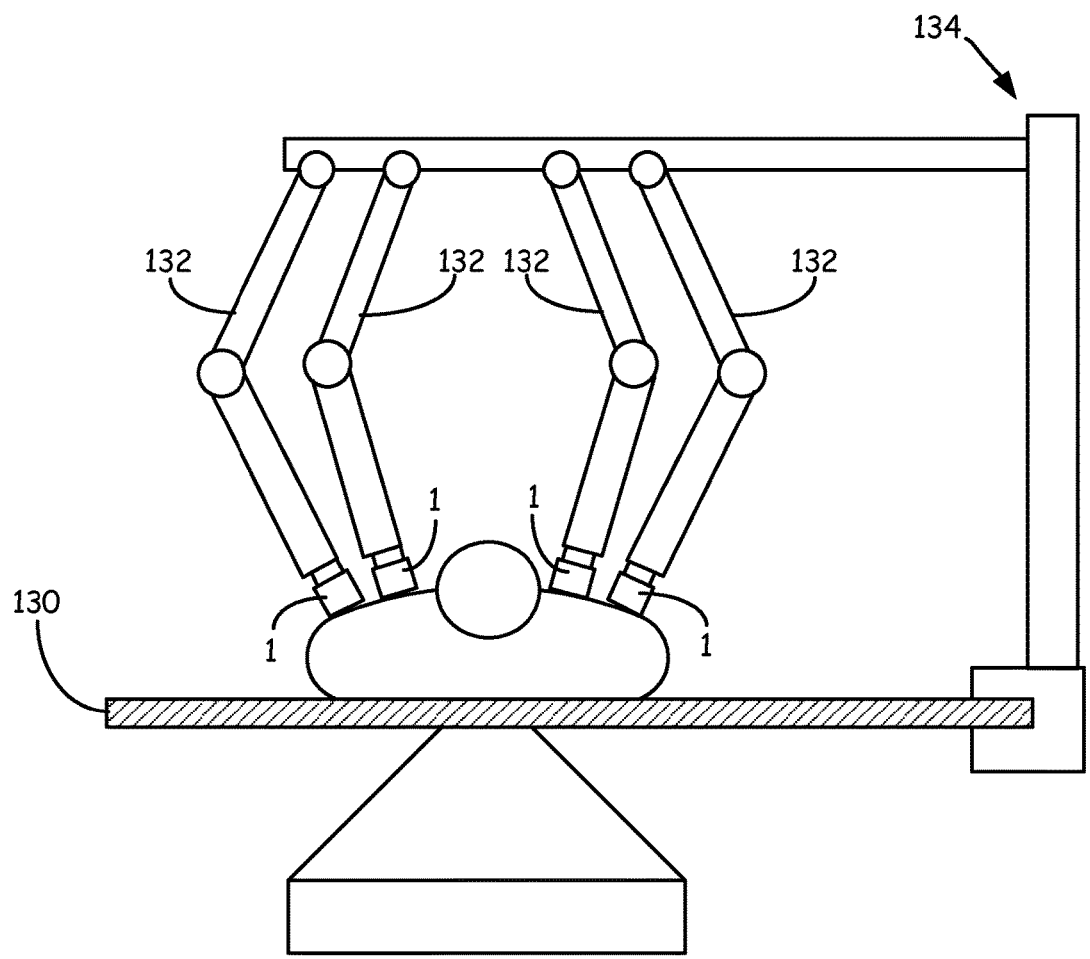
FIG. 5 is a side view of an exemplary patient table.

Referring to FIG. 5, an exemplary patient table 130 is shown. A plurality of the electromagnetic location fixing devices 1 may be coupled to arms 132. The arms 132, may be secured or coupled to the gantry 134, which is secured or coupled to the table 130. Thus, the whole system may move simultaneously with the patient. This allows for the changing of the position of the patient with the table intraoperatively without the need to undock the robotic system from the table and operations that require changes in patient position during the surgical procedure are facilitated. Also, the arms 132 may be servo driven for repositioning or adjusting an orientation of the electromagnetic location fixing devices 1.

Figures 6A, 6B:
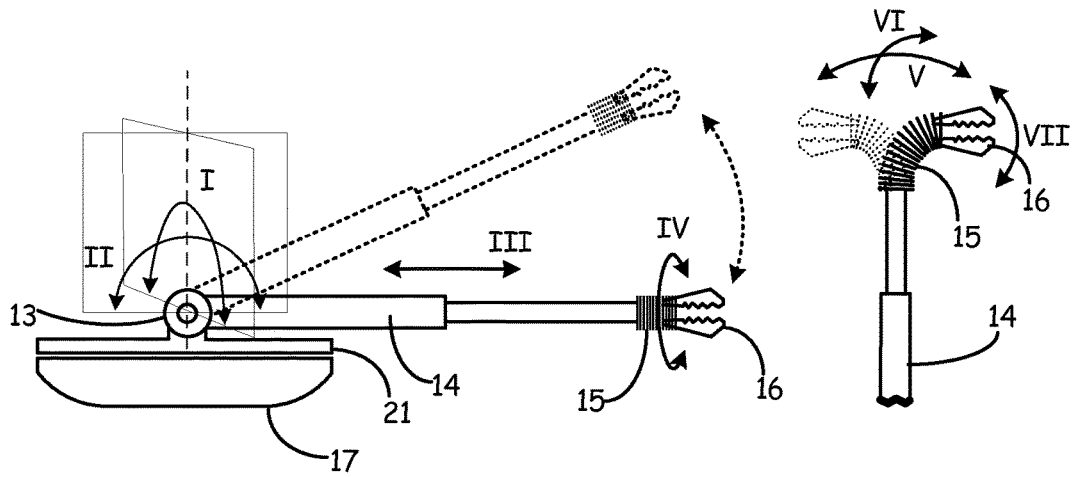
FIGS. 6A and 6B are side views showing 7-axis movement of an exemplary micro robotic manipulator.

Referring to FIGS. 6A and 6B, the axis of movement of the micro robotic manipulator 2 may have several different types of configurations. In the example shown in FIGS. 6A and 6B, 7-axis movement is shown. The joint 13 can rotate along the axes I and II, and the arm 14 can translate along direction III. The wrist 15 can rotate along axis IV, bend along axis V and bend along axis VI. A gripper/end effector 16 may also open and close along the axis VII, which could include rotational and/or translational movement. A portion of the micro robotic manipulator 2 having a joint with rotational axis similar to that of joint 13 and axes I and II as shown in FIG. 6 is referred to as Type A as a matter of convenience and is non-limiting.

Figures 7A, 7B:
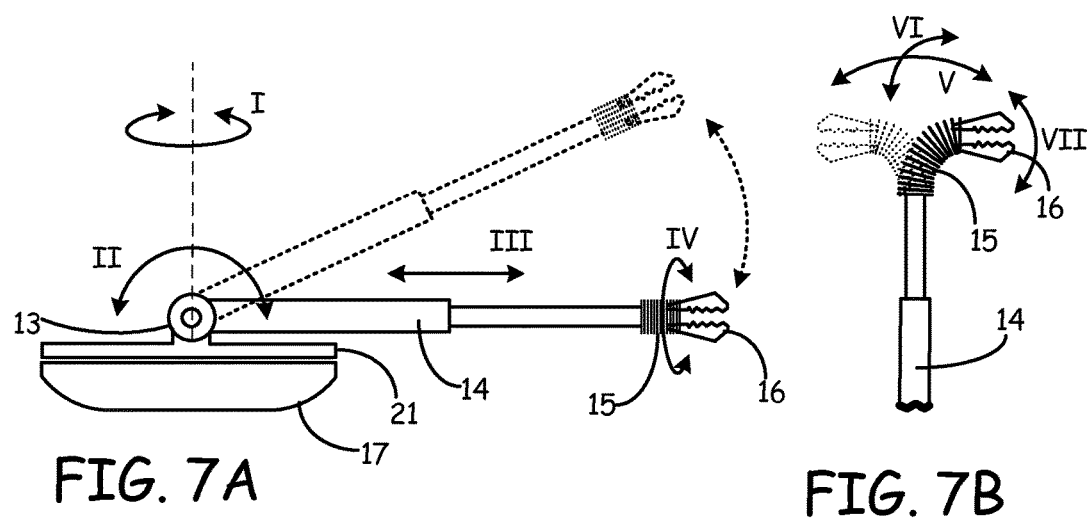
FIGS. 7A and 7B are side views showing 7-axis movement of an exemplary micro robotic manipulator.

FIGS. 7A and 7B show another configuration of the 7-axis movement of the manipulator 2 in which joint 13 rotates along axis I in another direction. A portion of the micro robotic manipulator 2 having a joint with rotational axis similar to that of joint 13 and axes I and II as shown in FIG. 7 is referred to as Type B as a matter of convenience and is non-limiting.

The enclosure of the manipulator 2 may facilitate the insertion of the manipulator into the body and protect the robotic arm and end effector inside the manipulator during insertion. It may include a base 21 and a pair of foldable flaps 17 on both sides of the base 21. As a non-limiting example, the flaps 17 may have a maximum diameter of 18 mm in a folded configuration. A maximum diameter of 18 mm is advantageous as it works well with an entrance port sized for use with most natural orifices.

Figures 8A, 8B:
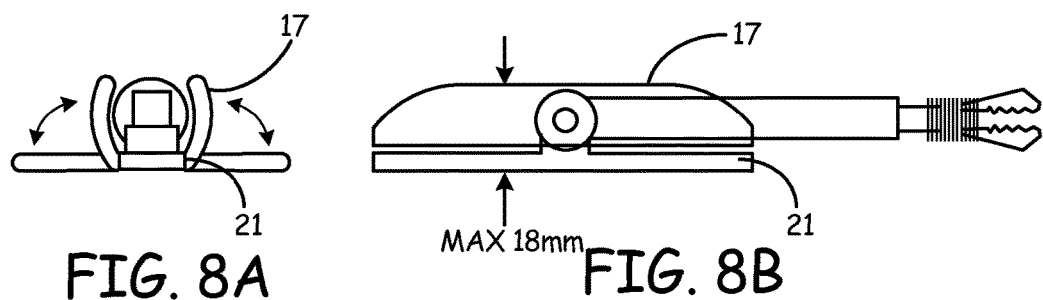
FIG. 8A is an end view and FIG. 8B is a side view of an exemplary foldable enclosure of a micro robotic manipulator.

During an initial state or insertion, the flaps are folded as shown in FIG. 8. Before deployment of the robot arm or end effector, the flaps 17 may be unfolded by a magnetic force triggered from the corresponding electromagnetic location fixing device 1.

The unfolding of the flaps 17 may be triggered by heat of the abdominal wall, by external radiation or by externally supplied power. For example, the base 21 may include a heating device activated by the supply of electrical current or by reception of a radiative energy from a transmitter included in the electromagnetic location fixing device 1. During removal from the body the flaps 17 may refold by cooling. The cooling may be effected by removing the electrical current or transmitted radiation supplied to the heating device and/or separating the manipulator 2 from the abdominal wall. The heating and cooling can also be achieved by other methods such as a thermo-electric heater/cooler, heat pipes, etc. This operation may be reversed with folding being triggered by heating and unfolding being triggered by cooling.

Alternatively or in addition, the flaps 17 may be a laminate of two materials having different coefficients of thermal expansion. Thus, as the flaps 17 are heated and cooled, the materials expand and contract at different rates causing the flaps 17 to fold and unfold. The materials may be metal alloys. The flaps 17 may be constructed from a shape memory alloy.

Alternatively or in addition, following the operation, the flaps 17 may be re-folded by manipulating the flaps 17 using another manipulator.

Alternatively or in addition, the flaps 17 may have a spring effect to assist in opening or closing the flaps and holding the flaps folded. For example, the flaps 17 may have a spring effect with a resultant force that tends to fold the flaps 17. In the presence of the fixing device 1, the spring effect is not strong enough to hold the flaps 17 folded and the flaps 17 are unfolded by the magnetic force. When the fixing device 1 is removed, the spring effect may cause the flaps 17 to fold.

Depending on the condition of the abdominal wall, translation motion of the flaps 17 may be provided by rollers on the flaps 17 (for example as shown by flaps 24 in FIG. 24) that are magnetically switchable or electrically actuatable.

Translation motion of the manipulator 2 may be provided by electromagnetic levitation. For example, the attractive force between the manipulator 2 and the electromagnetic location fixing device 1 may be lessened or reversed to permit movement with respect to the abdominal wall. The electromagnetic location fixing device 1 may then be moved on the abdominal wall by a servo or magnetic transport (similar to the electromagnetic fixing device 26 and base 25 shown in FIG. 24).

In the case of magnetic transport, magnets may be provided in the electromagnetic location fixing device 1. An externally supplied magnetic field is supplied to interact with the magnets of the electromagnetic location fixing device 1 or 26 to cause the electromagnetic location fixing device 1 to move in an X-Y direction and be repositioned with respect to the abdominal wall.

Figure 9:
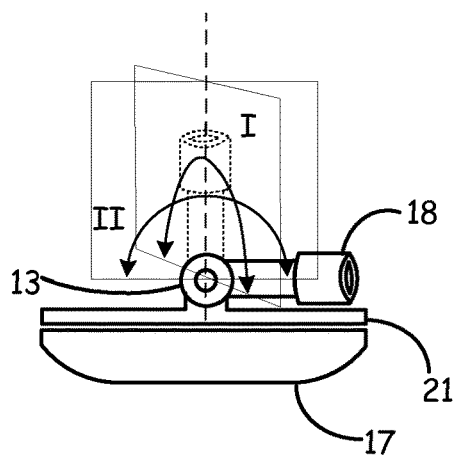
FIG. 9 is a side view showing 2-axis movement of an exemplary 2D micro robotic camera.
Figure 10:
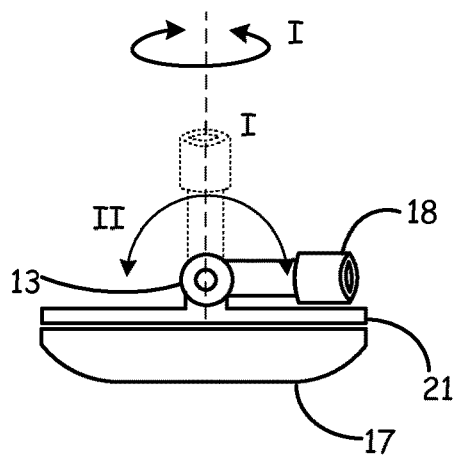
FIG. 10 is a side view showing 2-axis movement of an exemplary 2D micro robotic camera.
Figure 11A:
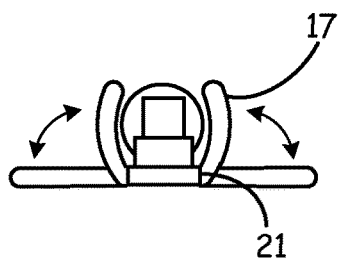
FIG. 11A is an end view and FIG. 11B is a side view of an exemplary foldable enclosure of a micro robotic 2D-camera.
Figure 11B:
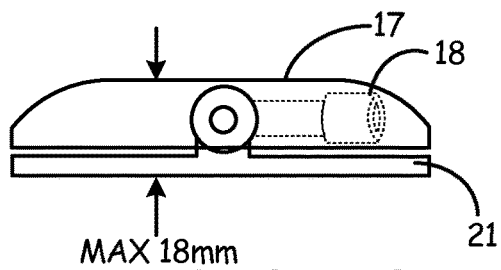
Figure 12:
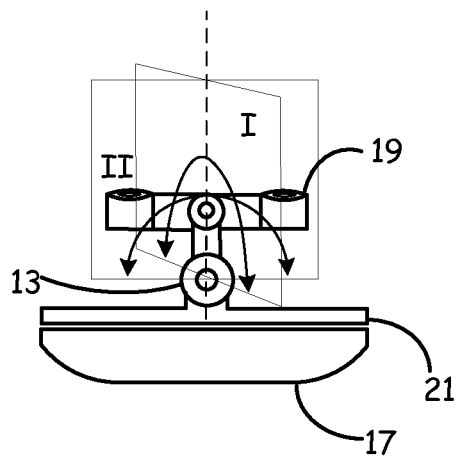
FIG. 12 is a side view showing 2-axis movement of an exemplary 3D micro robotic camera.
Figure 13:
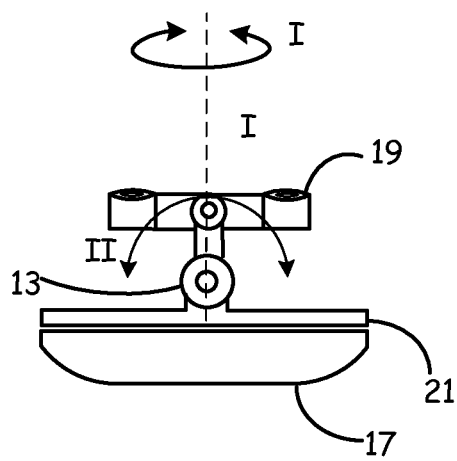
FIG. 13 is a side view showing 2-axis movement of an exemplary 3D micro robotic camera.
Figure 14A:
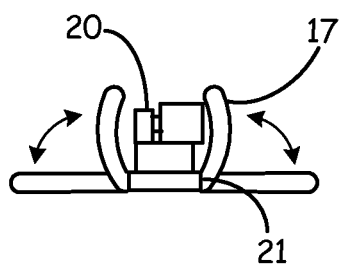
FIG. 14A is an end view and FIG. 14B is a side view of an exemplary foldable enclosure of a micro robotic 3D-camera.
Figure 14B:
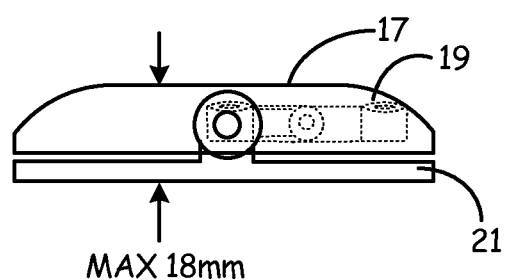

Depending on the purpose of the manipulator during operation, the end effector of the manipulator 2 may be adapted to a gripping device 16, an imaging device, such as a 2D video camera 18 or a 3D stereoscopic video camera 19, or other devices. In the case of a 2D or 3D camera, the camera may rotate along two perpendicular axes to acquire a 2D planar or 3D stereoscopic view in different orientations. Examples of two different types of configurations are shown in FIGS. 9 and 12 (Type A) and FIGS. 10 and 13 (Type B). The enclosure of the camera may facilitate the insertion of the manipulator into the body and protect the 2D camera or 3D camera inside the manipulator during insertion. During initial state or insertion of the 2D or 3D camera, the flaps are folded as shown in FIG. 11 and FIG. 14 respectively. As a non-limiting example, the flaps may have a maximum diameter of 18 mm. A maximum diameter of 18 mm is advantageous as it works well with an entrance port sized for use with most natural orifices. Before deployment of the 2D camera, the flaps 17 are unfolded by a magnetic force triggered from the corresponding remotely controlled electromagnetic location fixing device 1. A spring loaded rotational joint 20 may be included for a 3D camera, as shown in FIG. 14A.

Figure 15:
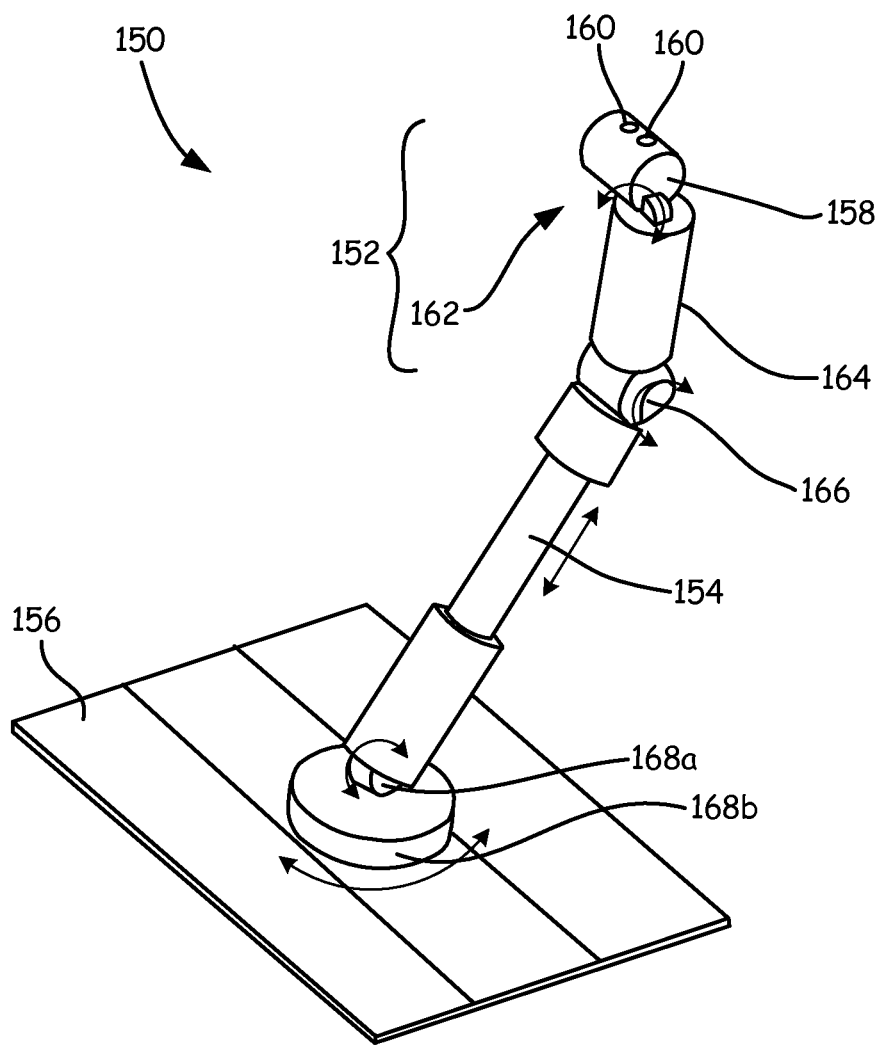
FIG. 15 is a perspective view of an exemplary 3D micro robotic camera.

FIG. 15 is a perspective view of an exemplary 3D camera 150. The camera 150 may include 3 parts: a camera body 152, an extendable linkage bar 154 and a foldable magnetic anchorage 156. The camera body 150 may include a swivel head 158 and two camera lenses 160. The camera lenses 160 may be spaced apart along a major axis of the swivel head 158 and provide a 3D image. The major axis of the swivel head may coincide with a longitudinal axis of the camera 150 in its folded configuration. Spacing the camera lens along the longitudinal axis or "side" accommodates both of the camera lenses 160, thereby providing 3D imagery not otherwise possible, in the limited diameter available in the implantable device. When a forward looking view is needed, the swivel head 158 can swing approximately 90 degrees (or more) to allow the "side" looking cameras to look forward.

A flexible linkage 162, which may be a hinge, is linked to a body part 164, which may be a tube or tube-like control unit. The body part 164 is linked to the extendable linkage bar 154 via a flexible linkage 166, which may be a hinge. The extendable linkage bar 154 extends and retracts to allow positioning of the camera body 152 near to the surgical field. An opposite end of the extendable linkage bar 154 is linked, and in some cases locked, to the foldable magnetic anchorage 156, for example, through a 2-axis flexible linkage 168a and 168b. The flexible linkages 162, 166, 168a and 168b may be servo driven. The foldable magnetic anchorage 156 may be secured on the abdominal/body wall, for example by activating an external magnet or positioning a permanent magnet outside the abdominal wall.

The flexible linkages 162 and 166 allow the camera 150 to bend and position in difficult and confined spaces while being secured by the anchorage 156. The foldable magnetic anchorage 156 may also be swiveled slightly with a center of rotation at the abdominal wall, for example by swiveling the external magnetic anchor, to facilitate slight sideway movement of the camera for clearer vision of an area of interest.

FIG. 16 show an exemplary micro robotic actuator 170 having 7 degrees of freedom and multiple axis of movement provided by the joints 172, 174, 178 and 180.

Additional anchoring force may be provided to the electromagnetic location fixing device 1. For example, for an obese patient with a thick abdominal wall (e.g., 50 mm thick or more), it may be difficult to sufficiently secure the electromagnetic location fixing device 1 to the manipulator 2 for precise motion during a surgical procedure. It is important that a stable platform be provided for secure anchorage of the miniature robots. Also, space available to accommodate the manipulators 2 having a small profile is limited. Thus, providing for external actuation may be desirable to provide sufficient torque for seven full axes of movement in the gripping and moving of organs or tissues during a surgical operation.

Figure 17:
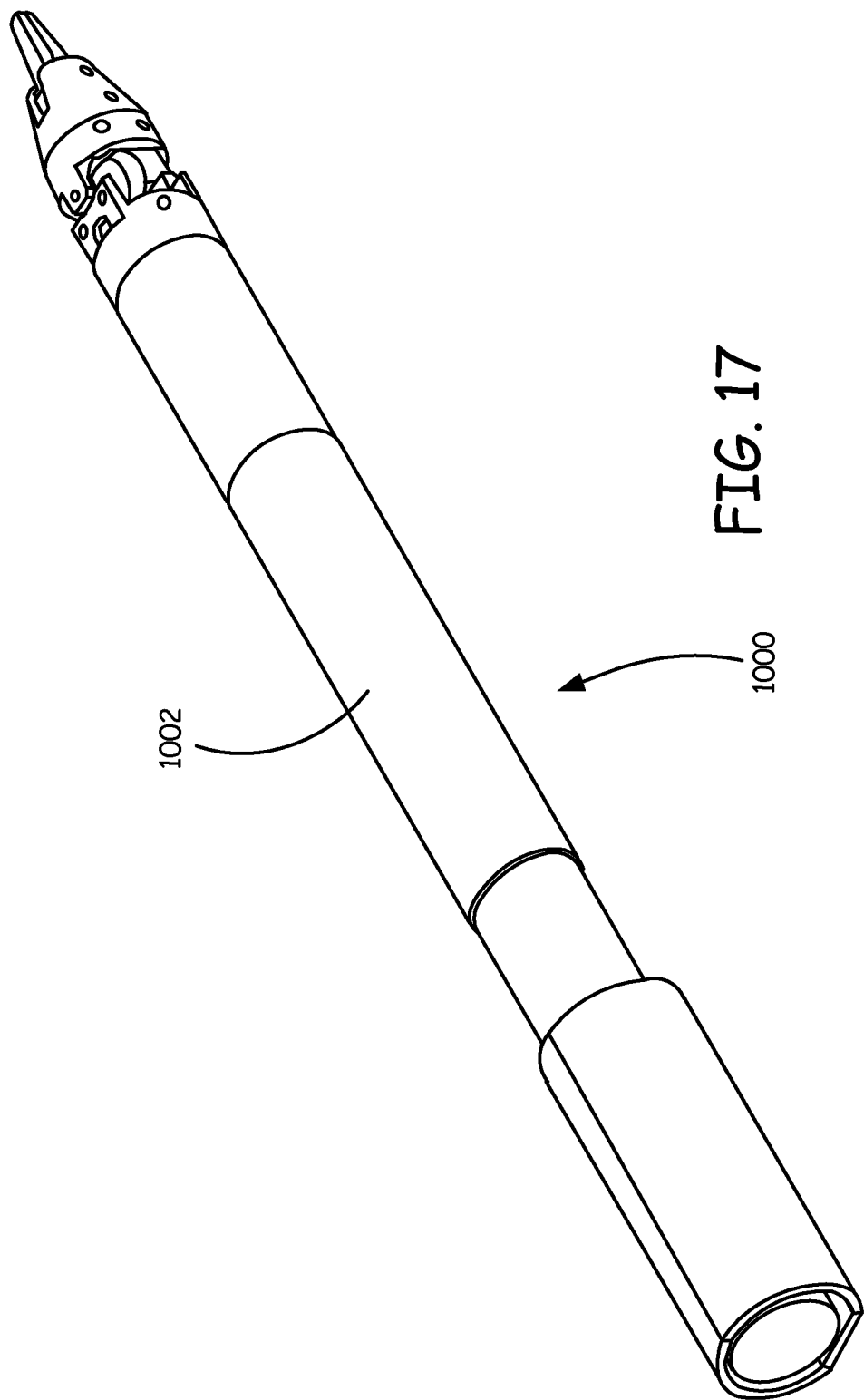
FIG. 17 is a perspective view of an exemplary micro robotic actuator in a folded state.
Figure 18:
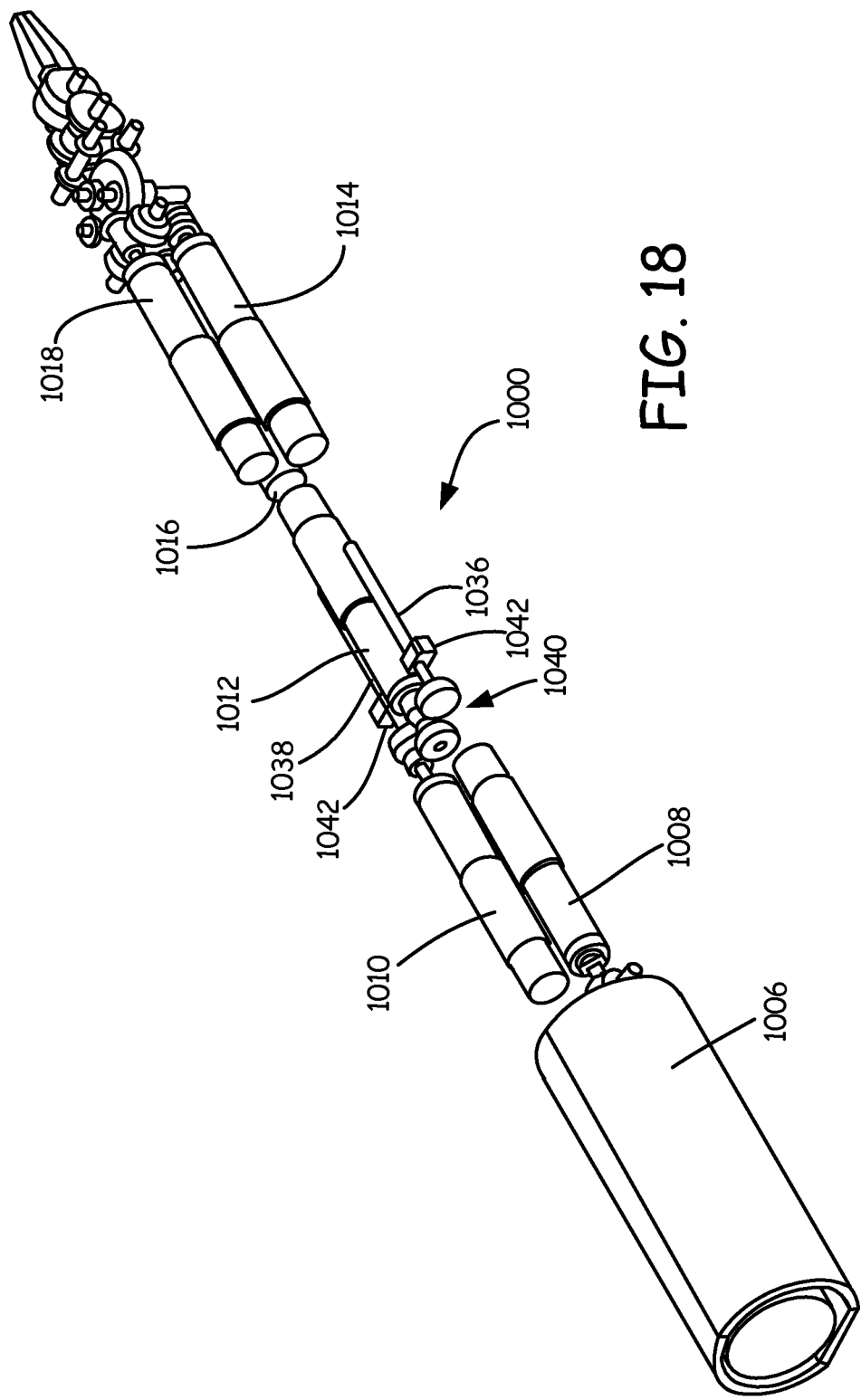
FIG. 18 is a perspective view of an exemplary micro robotic actuator in a folded state with the housing removed.
Figure 19:
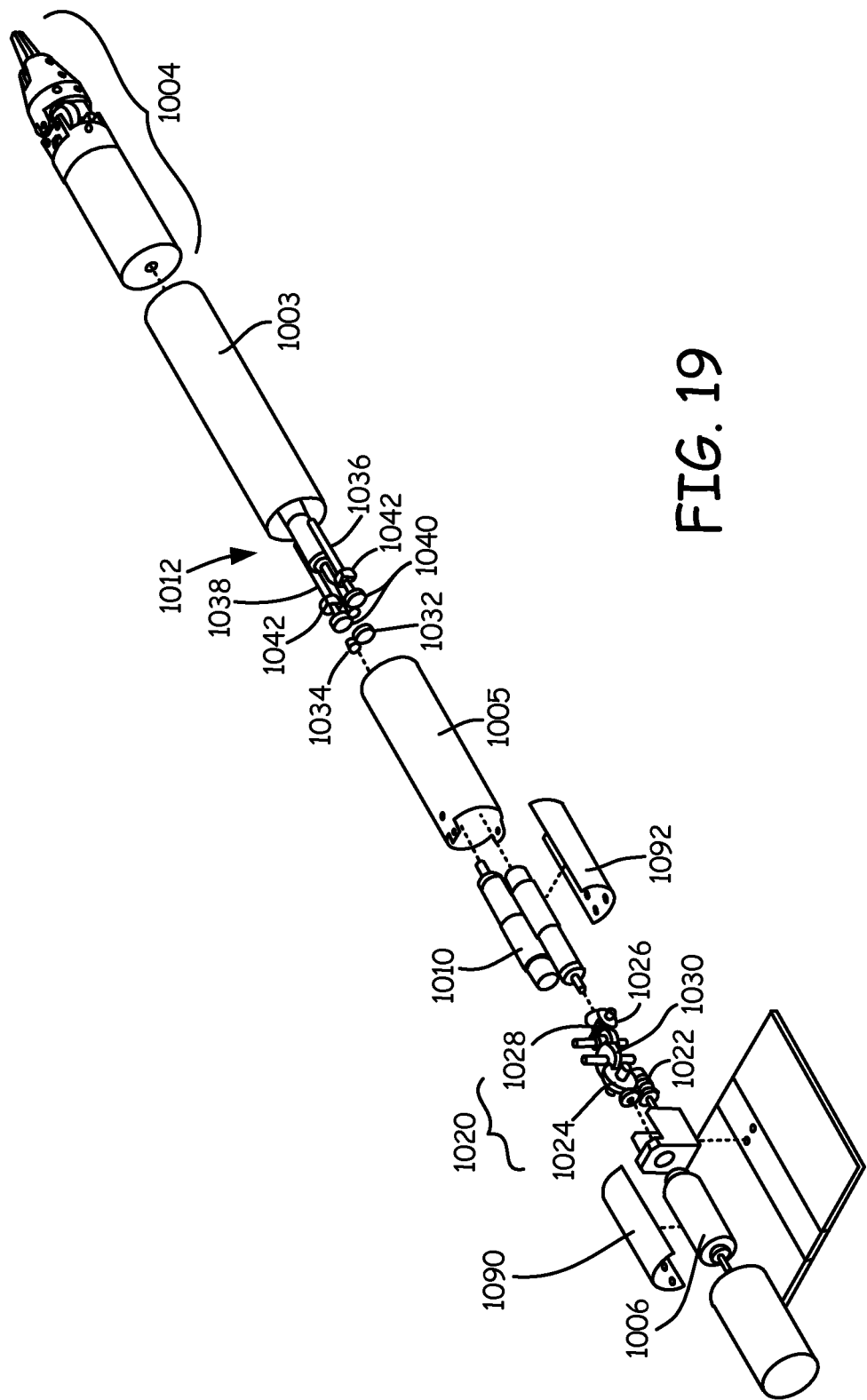
FIG. 19 is an exploded view of an exemplary micro robotic actuator.
Figure 20:
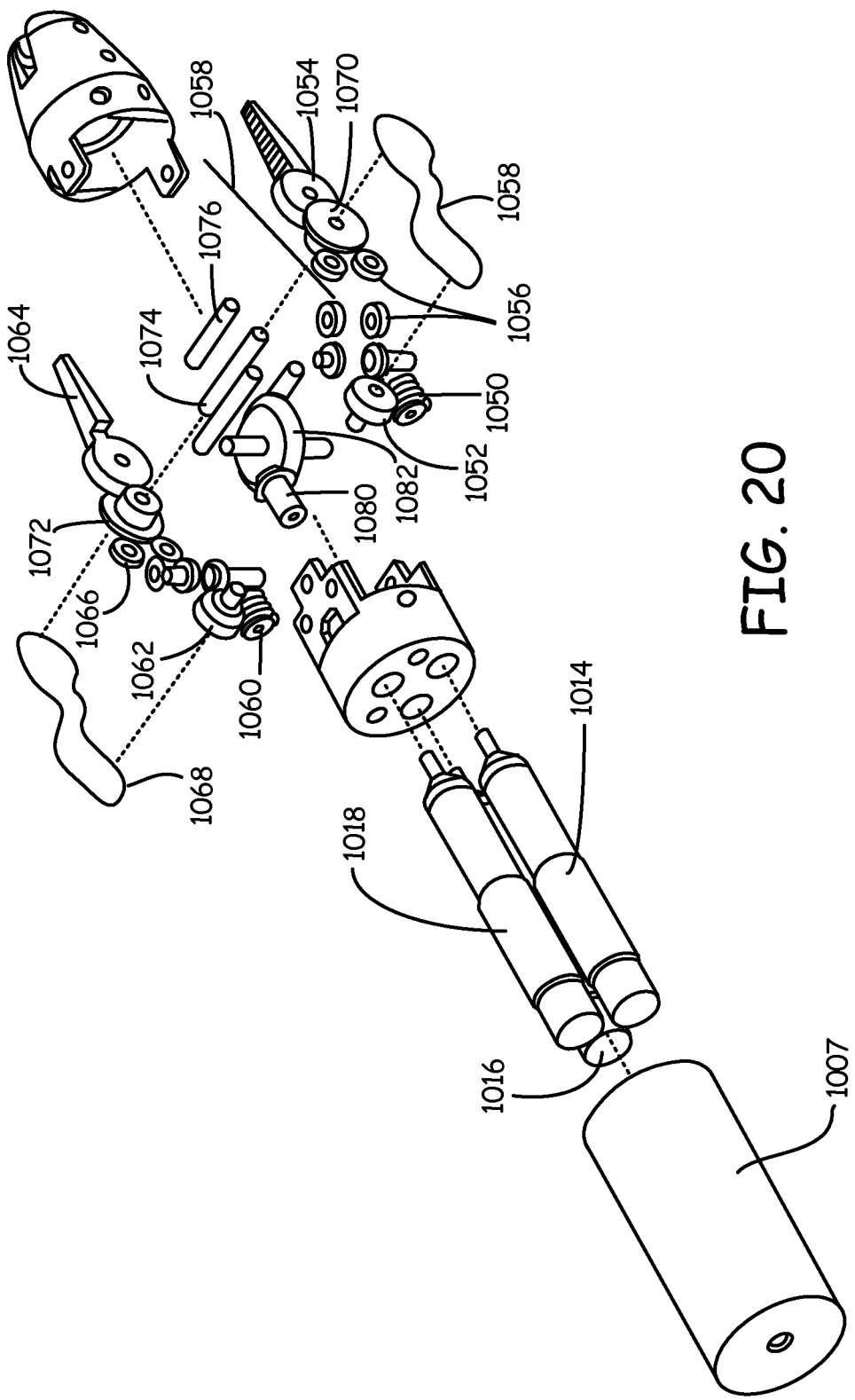
FIG. 20 is an exploded view of an exemplary end effector.
Figure 21:
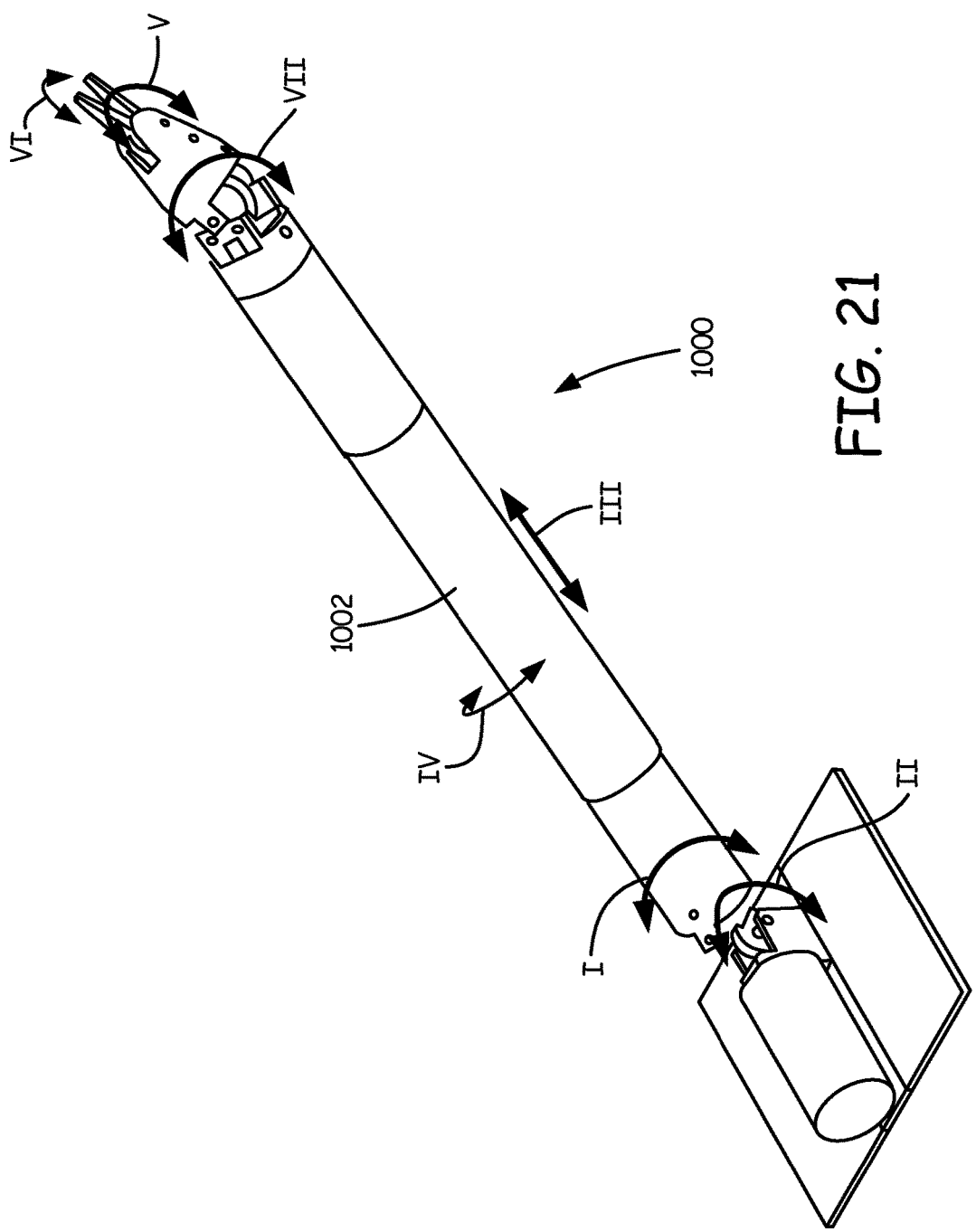
FIG. 21 is a perspective view of an exemplary micro robotic actuator in an unfolded state.
Figure 22:
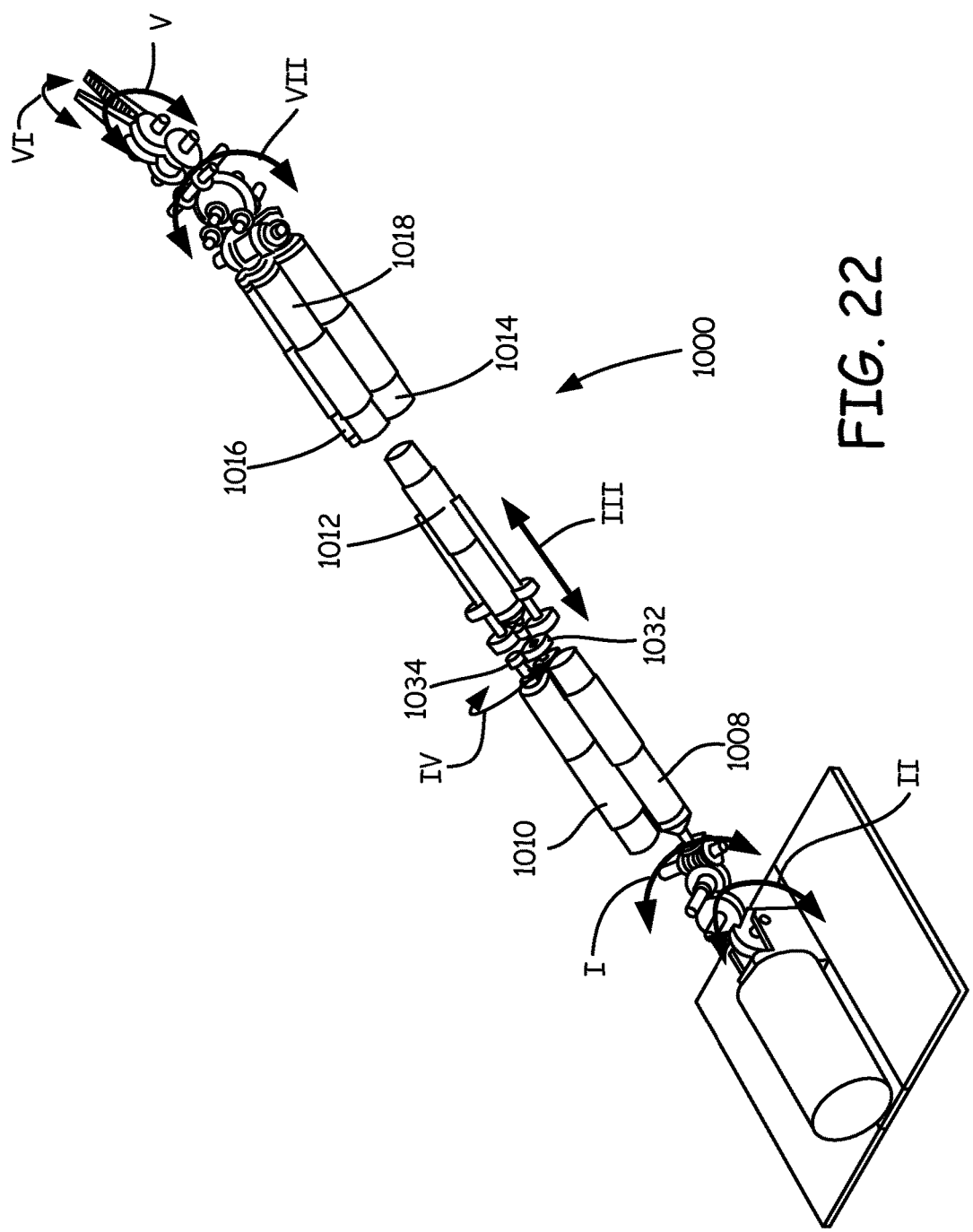
FIG. 22 is a perspective view of an exemplary micro robotic actuator in an unfolded state with the housing removed.

FIG. 17 shows an exemplary micro robotic actuator 1000 in a folded state including the housing 1002. FIG. 18 shows the exemplary micro robotic actuator 1000 in a folded state without the housing 1002. FIG. 19 shows an exploded view of the micro robotic actuator 1000. FIG. 20 shows an exploded view of the end effector 1004 of the micro robotic actuator 1000. FIG. 21 shows the micro robotic actuator 1000 in an unfolded state. FIG. 22 shows the micro robotic actuator 1000 in an unfolded state without the housing 1002. The following discussion refers to FIGS. 17-22 generically unless otherwise noted.

The micro robotic actuator 1000 includes the actuator/motors 1006, 1008, 1010, 1012, 1014, 1016 and 1018. The actuator/motors 1006, 1008, 1010, 1012, 1014, 1016 and 1018 provide in-vivo generation of force for the degrees of freedom (for example, seven) in an overall package size suitable for easy insertion into the human body through a single entrance port. For example, the micro robotic actuator 1000 in a folded configuration may be generally cylindrical with a diameter of 18 mm or less and a length of 200 mm or less.

Figure 16A:
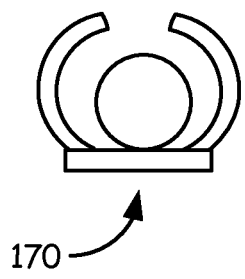
FIG. 16A is an end view of an exemplary micro robotic actuator in a folded configuration.
Figure 16B:
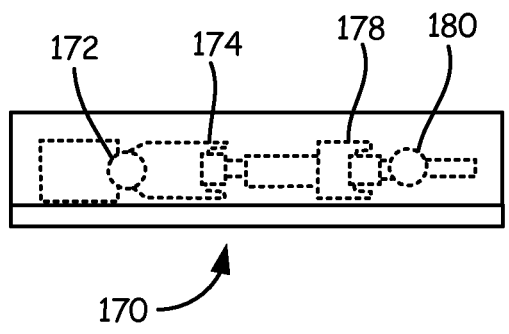
FIG. 16B is a side view of an exemplary micro robotic actuator in a folded configuration.
Figure 16C:
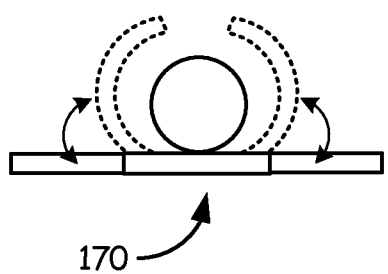
FIG. 16C is an end view of an exemplary micro robotic actuator in an unfolded configuration.
Figure 16D:
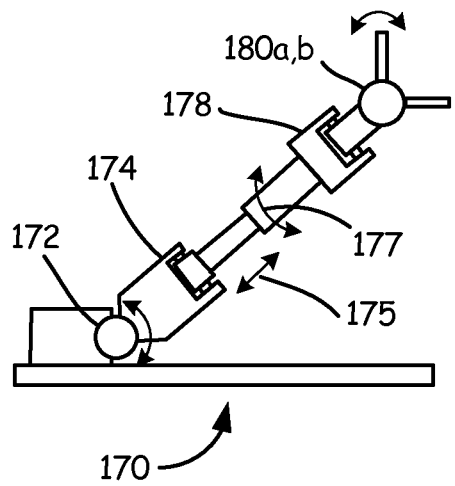
FIG. 16D is a side view of an exemplary micro robotic actuator in an unfolded configuration.

In the exemplary micro robotic actuator 1000 and also with reference to FIGS. 16B and 16D, the actuator/motor 1006 may provide rotation about the axis II at the joint 172; the actuator/motor 1008 may provide rotation about the axis I at the joint 174; actuator/motor 1010 may provide rotation about the axis IV at the joint 177; actuator/motor 1012 may provide extension and retraction along the axis III at the joint 175; actuator/motor 1014 may provide gripping action along the axis V at the joint 180a; the actuator/motor 1016 may provide gripping action along the axis VI at the joint 180b; and the actuator/motor 1018 may provide rotation about the axis VII at the joint 178.

For example, DC servomotors coupled with planetary gearboxes, spur gears and 90 degree intersecting worm gears may be installed at joints 172 and 174 near the manipulator base. Providing the servomotors near the joints allows for greater forces to be generated. For example, two motors may be located near the base of the micro robotic actuator to provide movement about two degrees of motion at the base, one motor may be proved at a central portion of the micro robotic actuator to provide extension/retraction and three motors may be located distal to the two base motors and proximal to the end effector to provide movement about three degrees of motion at the manipulator end of the micro robotic actuator.

In some examples, 1-2 Nm torque for loading force along axis I and II may be generated. Gripping forces for forceps and needle drivers approximately ~10 N and ~20 N respectively may be generated by a combination of piezoelectric actuators and miniature DC servomotors installed in the vicinity of joints 178 and 180. This torque and force is sufficient to perform various manipulations required by surgical operations. The extension and rotation of the manipulator may be controlled by the piezoelectric actuators and DC servomotors installed at joints 175 and 177 respectively.

The actuator/motor 1006 may be coupled to the actuator/motor 1008 via the gear assembly 1020. The gear assembly 1020 may include a worm gear 1022 coupled to the actuator/motor 1006 and the gear 1024. Rotation of the actuator/motor 1006 output may then provide rotation about the gear 1024 to provide the rotation about the axis II at the joint 172. The gear assembly 1020 may also include a worm gear 1028 coupled to the actuator/motor 1006 and the gear 1028. Rotation of the actuator/motor 1008 output may then provide rotation about the gear 1026 to provide the rotation about the axis I at the joint 174. The gear 1024 and the gear 1028 may be coupled via the gear 1030 that may be secured to the housing 1002. The use of a 90 degree intersecting gears 1024 and 1030 is a simple, compact and light weight way to provide X-Y swing movement along the axes I and II directions. The integrated worm and wheel mechanism may provide increased torque (e.g., 1-2 Nm) about the axes I and II.

The actuator/motors 1008 and 1010 may be fixed together directly or via the housing 1002. The output of the actuator/motor 1010 may be coupled to the gear 1032, which may be secured to the housing 1002, to provide the rotation about the axis IV at the joint 177.

The actuator/motor 1012 may be coupled to the threaded rods 1036 and 1038 via the gear system 1040. The carriers 1042 may be fixed to the portion 1003 of the housing 1002. As the output of the actuator/motor 1012 rotates, the carriers 1042, which are fixed to the portion 1003, travel along the threaded rods 1036 and 1038 thereby causing the portions 1003 and 1005 of the housing 1002 to extend or retract with respect to each other.

In some examples, the actuator/motor 1012 may be in the form of a DC servo motor or several piezo-electric motors along the circumference of the robot arm. In such an example, the threaded rods 1036 and 1038 may not be included.

The actuator/motor 1014 may be coupled to the worm gear 1050. The worm gear 1050 may be coupled to the gear 1052, which is coupled to the manipulator end 1054 via a pulley system 1056 that includes the wire or belt 1058. The actuator/motor 1016 may be coupled to the worm gear 1060. The worm gear 1060 may be coupled to the gear 1062, which is coupled to the manipulator end 1064 via a pulley system 1066 that includes the wire or belt 1068. The pulley systems 1056 and 1066 end at the pulleys 1070 and 1072 respectively that share the common shaft 1074. The pulleys 1070 and 1072 are free to rotate about the common shaft 1074 individually. The pulleys 1070 and 1072 may be coupled to the manipulator ends 1054 and 1064 via gear teeth allowing for rotation of the manipulator ends 1054 and 1064 about the common shaft 1076 to provide the gripping action along the axes V and VI at the joints 180*a* and 180*b*.

The gears 1052 and 1062 may be planetary gearboxes to provide a speed reduction and force multiplication of the output of the actuator/motors 1014 and 1016. The flexibility in the pulley systems 1056 and 1066 coupled to the planetary gear boxes provide mechanical advantage as well as freedom of movement. The final connection to the manipulator ends 1054 and 1064 may be geared to increase gripping force at the tip of the manipulator. The gear ratios of the planetary gear boxes and the gearing at the manipulator ends may be different. Also, the use of dual worm gears (1050 and 1060) and dual actuator/motors (1014 and 1016) allows for increased torque at minimum distance. Thus, increased gripping forces such as 10-20 N can be realized.

The actuator/motor 1018 may be coupled to the gear 1080, which is coupled to the gear 1082. The gear 1082 may be secured to the portion 1007 of the housing 1002 to provide rotation about the axis VII at the joint 178. The gear 1080 may be beveled and intersect with the gear 1082 at an approximately ninety degree angle.

The micro robotic actuator 1000 may include the circuit boards 1090 and 1092. The circuit boards 1090 and 1092 may be flexible (e.g., flexible PCB circuitry) to conform to the shape of the housing 1002, such as a cylinder and may be disposed along an inner wall of the housing 1002. The circuit boards 1090 and 1092 may include driver electronics and/or integrated networking capability. Including the driver electronics and/or integrated networking capability within the micro robotic actuator 1000 allows for the reduction of external cabling to fewer conductors in a wire bundle or fewer wire bundles overall.

Figure 25:
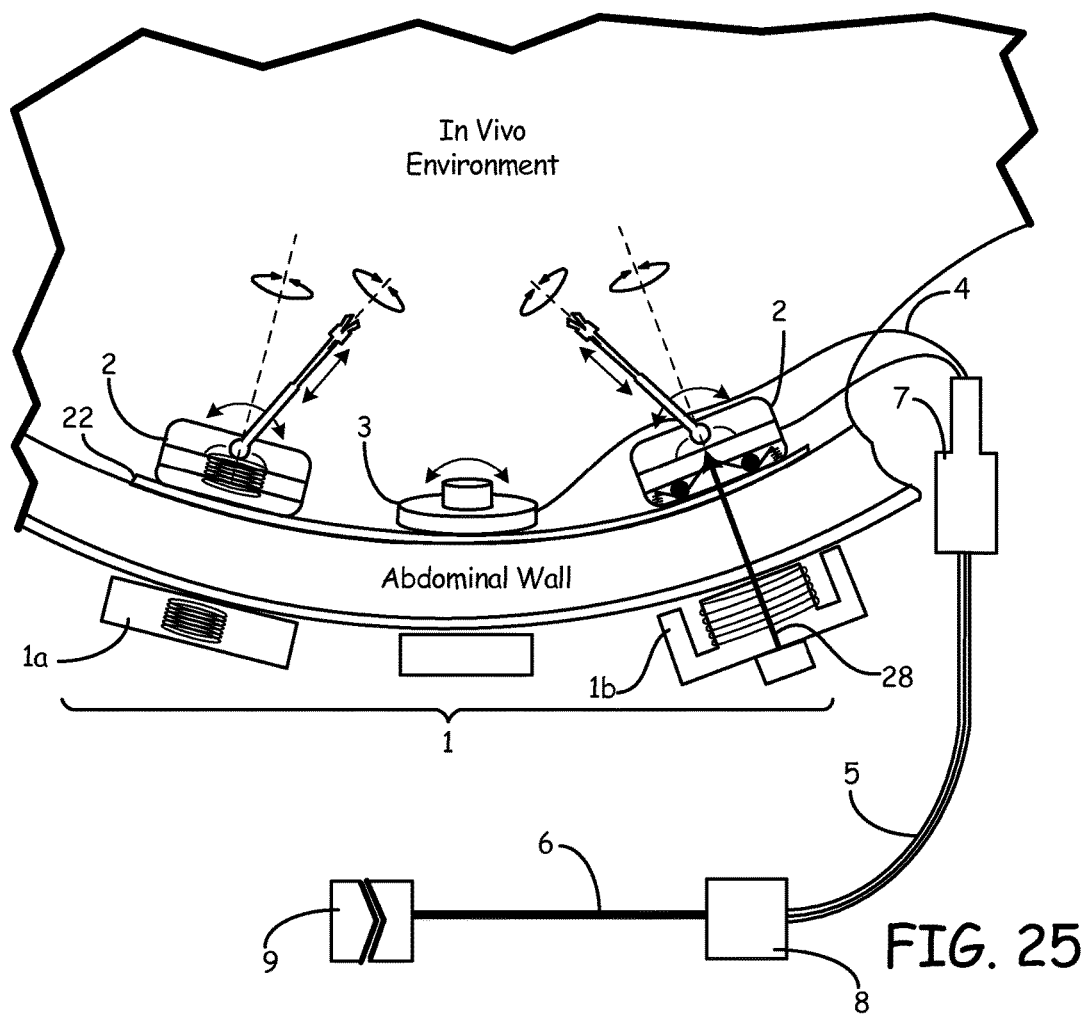
FIG. 25 is a schematic view of an exemplary surgical robotic system including a fine metal wire.
Figure 26A:
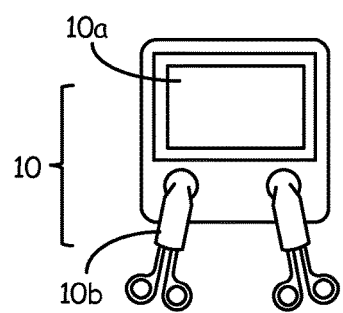
FIGS. 26A and 26B are front views of exemplary human machine interfaces.
Figure 26B:
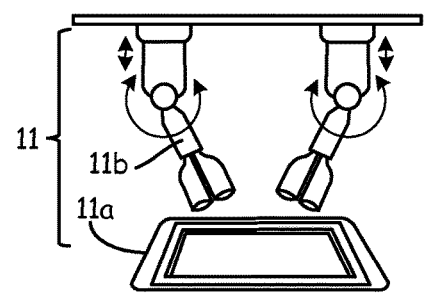
Figure 27:
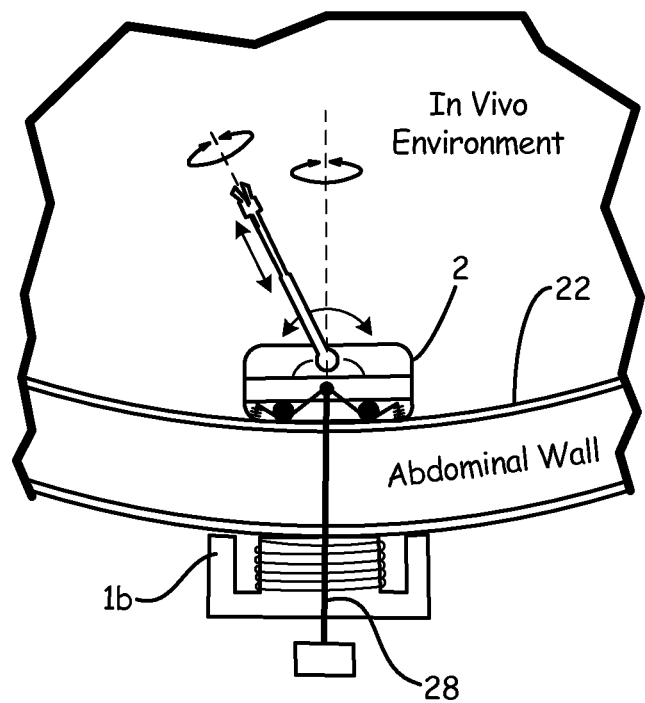
FIG. 27 is a side view showing insertion of an exemplary fine metal wire.

Referring to FIGS. 25-27, a flexible or semi-flexible magnetic sheet 22 can be inserted into the body cavity through the entrance port 7. When inserted, the magnetic sheet 22 may be rolled or folded. Once inserted, it can be unfolded or unrolled and positioned along the abdominal wall. The magnetic sheet 22 may be unfolded/unrolled by a mechanical mechanism or it may be unfolded/unrolled by subjecting it to a magnetic field, which may be supplied by an external electromagnet, and/or by heating or cooling through supplied energy.

The magnetic sheet 22 may be provided as a single large sheet sufficient to cover a large area of the inner abdominal wall. The magnetic sheet may also be provided by one or more small or medium sized sheets to provide coverage for a certain region of the abdominal wall.

Figure 34:
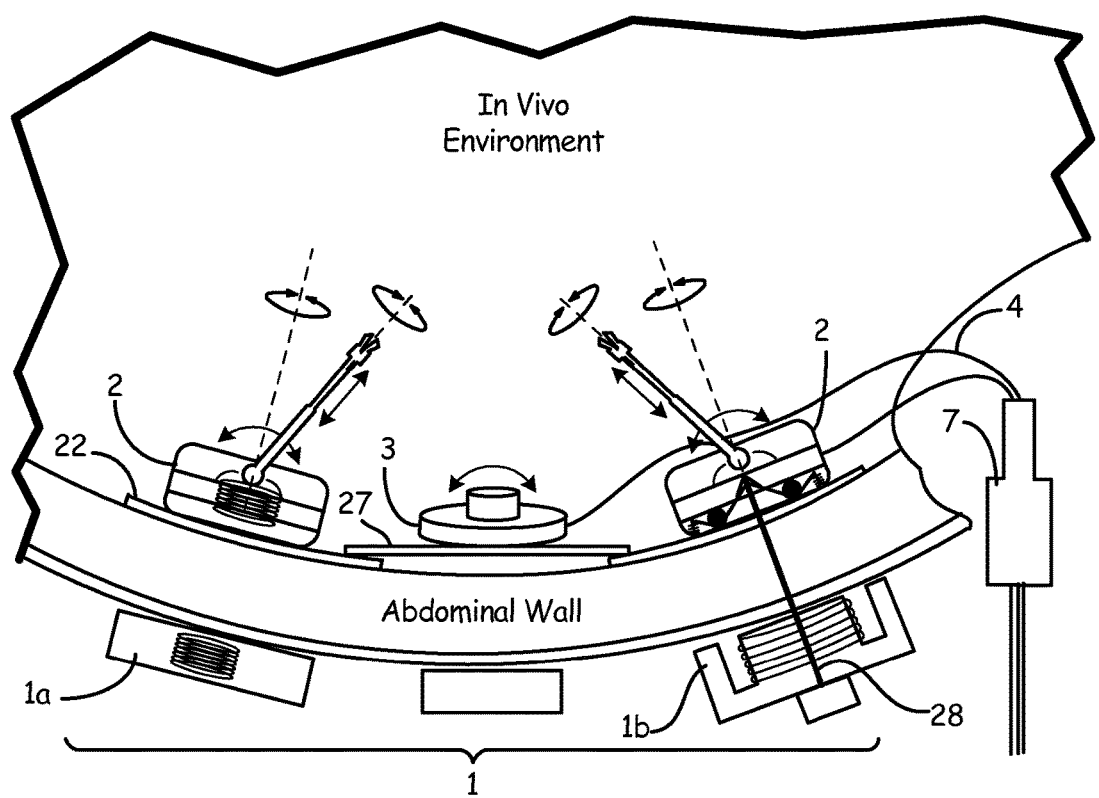
FIG. 34 is side view of an exemplary intra abdominal mechanical frame.

An intra abdominal mechanical frame, for example the intra abdominal mechanical frame 27 shown in FIG. 34, may be constructed by linking individual magnetic sheets with extendable bars to provide a stable platform for the miniature robots to operate. This intra abdominal mechanical frame may, in some cases, provide anchoring support similar to that of a large flexible magnetic sheet covering a large part of the abdomen without requiring the use of such a large sheet.

The position of the magnetic sheet 22 may be fixed by the external electromagnet 1*b*. The magnetic sheet 22 provides a stable platform for the micro robotic manipulator 2 to attach to. The magnetic sheet 22 may provide a medium to concentrate magnetic flux and provide for the secure anchorage of micro robotic manipulators such as the micro robotic manipulator 2. Exemplary materials that provide such a medium to concentrate flux include iron and silicon-iron based materials. It will be appreciated that this secure anchorage can be provided for any micro robotic manipulator as well as other related devices such as a camera. It will also be appreciated that the magnetic sheet may be used with, but is not required for, any of the described examples including those of FIGS. 1 and 23-34.

To provide additional anchorage force, a fine wire 28 may be included. The fine wire 28, which may be a metal wire, extends from the external electromagnet 1*b* and may be introduced through the abdominal wall via, or in the form of, a fine needle. To facilitate introduction of the fine metal wire 28 via a needle or hypodermic syringe, the wire 28 may have a maximum diameter of 1 mm. A maximum diameter of 1 mm is preferable so that punctures remain well below a size that would be regarded an incision and leave no significant visible scarring. It will be appreciated that other materials such as flexible or rigid fibers, biocompatible polymers/plastics and multi-material composites that may or may not include a metal may be used in place of metal for the wire 28.

As an example, the fine metal wire 28 may be provided from the external electromagnet 1*b* via a circular through hole, a slot, or another aperture in the electromagnet 1*b*. The hole, slot or other aperture may be provided at a center of the electromagnet 1*b*.

A locking mechanism, such as a pair of inclined metal tabs having a separation less than a thickness of the fine wire 28 or a tip thereof, may be provided to releasably lock the micro manipulator 2 on the tip of the fine wire 28. In the example of a locking mechanism using a metal tab, the metal tab may be subject to a biasing force, such as a spring, to keep the fine wire 28 locked in the micro robotic manipulator 2. Removing the biasing force or providing a counter force may allow the fine wire 28 to be released. The release of the fine wire 28 may be provided by a remote controlled electrical actuator or by mechanical action, for example by an endoscope, inside the abdomen.

Figure 28:
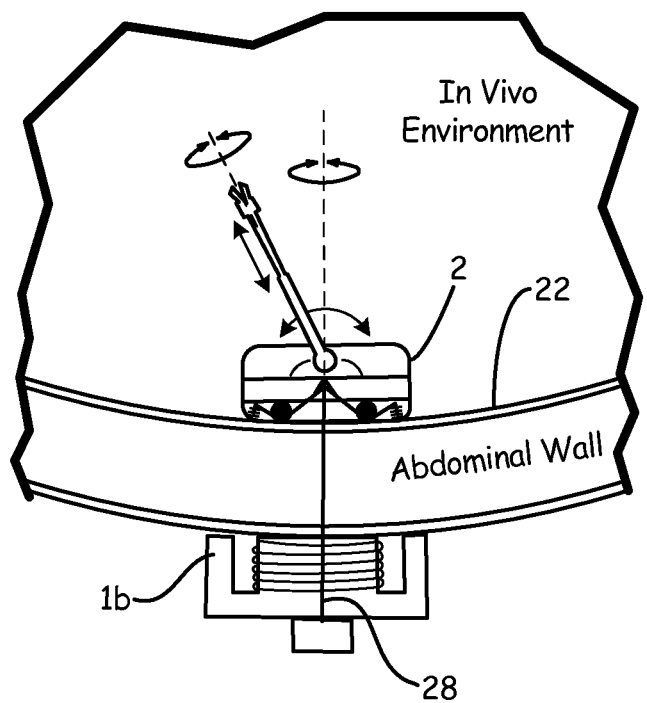
FIG. 28 is a side view showing locking of an exemplary fine metal wire to a miniature robot.

Referring to FIG. 28, the tip of the metal wire 28 may be locked by a releasable non-return mechanism. The tip of the fine wire 28 may be enlarged to provide a more secure lock.

Figure 29:
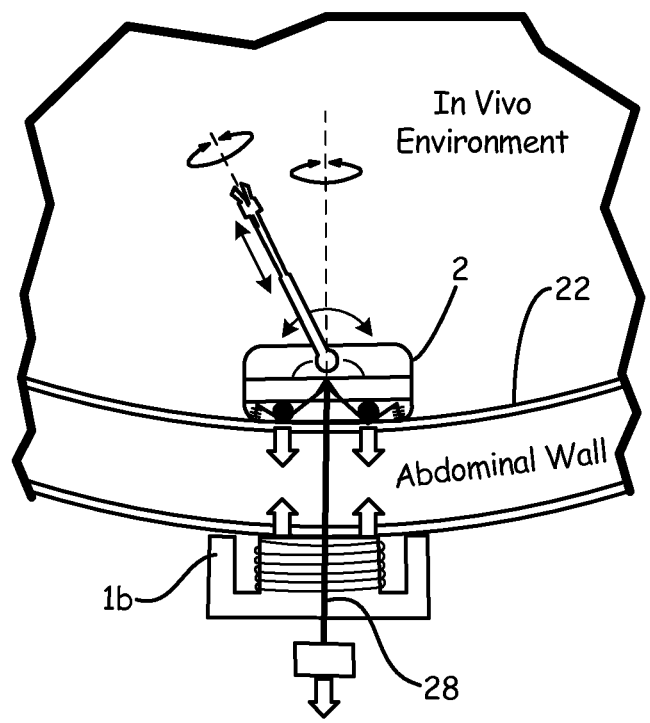
FIG. 29 is a side view showing an example of force of tightening by a fine metal wire.
Figure 30:
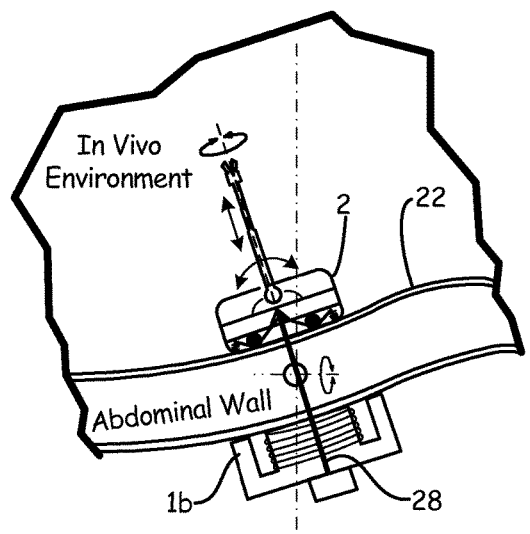
FIG. 30 is a side view showing exemplary X-Y movement of a micro robotic manipulator to the left with a fine metal wire.
Figure 31:
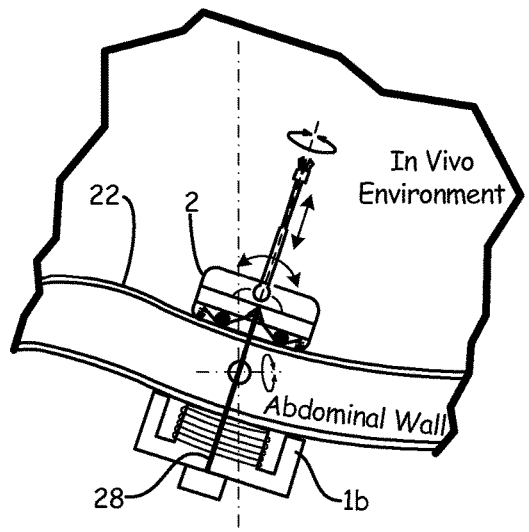
FIG. 31 is a side view showing exemplary X-Y movement of a micro robotic manipulator to the right with a fine metal wire.
Figure 32:
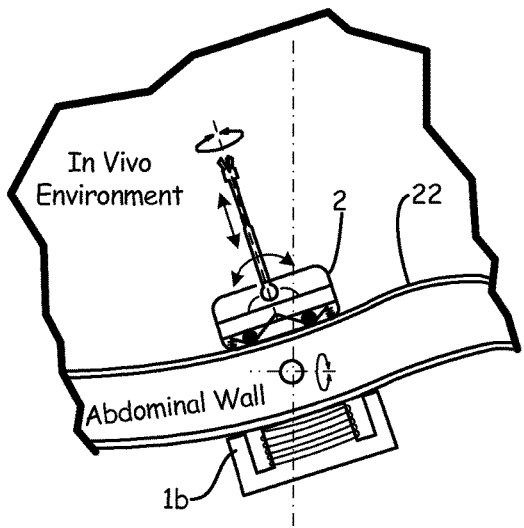
FIG. 32 is a side view showing exemplary X-Y movement of a micro robotic manipulator to the left without a fine metal wire.
Figure 33:
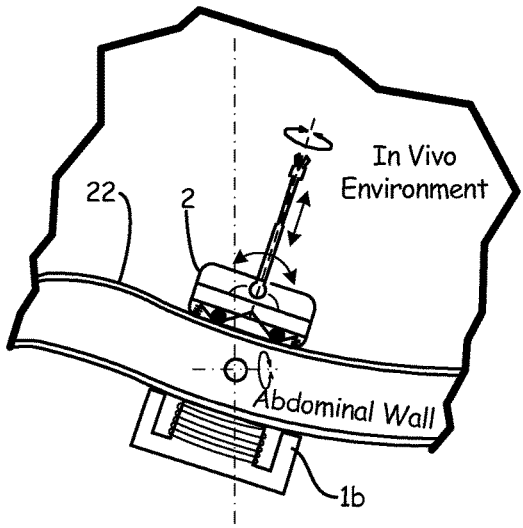
FIG. 33 is a side view showing exemplary X-Y movement of a micro robotic manipulator to the right without a fine metal wire.

Referring to FIG. 29, when the fine wire 28 is tightened at the base of the external electromagnet 1*b*, the external electromagnet 1*b* and the miniature robot 2 are pressed against the abdominal wall from opposite sides such that an additional locking force is provided for the micro robotic manipulator 2 to attach to the stable platform. Therefore, secure and stable movements of the micro robotic manipulator 2 are provided in carrying out the surgical operation.

An aperture may be provided in the external electromagnet 1*b* through which the fine wire 28 passes. The aperture may be in the form of a slot, a cross, a large singular opening, or another shape. Providing the aperture allows for the relocation of the micro robotic manipulator 2 after the fine wire 28 has been inserted in the abdominal wall without requiring a reinsertion of the fine wire 28. Thus, the wire may be loosened allowing the movement of the external electromagnet 1*b* and the micro robotic manipulator 2 and subsequently retightened to allow for the repositioning of the micro robotic manipulator 2.

In addition to providing additional anchorage force, the fine wire 28 may also be used to supply power or signals to/from the micro robotic manipulator 2.

Referring to FIGS. 30-33, when the miniature robot is tightly coupled to the electromagnet, movement of the micro robotic manipulator 2 may be induced by the swivel action of external electromagnet 1b. For example, the center of movement may be located at the midpoint of the abdominal wall.

The external actuation can supplement the X-Y movement of micro-actuator on the micro robotic manipulator 2. Due to the leverage effect, a small angular movement of the electromagnet 1b will lead to a large two dimensional X-Y movement of the micro robotic manipulator 2. Without the tight coupling, attempts to move the micro robotic manipulator 2 in this manner would likely result in separation of the micro robotic manipulator 2 and the external electromagnet 1b and X-Y movement would not be achieved.

Referring now to at least FIGS. 35 to 43, an example embodiment of a magnetic-anchored robotic system (MRS) (hereinafter referred to as a "surgical system"), may comprise an internal anchor assembly configurable to be inserted into and positioned inside a cavity of a body. The surgical system may further comprise an external anchor assembly configurable to magnetically couple to the internal anchor assembly. The external anchor assembly may include a magnetic assembly having one or more superconducting magnets configurable to generate a magnetic field and a conductive housing for receiving the one or more superconducting magnets. The external anchor assembly may further include a temperature control section configurable to control a temperature of the one or more superconducting magnets via the conductive housing. The temperature control section may include a cryo-cooler assembly and one or more heat rods, and may also include conductive housing for the one or more superconducting magnets. The external anchor assembly may further include an external anchor body configurable to receive the magnetic assembly and the temperature control section, the external anchor body fixed in position outside of the body. The external anchor assembly may be configurable to selectively vary the magnetic field applied to the internal anchor assembly. For example, when the external anchor assembly magnetically couples to the internal anchor assembly, and when the magnetic assembly is magnetically coupled to the internal anchor assembly at a first separation distance from the internal anchor assembly, the external anchor assembly may be configurable to vary the magnitude of the magnetic field applied to the internal anchor assembly by varying the first separation distance. In this regard, the external anchor assembly may further comprise a support structure, the support structure selectively configurable to position the external anchor body outside of the body, and the magnetic field applied at the internal anchor assembly may be reduced or increased by selectively configuring the support structure to increase or reduce, respectively, the first separation distance. The surgical system may further comprise an intermediary member positioned between the external anchor assembly and the internal anchor assembly, wherein the first separation distance may be varied by selectively varying a dimension of the intermediary member. The external anchor assembly may also be configurable to selectively vary the generated magnetic field (i.e., generated by the one or more superconducting magnets). For example, the external anchor assembly may be configurable to selectively vary the generated magnetic field by varying a temperature of the one or more superconducting magnets. Furthermore, the external anchor assembly may be configurable to selectively diminish the generated magnetic field by increasing the temperature of the one or more superconducting magnets to be equal to or greater than a critical temperature. In respect to the one or more superconducting magnets, the magnetic assembly may comprise a plurality of superconducting magnets configured in one or more vertically stacked arrangements. The surgical system may further comprise an instrument assembly having an instrument at a first end and an instrument assembly attaching section at a second end, and the instrument assembly may be configurable to secure to the internal anchor assembly by securing an instrument assembly attaching section of the instrument assembly to the internal anchor attaching section of the internal anchor assembly. The surgical system may further comprise a controller, processor, or the like, configurable to configure a magnitude of the magnetic field applied, by the magnetic assembly, at the internal anchor assembly. This may be achieved, for example, by controlling or configuring a temperature of the one or more superconducting magnets, such as via the temperature control section (which may include one or more of the cryo-cooler assembly, one or more heat rods, a heater, and may also include the conductive housing for the one or more superconducting magnets).

Still referring to FIGS. 35 to 43, an example embodiment of an external anchor assembly for use with a magnetic-anchored robotic system (MRS) (hereinafter also referred to as a "surgical system") having an internal anchor assembly may comprise a magnetic assembly having one or more superconducting magnets configurable to generate a magnetic field and a conductive housing for receiving the one or more superconducting magnets. The external anchor assembly may further comprise a temperature control section configurable to control a temperature of the one or more superconducting magnets via the conductive housing. The external anchor assembly may further comprise an external anchor body configurable to receive the magnetic assembly and the temperature control section, the external anchor body fixed in position outside of the body. The magnetic assembly of the external anchor assembly may be configurable to magnetically couple to the internal anchor assembly via the magnetic field.

Still referring to FIGS. 35 to 43, and in particular, FIGS. 42 and 43, a method of configuring a magnetic-anchored robotic system (MRS) (hereinafter also referred to as a "surgical system") may comprise providing an internal anchor assembly, the internal anchor assembly configured to be inserted into and positioned inside a cavity of a body. The method may further comprise providing an external anchor assembly. The external anchor assembly may include a magnetic assembly having one or more superconducting magnets configurable to generate a magnetic field and a conductive housing for receiving the one or more superconducting magnets. The external anchor assembly may further include a temperature control section having a heat rod and a cryo-cooler, the heat rod in contact with the conductive housing and the cryo-cooler. The external anchor assembly may further include an external anchor body configurable to receive the magnetic assembly and the temperature control section. The method may further include preparing the one or more superconducting magnets by providing a charging field (or magnet) and configuring the cryo-cooler to a first temperature, the first temperature operable to bring a temperature of the one or more superconducting magnets to be lesser than or equal to a second temperature. The preparing of the one or more superconducting magnets may further include bringing the magnetic assembly to the charging field. The preparing of the one or more superconducting magnets may further include ramping up a magnetic field generated by the charging field at a first rate. The preparing of the one or more superconducting magnets may further include configuring the cryo-cooler to a third temperature less than the first temperature, the third temperature operable to bring the temperature of the one or more superconducting magnets to be lesser than or equal to a fourth temperature less than the second temperature. The preparing of the one or more superconducting magnets may further include ramping down the magnetic field generated by the charging field at a second rate. The preparing of the one or more superconducting magnets may further include removing the magnetic assembly from the charging field when the magnetic field generated by the charging field reaches a final magnetic field value. The method may further comprise inserting the internal anchor assembly into a cavity of a body and positioning the internal anchor assembly at an interior surface of the cavity of the body. The method may further comprise, after the preparing of the one or more superconducting magnets, configuring a support structure to position the external anchor assembly at an exterior surface of the body based on the positioning of the internal anchor assembly, and magnetically coupling the external anchor assembly to the internal anchor assembly via a magnetic field generated by the one or more superconducting magnets of the magnetic assembly. The method may further comprise providing an instrument assembly, the instrument assembly having an instrument at a first end and an instrument assembly attaching section at a second end. The method may further comprise inserting the instrument assembly into the cavity of the body. The method may further comprise securing the instrument assembly to the internal anchor assembly by securing an internal anchor attaching section of the internal anchor assembly to the instrument assembly attaching section. The method may further comprise configuring a controller to configure a magnitude of the magnetic field applied, by the magnetic assembly, at the internal anchor assembly. The method may further comprise configuring the controller to configure the temperature control section to control the temperature of the one or more superconducting magnets.

These and other example embodiments of the surgical system will now be further described in more detail below with reference to at least FIGS. 35 to 43.

Figure 35A:
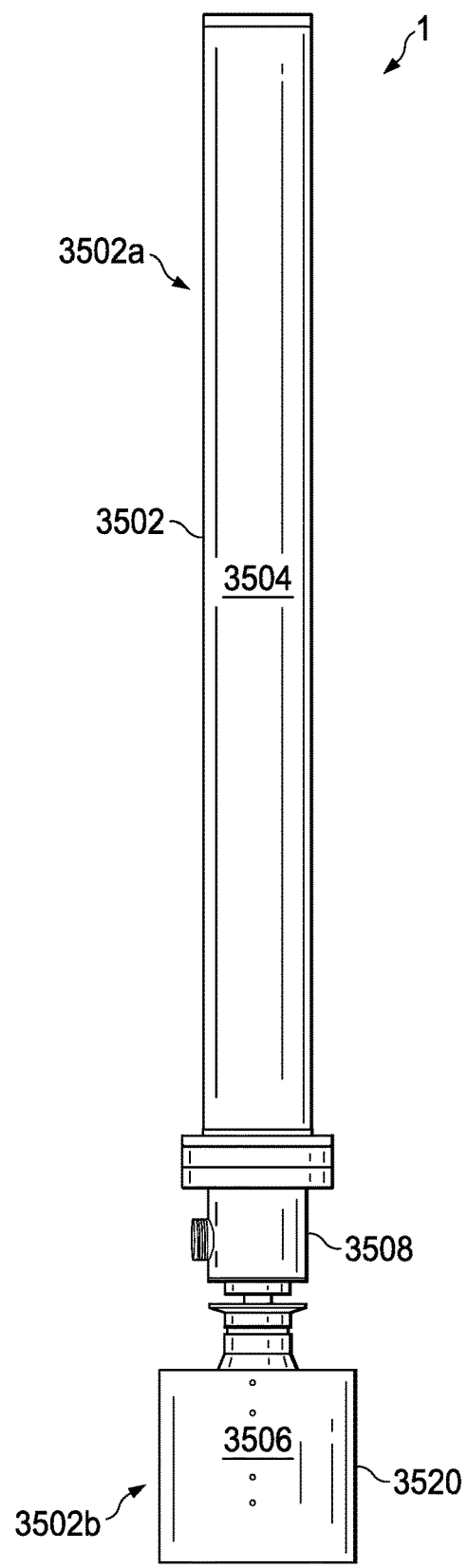
FIG. 35A is a cross-sectional view of an exemplary external anchor assembly.
Figure 35B:
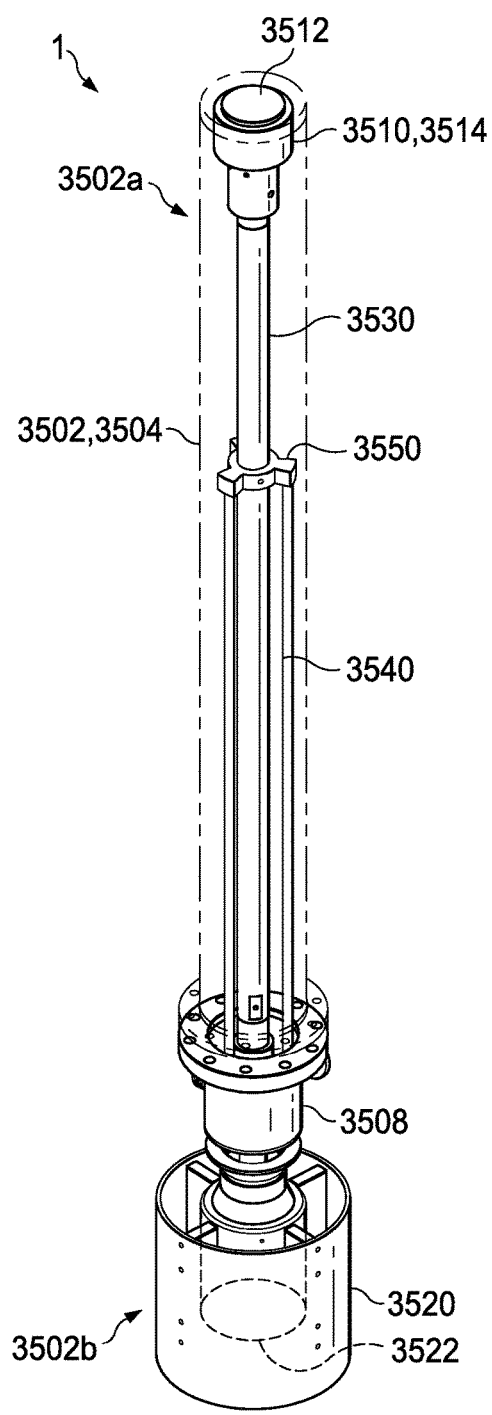
FIG. 35B is a perspective view of an exemplary external anchor assembly.
Figure 35C:
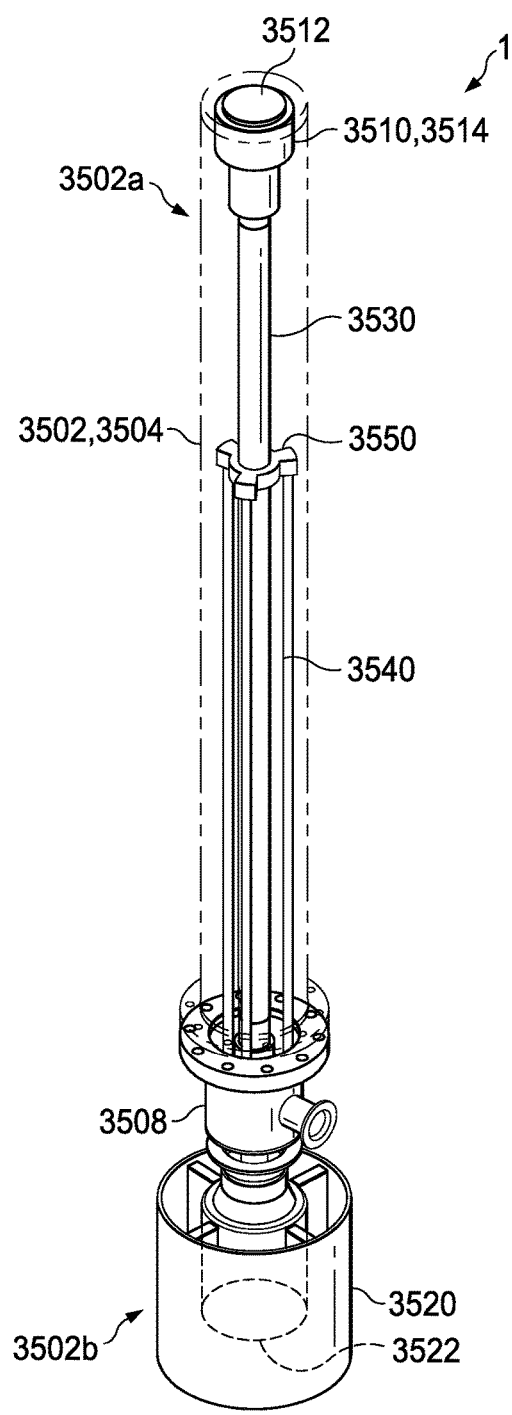
FIG. 35C is another perspective view of an exemplary external anchor assembly.
Figure 35D:
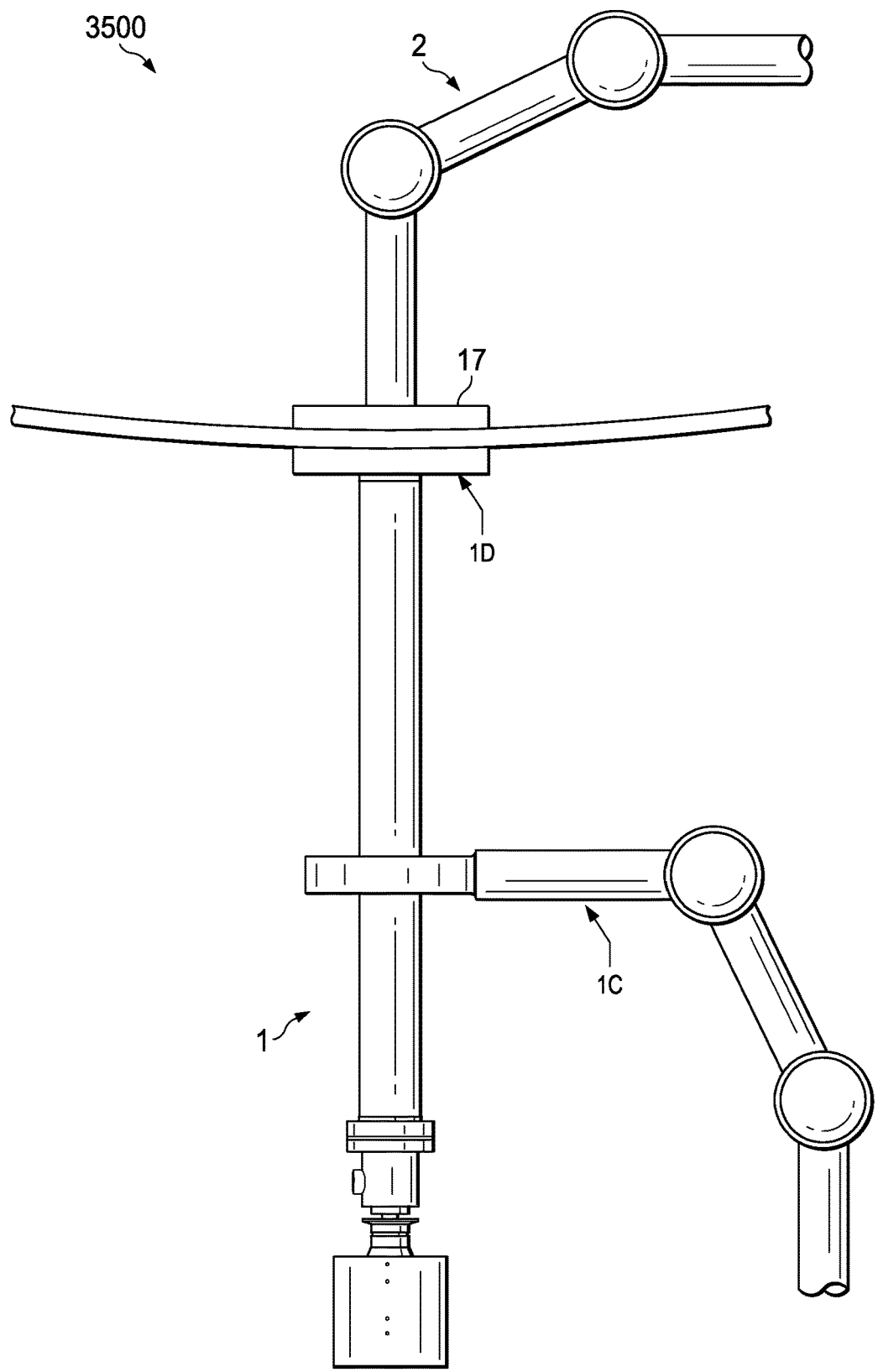
FIG. 35D is a side view of an exemplary system having an exemplary external anchor assembly fixably positioned outside of a body by an exemplary support structure and magnetically coupled to an exemplary internal anchor assembly.

As illustrated in at least FIG. 35A, FIG. 35B, FIG. 35C, and FIG. 35D, an example embodiment of the surgical system 3500, including those described above and in the present disclosure, may comprise an external anchor assembly 1 (e.g., element 1 recited in the present disclosure). Example embodiments may further comprise an internal anchor assembly 17 (e.g., elements 17, 21, 22, and/or 156 recited in the present disclosure), as illustrated in FIG. 35D. Example embodiments may further comprise an instrument assembly 2 (e.g., elements 2, 18, 19, 150, and/or 1000 recited in the present disclosure), as illustrated in at least FIG. 35D. Example embodiments may further comprise a support structure 1c, as illustrated in at least FIG. 35D. The support structure 1c may be a part of the external anchor assembly 1 (e.g., element 1 recited in the present disclosure) and/or a standalone unit. Example embodiments may further comprise an intermediary member 1d, such as an inflatable bladder, or the like, as illustrated in at least FIG. 35D. The intermediary member 1d may be a part of the external anchor assembly 1 (e.g., element 1 recited in the present disclosure) and/or a standalone unit. These elements of the surgical system are further described below with reference to FIGS. 35 to 43.

Internal Anchor Assembly (e.g., Elements 17, 21, 22, and/or 156)

The internal anchor assembly 17 (e.g., elements 17, 21, 22, and/or 156 recited in the present disclosure) may be any internal anchor, or the like, operable to magnetically couple (or magnetically secure) to the external anchor assembly 1 (e.g., element 1 recited in the present disclosure) in example embodiments. For example, the internal anchor assembly 17 may be an anchor comprising ferromagnetic portions that is foldable, bendable, and/or rollable in shape and/or configuration, and may include memory shape alloy.

In example embodiments, the internal anchor assembly 17 may be attached to and/or integrated with the instrument assembly 2. The internal anchor assembly 17 may also be attachable to and removable or detachable from the instrument assembly 2 in example embodiments. In example embodiments wherein the internal anchor assembly 17 is attachable to and removable from the instrument assembly 2, the internal anchor assembly 17 may comprise an internal anchor attaching section and the instrument assembly 2 may comprise an instrument assembly attaching section. In this regard, the instrument assembly 2 may be configurable to secure to the internal anchor assembly 17 by securing the instrument assembly attaching section to at least the internal anchor attaching section.

The internal anchor assembly 17 may be configurable to be inserted into a cavity of a body, such as via entrance port 7 (e.g., element 7, 207', and/or 207" recited in the present disclosure), and positioned inside the cavity of the body, as illustrated in FIG. 35D. The internal anchor assembly 17 may also be configurable to be removed from the cavity of the body, such as via entrance port 7 (e.g., element 7, 207', and/or 207" recited in the present disclosure).

In an example embodiment, the internal anchor assembly 17 may be formed in any one or more of a plurality of shapes, or combinations thereof, including shapes that are square, rectangular, circular, oval, hexagonal, etc. For example, a shape of the internal anchor assembly 17 may be selected based on, among other things, one or more of: a shape of a portion of the external anchor assembly 1, such as end 3502a; a shape of a portion of the magnetic assembly 3510; a shape of a portion of the conductive housing 3514; a shape of the configuration of the one or more superconducting magnets 3512; a shape of a portion of an entrance port 7 (e.g., element 7, 207', and/or 207" recited in the present disclosure); etc.

A width of the internal anchor assembly 17 may be between about 5 mm to 75 mm, a length of the internal anchor assembly 17 may be between about 5 mm to 75 mm, and a thickness of the internal anchor assembly 17 may be between about 0.1 mm to 10 mm. The aforementioned dimensions of the internal anchor assembly 17 may be a maximum dimension, an average dimension, a typical dimension, a minimum dimension, etc.

The internal anchor assembly 17 (e.g., elements 17, 21, 22, and/or 156 recited in the present disclosure), including the internal anchor attaching section, may be formed using any one or more of a plurality of strong ferromagnetic materials in the form of solid blocks, bars, cylinders, and/or powder impregnated resins.

The internal anchor assembly 17 may be operable to magnetically couple (or magnetically secure) to the external anchor assembly 1 in example embodiments.

The External Anchor Assembly (e.g., Element 1)

In an example embodiment, the external anchor assembly 1 (e.g., element 1 recited in the present disclosure) may comprise one or more external anchor bodies (e.g., element 3502). The external anchor assembly 1 may further comprise one or more magnetic assemblies (e.g., element 3510). The external anchor assembly 1 may further comprise one or more cryo-cooler assemblies, coldheads, or the like (or "cryo-cooler assembly") (e.g., element 3520). The external anchor assembly 1 may further comprise one or more heat rods (e.g., element 3530). The external anchor assembly 1 may further comprise one or more support rods (e.g., element 3540). The external anchor assembly 1 may further comprise one or more connecting sections (e.g., element 3508). The external anchor assembly 1 may further comprise one or more support clamps (e.g., element 3550). The external anchor assembly 1 may further comprise one or more intermediary members (e.g., element 1d). The external anchor assembly 1 may further comprise one or more support structures (e.g., element 1c). These elements of the external anchor assembly 1 are further described below with reference to the Figures.

The External Anchor Body (e.g., Element 3502)

As illustrated in at least FIGS. 35A-D, FIG. 37C, FIG. 38A, FIG. 38B, and FIG. 38C, the external anchor body 3502 may collectively comprise a body, such as an elongated body, having a first end 3502a, a second end 3502b, and one or more walls forming a substantially hollow interior. The external anchor body 3502 may comprise a main external anchor body 3504. The external anchor body 3502 may further comprise a cryo-cooler housing 3506. The external anchor body 3502 may further comprise a connector section 3508 for connecting the main external anchor body 3504 to the cryo-cooler housing 3506. It is to be understood in the present disclosure that one or more of the main external anchor body 3504, the cryo-cooler housing 3506, and the connector section 3508 may be formed as a unitary article, or alternatively, as several separate elements, without departing from the teachings of the present disclosure. These elements of the external anchor body 3502 are further described below with reference to the Figures.

The main external anchor body 3504 may be operable to receive and house the magnetic assembly 3150 at the first end 3502a. The main external anchor body 3504 may be further operable to receive and house the one or more heat rods 3530. The main external anchor body 3504 may be further operable to receive and house the one or more support rods 3540. The main external anchor body 3504 may be further operable to receive, house, and secure in place a support clamp 3550, which, in example embodiments, may be operable to secure the one or more heat rods 3530 and/or the one or more support rods 3540 in place within the main external anchor body 3504.

The main external anchor body 3504 may be formed in any one or more of a plurality of shapes, or combinations thereof, including shapes that have one or more cross sections that is/are circular, elliptical, square, rectangular, hexagonal, etc. For example, a shape of the main external anchor body 3504 may be selected based on, among other things, one or more of: a shape of a portion of the magnetic assembly 3150; a shape of a portion of the conductive housing 3514; a shape of the configuration of the one or more superconducting magnets 3512; a shape of a portion of the cryo-cooler assembly 3520; a shape of a portion of the cryo-cooler 3522; a shape of a portion of the one or more heat rods 3530; a shape of a portion of the one or more support rods 3540; a shape of the connector section 3508; etc.

The main external anchor body 3504 may be operable to receive at least a portion of and secure to the support structure 1c in example embodiments. The main external anchor body 3504 may be further operable to fixably secure to the intermediary member 1d at first end 3502a.

A length (or height) of the main external anchor body 3504 may be between about 500 mm to 1500 mm, a diameter of the main external anchor body 3504 may be between about 35 mm to 85 mm, and a wall thickness of the main external anchor body 3504 may be between about 1 mm to 5 mm. The aforementioned dimensions of the main external anchor body 3504 may be a maximum dimension, an average dimension, a typical dimension, a minimum dimension, etc.

The main external anchor body 3504 may be formed using any one or more of a plurality of materials, such as surgical-grade metals, stainless steel, etc.

In an example embodiment, the cryo-cooler housing 3506 may be formed in any one or more of a plurality of shapes, or combinations thereof, including shapes that have one or more cross sections that is circular, elliptical, square, rectangular, hexagonal, etc. For example, a shape of the cryo-cooler housing 3506 may be selected based on, among other things, one or more of: a shape of a portion of the cryo-cooler 3522; a shape of a portion of the one or more heat rods 3530; a shape of the connector section 3508; a shape of a portion of the magnetic assembly 3510; a shape of a portion of the conductive housing 3514; etc.

A length (or height) of the cryo-cooler housing 3506 may be between about 95 mm to 250 mm, a diameter of the cryo-cooler housing 3506 may be between about 85 mm to 300 mm, and a wall thickness of the cryo-cooler housing 3506 may be between about 2 mm to 10 mm. The aforementioned dimensions of the cryo-cooler housing 3506 may be a maximum dimension, an average dimension, a typical dimension, a minimum dimension, etc.

The cryo-cooler housing 3506 may be formed using any one or more of a plurality of materials, such as surgical-grade metals, aluminum, stainless steel, plastics, etc.

Although example embodiments depict the main external anchor body 3504 and the cryo-cooler housing 3506 to be two separate elements, it is to be understood in the present disclosure that example embodiments of the main external anchor body 3504 and the cryo-cooler housing 3506 may be formed as a unitary article, or alternatively, as more than two separate elements, without departing from the teachings of the present disclosure.

In an example embodiment, the connector section 3508 is for use in connecting and securing the main external anchor body 3504 with the cryo-cooler housing 3506. It is to be understood in the present disclosure that the main external anchor body 3504 may be directly connectable and securable to the cryo-cooler housing 3506 in example embodiments without the need for connector section 3508 and without departing from the teachings of the present disclosure.

The connector section 3508 may be formed in any one or more of a plurality of shapes, or combinations thereof, including shapes that have one or more cross sections that is/are circular, elliptical, square, rectangular, hexagonal, etc. For example, a shape of the connector section 3508 may be selected based on, among other things, one or more of: a shape of a portion of the cryo-cooler assembly 3520; a shape of a portion of the cryo-cooler housing 3506; a shape of a portion of the cryo-cooler 3522; a shape of a portion of the main external anchor body 3504; a shape of a portion of the magnetic assembly 3510; a shape of a portion of the conductive housing 3514; etc.

A length (or height) of the connector section 3508 may be between about 300 mm to 1500 mm, a diameter of the connector section 3508 may be between about 10 mm to 50 mm. The aforementioned dimensions of the connector section 3508 may be a maximum dimension, an average dimension, a typical dimension, a minimum dimension, etc.

The connector section 3508 may be formed using any one or more of a plurality of materials, such as surgical-grade metals, copper, aluminum, etc.

The Magnetic Assembly (e.g., Element 3510)

The magnetic assembly 3510 may comprise one or more superconducting magnets (e.g., element 3512). The magnetic assembly 3510 may further comprise a conductive housing (e.g., element 3514). The magnetic assembly 3510 may further comprise one or more first heat rod receiving sections (e.g., element 3516). These elements of the magnetic assembly 3510 are further described below with reference to the Figures.

In an example embodiment, the magnetic assembly 3510 may comprise one or more superconducting magnet 3512. The one or more superconducting magnets 3512 may comprise high temperature superconductors (or HTS), low temperature superconductors, and/or any other forms and/or types of superconductor operable to generate a large magnetic field.

The one or more superconducting magnets 3512 may be configured in one or more stacks. For example, the one or more superconducting magnets 3512 may be configured in a single stack arrangement, such as the example embodiment illustrated in FIGS. 36A and 36B. The one or more superconducting magnets 3512 may also be configured in a plurality of stacks, such as the example embodiment illustrated in FIG. 36C. Although FIG. 36B illustrates an arrangement of 3 stacks of superconducting magnets 3512, it is to be understood in the present disclosure that an arrangement of more or less than 3 stacks of superconducting magnets 3512 are contemplated without departing from the teachings of the present disclosure.

Figure 36A:
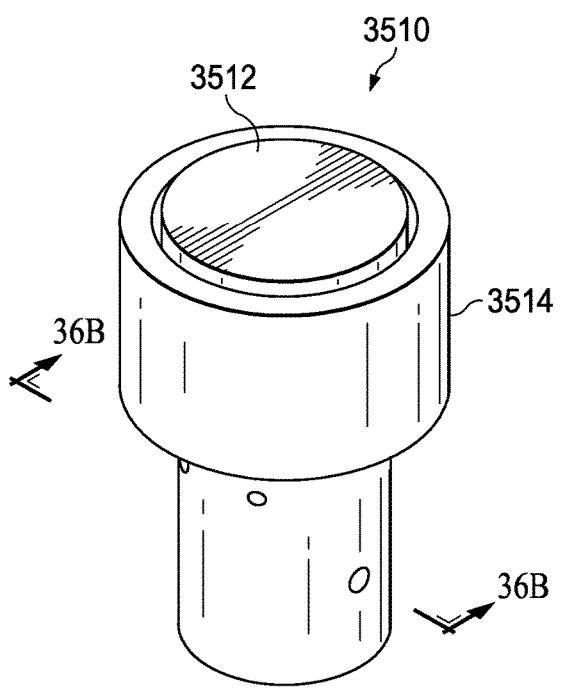
FIG. 36A is a perspective view of an exemplary magnetic assembly having one or more superconducting magnets.

In an example embodiment having a single stack of superconducting magnets 3512, such as the example embodiment illustrated in FIG. 36A, each superconducting magnet 3512 may have a circular cross-section and comprise a radius of between about 5 mm to 65 mm. Furthermore, each of the superconducting magnets 3512 may comprise a height of between about 1 mm to 30 mm. Furthermore, the stack of superconducting magnets 3512 may comprise a height (i.e., collective height of all superconducting magnets 3512 in the stack) of between about 1 mm to 75 mm. The height of the stack of superconducting magnets 3512 may be equal to or greater than the radius of each superconducting magnet 3512 in the stack.

In an example embodiment having a single stack of superconducting magnets 3512, each superconducting magnet 3512 may have other cross-sectional shapes. For example, each superconducting magnet 3512 may comprise a hexagonal cross-section, and comprise a distance across diametrically opposite corners (or points) of the hexagonal cross-section of between about 5 mm to 65 mm. Furthermore, each of the superconducting magnets 3512 may comprise a height of between about 1 mm to 30 mm. Furthermore, the stack of superconducting magnets 3512 may comprise a height (i.e., collective height of all superconducting magnets 3512 in the stack) of between about 1 mm to 75 mm. The height of the stack of superconducting magnets 3512 may be equal to or greater than the distance across diametrically opposite corners (or points) of the hexagonal cross-section of each superconducting magnet 3512 in the stack.

Figure 36B:
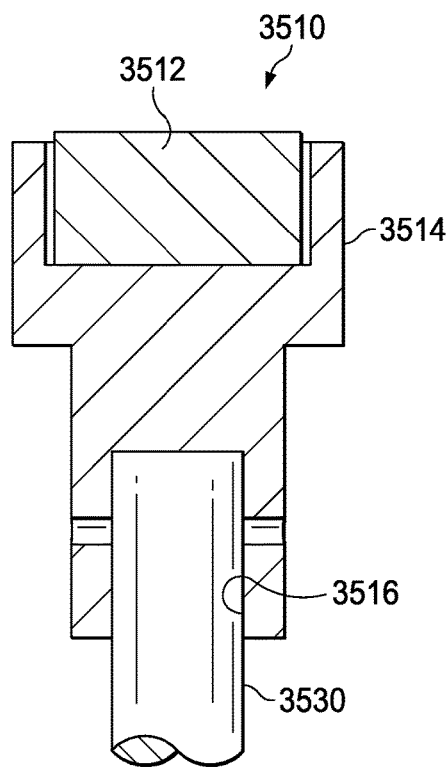
FIG. 36B is a cross-sectional view of an exemplary magnetic assembly having one or more superconducting magnets.
Figure 36C:
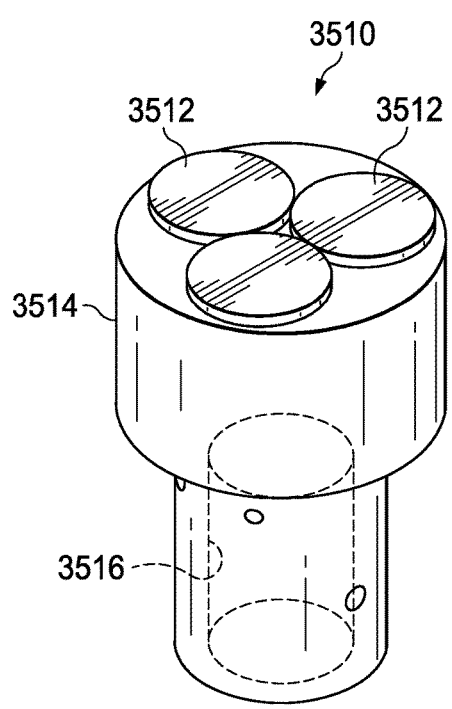
FIG. 36C is a cross-sectional view of an exemplary magnetic assembly having three stacks of one or more superconducting magnets.

In an example embodiment having a plurality of stacks of superconducting magnets 3512, such as the example embodiment illustrated in FIG. 36B, each superconducting magnet 3512 may have a circular cross-section and comprise a radius of between about 5 mm to 65 mm. Furthermore, each of the superconducting magnets 3512 may comprise a height of between about 1 mm to 30 mm. Furthermore, each of the stacks of superconducting magnets 3512 may comprise a height (i.e., collective height of all superconducting magnets 3512 in the stack) of between about 1 mm to 75 mm. The height of each of the stacks of superconducting magnets 3512 may be equal to or greater than the radius of each superconducting magnet 3512.

It is to be understood in the present disclosure that each superconducting magnet 3512 in the single stack of superconducting magnets 3512 and the plurality of stacks of superconducting magnets 3512 may comprise other dimensions and/or cross-sectional shapes. Furthermore, each stack in the plurality of stacks of superconducting magnets 3512 may comprise superconducting magnets 3512 having the same or different dimensions and/or cross-sectional shapes as one or more other stacks of superconducting magnets 3512 without departing from the teachings of the present disclosure.

The aforementioned dimensions of the one or more superconducting magnets 3512, and/or one or more stacks thereof, may be a maximum dimension, an average dimension, a typical dimension, a minimum dimension, etc.

In an example embodiment, each of the one or more superconducting magnets 3512, and/or one or more stacks thereof, may be formed in any one or more of a plurality of shapes, or combinations thereof, including shapes that have one or more cross sections that is/are circular, elliptical, square, rectangular, hexagonal, etc. For example, a shape of each of the one or more superconducting magnets 3512, and/or one or more stacks thereof, may be selected based on, among other things, one or more of: a shape of a portion of the magnetic assembly 3510; a shape of a portion of the conductive housing 3514; a desired configuration of the one or more superconducting magnets 3512; a desired magnitude, shape, and/or direction of the magnetic field to be generated by the magnetic assembly 3510; a shape of a portion of the internal anchor assembly 17; etc.

The one or more superconducting magnets 3512 may be formed using any one or more of a plurality of materials, including one or more of barium (Ba), copper (Cu), oxygen (O), rare earth metals, etc. Rare earth metals may include yttrium (Y), ytterbium (Yb), europium (Eu), gadolinium (Gd), samarium (Sm), and/or neodymium (Nd). The one or more superconducting magnets 3512 may further comprise silver (Ag), iron (Fe), magnesium (Mg), boron (B), and/or other metal and metal oxide compounds.

In an example embodiment, the one or more superconducting magnets 3512 may be operable to generate (or support/emit) a magnetic field having a magnitude of between about 0 to 20 Tesla within an operational temperature range of between about 20 to 94 K. The one or more superconducting magnets 3512 may have a critical temperature of between about 94+/−1 K. In example embodiments, as the temperature of the one or more superconducting magnets 3512 increases, the critical current ($J_c$) of the one or more superconducting magnets 3512 will decrease. Furthermore, when the temperature of the one or more superconducting magnets 3512 reaches and/or exceeds the aforementioned critical temperature, the magnitude of the magnetic field generated by the one or more superconducting magnets may be diminished, that is, reduce to a magnitude of about 0 Tesla in example embodiments. In this regard, when an internal anchor assembly 17 is magnetically coupled to an external anchor assembly 1 and an immediate removal or uncoupling of the external anchor assembly 1 from the internal anchor assembly 17 is required or desired, example embodiments may be operable to increase the temperature of the one or more superconducting magnets 3512 via the temperature control section (which may include one or more of the cryo-cooler assembly 3520, the cryo-cooler 3522, a heater, and/or the one or more heat rods 3530, and may also include the conductive housing 3514) to a temperature equal to or greater than the critical temperature so as to diminish the magnitude of the magnetic field of the one or more superconducting magnets 3512, as described above and in the present disclosure.

In example embodiments, when the external anchor assembly 1 is magnetically coupled to the internal anchor assembly 17 via the applied magnetic field of the one or more superconducting magnets 3512 (of the magnetic assembly 3510), the magnetic coupling or attractive force between the one or more superconducting magnets 3512 and the internal anchor assembly 17 may be sufficient to resist a force of between about 0.1 to 10 N applied to or by an instrument assembly 2 attached to the internal anchor assembly 17.

The conductive housing 3514 may be formed as a unitary article, or alternatively, as a collection of a plurality of parts. The conductive housing 3514 may comprise a main conductive housing body having one or more superconducting magnet receiving sections for receiving and housing the one or more superconducting magnets 3512. The conductive housing 3514 may further comprise one or more first heat rod receiving sections 3516 for receiving and housing at least a portion (end) of one or more heat rods 3530. For example, as illustrated in FIG. 36A, the conductive housing 3514 may comprise one superconducting magnet receiving section in example embodiments having a single stack of superconducting magnets 3512 and one first heat rod receiving section 3516 for receiving an end of a heat rod 3530. As another example, as illustrated in FIG. 36B, the conductive housing 3514 may comprise a plurality of receiving sections (3 receiving sections are illustrated in FIG. 36B) in example embodiments having a plurality of stacks (3 stacks as illustrated in FIG. 36B) of superconducting magnets 3512 and one first heat rod receiving section 3516 for receiving an end of a heat rod 3530.

In an example embodiment, the conductive housing 3514 may be formed in any one or more of a plurality of shapes, or combinations thereof, including shapes that have one or more cross sections that is/are circular, elliptical, square, rectangular, hexagonal, etc. For example, a shape of the conductive housing 3514 may be selected based on, among other things, one or more of: a shape of a portion of the magnetic assembly 3510; a shape of one or more of the superconducting magnets 3512; a desired configuration of the one or more superconducting magnets 3512; a desired magnitude, shape, and/or direction of the magnetic field to be generated by the magnetic assembly 3510; a desired extent or quickness of temperature control desired for the one or more superconducting magnets 3512; a shape of a portion of the internal anchor assembly 17; etc.

A height of the conductive housing 3514 may be between about 15 mm to 100 mm, a diameter of the conductive housing 3514 may be between about 25 mm to 80 mm, and a minimum wall thickness of the conductive housing 3514 for the receiving sections (that receive the stack of superconducting magnets 3512) may be between about 0.5 mm to 10 mm. The aforementioned dimensions of the conductive housing 3514 may be a maximum dimension, an average dimension, a typical dimension, a minimum dimension, etc.

In example embodiments, the conductive housing 3514 may be provided in direct physical contact with the one or more superconducting magnets 3512 via the superconducting magnet receiving section. Furthermore, the conductive housing 3514 may be provided in direct physical contact with the one or more heat rods 3530 via the one or more first heat rod receiving sections 3516.

The conductive housing 3514 may be formed using any one or more of a plurality of conductive materials, such as copper, aluminum, etc.

The Cryo-Cooler Assembly (e.g., Element 3520)

Figure 37A:
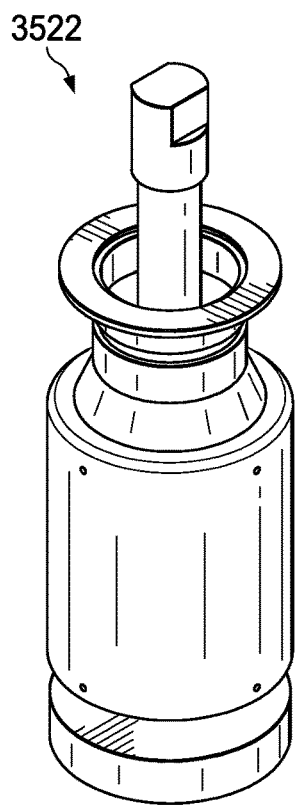
FIG. 37A is a perspective view of an exemplary cryo-cooler.
Figure 37B:
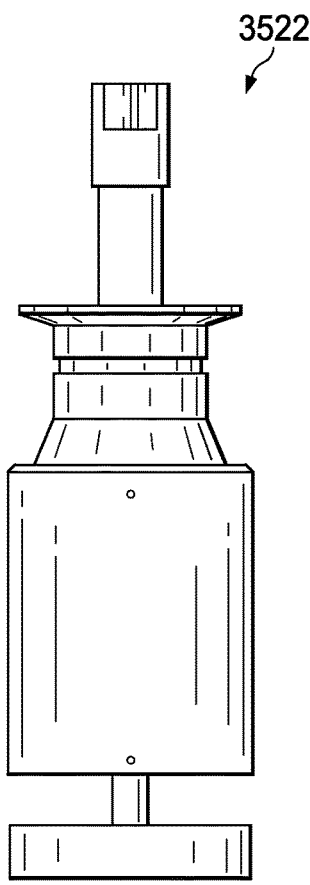
FIG. 37B is a side view of an exemplary cryo-cooler.
Figure 37C:
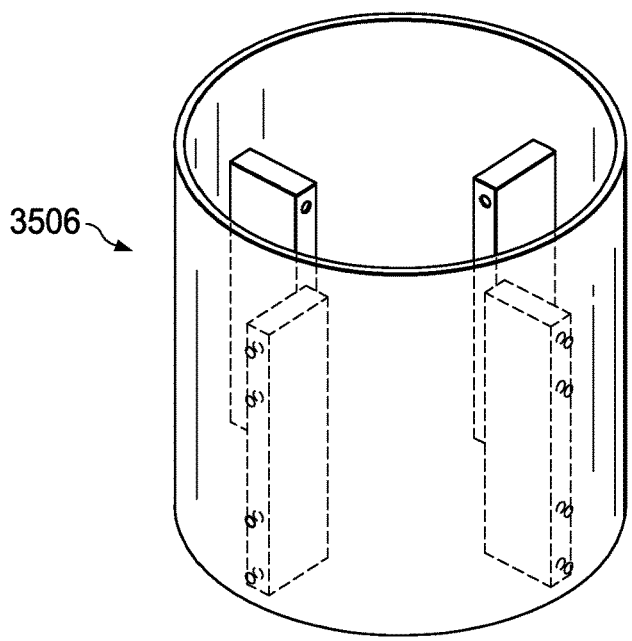
FIG. 37C is a perspective view of a portion of an exemplary external anchor body for receiving an exemplary cryo-cooler.
Figure 38A:
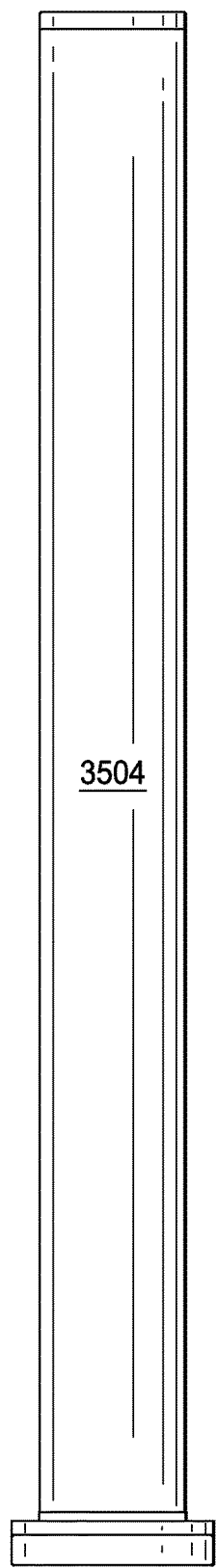
FIG. 38A is a side view of a portion of an exemplary external anchor body.
Figure 38B:
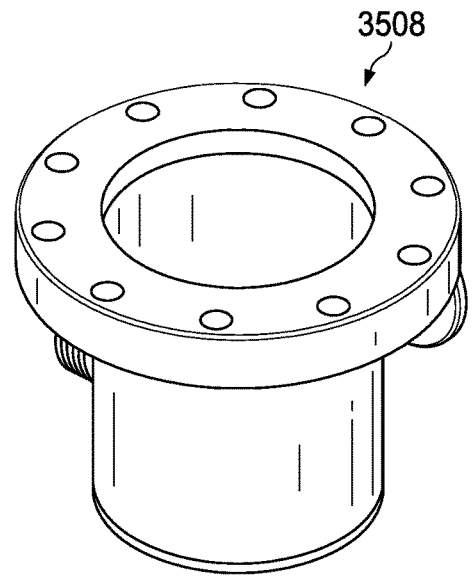
FIG. 38B is a perspective view of a portion of an exemplary external anchor body.
Figure 38C:
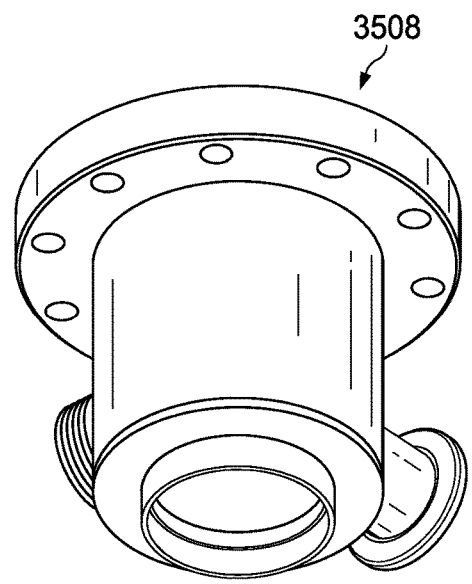
FIG. 38C is another perspective view of a portion of an exemplary external anchor body.
Figure 39:
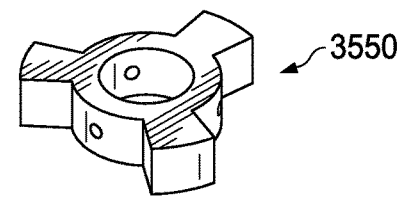
FIG. 39 is an example illustration of an exemplary supporting clamp.

The cryo-cooler assembly 3520 may comprise a cryo-cooler 3522, as illustrated in FIGS. 37A and 37B. The cryo-cooler assembly 3520 may further comprise a second heat rod receiving section 3526 for receiving an end of the one or more heat rods 3530. In an example embodiment, the cryo-cooler assembly 3520 may be fixedly positioned at end 3502b.

The cryo-cooler 3522 may be any cryo-cooler, or the like, that may be configurable to control a temperature of the one or more superconducting magnets 3512. The cryo-cooler 3522 may be further configurable to generate, emit, and/or cause a reduction and/or increase in temperature of the one or more superconducting magnets 3512. For example, the cryo-cooler 3522 may be configurable to control and/or cause a reduction and/or increase in the temperature of the one or more superconducting magnets 3512 via the one or more heat rods 3530 and the conductive housing 3514.

The cryo-cooler 3522 may be any cryo-cooler, or the like, known by persons of ordinary skill in the art.

The One or More Heat Rods (e.g., Element 3530)

The one or more heat rods 3530 may be any heat rod, of the like, operable to communicate or cause a control of, reduction in, and/or increase in temperature of the one or more superconducting magnets 3512 from the cryo-cooler assembly 3520. The one or more heat rods 3530 may be in direct physical contact with the conductive housing 3514 in example embodiments. Furthermore, the one or more heat rods 3530 may be in direct physical contact with the cryo-cooler assembly 3520 in example embodiments.

In an example embodiment, each of the one or more heat rods 3530 may be formed in any one or more of a plurality of shapes, or combinations thereof, including shapes that have one or more cross sections that is/are circular, elliptical, square, rectangular, hexagonal, etc. For example, a shape of each heat rod 3530 may be selected based on, among other things, one or more of: a shape of a portion of the magnetic assembly 3510; a shape of one or more of the superconducting magnets 3512; a desired configuration of the one or more superconducting magnets 3512; a desired magnitude, shape, and/or direction of the magnetic field to be generated by the magnetic assembly 3510; a desired extent or quickness of temperature control desired for the one or more superconducting magnets 3512; a shape of a portion of the internal anchor assembly 17; etc.

A length of the one or more heat rods 3530 may be between about 50 mm to 1000 mm, and a diameter of the one or more heat rods 3530 may be between about 10 to 75 mm.

The aforementioned dimensions of the one or more heat rods 3530 may be a maximum dimension, an average dimension, a typical dimension, a minimum dimension, etc.

The one or more heat rods 3530 may be formed using any one or more of a plurality of materials, such as copper, aluminum, etc.

The One or More Support Rods (e.g., Element 3540)

The one or more support rods 3540 may be any structurally strong/rigid rod, or the like, operable to support and position the one or more heat rods 3530 in the external anchor body 3502.

In an example embodiment, each of the one or more support rods 3540 may be formed in any one or more of a plurality of shapes, or combinations thereof, including shapes that have one or more cross sections that is/are circular, elliptical, square, rectangular, hexagonal, etc.

A length of the one or more support rods 3540 may be between about 100 mm to 750 mm, and a diameter of the one or more support rods 3540 may be between about 2 mm to 10 mm. The aforementioned dimensions of the one or more support rods 3540 may be a maximum dimension, an average dimension, a typical dimension, a minimum dimension, etc.

The one or more support rods 3540 may be formed using any one or more of a plurality of materials, such as carbon fiber, glass fiber, plastics, stainless steel, other metals etc.

The Intermediary Member (e.g., Element 1*d*)

The intermediary member 1*d* may be any object, assembly, or device configurable to control a separation distance between the magnetic assembly 3510 (or external anchor assembly 1 or one or more superconducting magnets 3512) and the internal anchor assembly 17. For example, the intermediary member 1*d* may be an inflatable bladder configurable to receive a gas and inflate, thereby causing an increase in a separation distance between the magnetic assembly 3510 (or external anchor assembly 1 or one or more superconducting magnets 3512) and the internal anchor assembly 17. In example embodiments, the intermediary member 1*d* may be configurable to provide a separation distance between the magnetic assembly 3510 (or external anchor assembly 1 or one or more superconducting magnets 3512) and the internal anchor assembly 17 of about 1 mm to 50 mm.

The Support Structure (e.g., Element 1*c*)

Figure 40A:
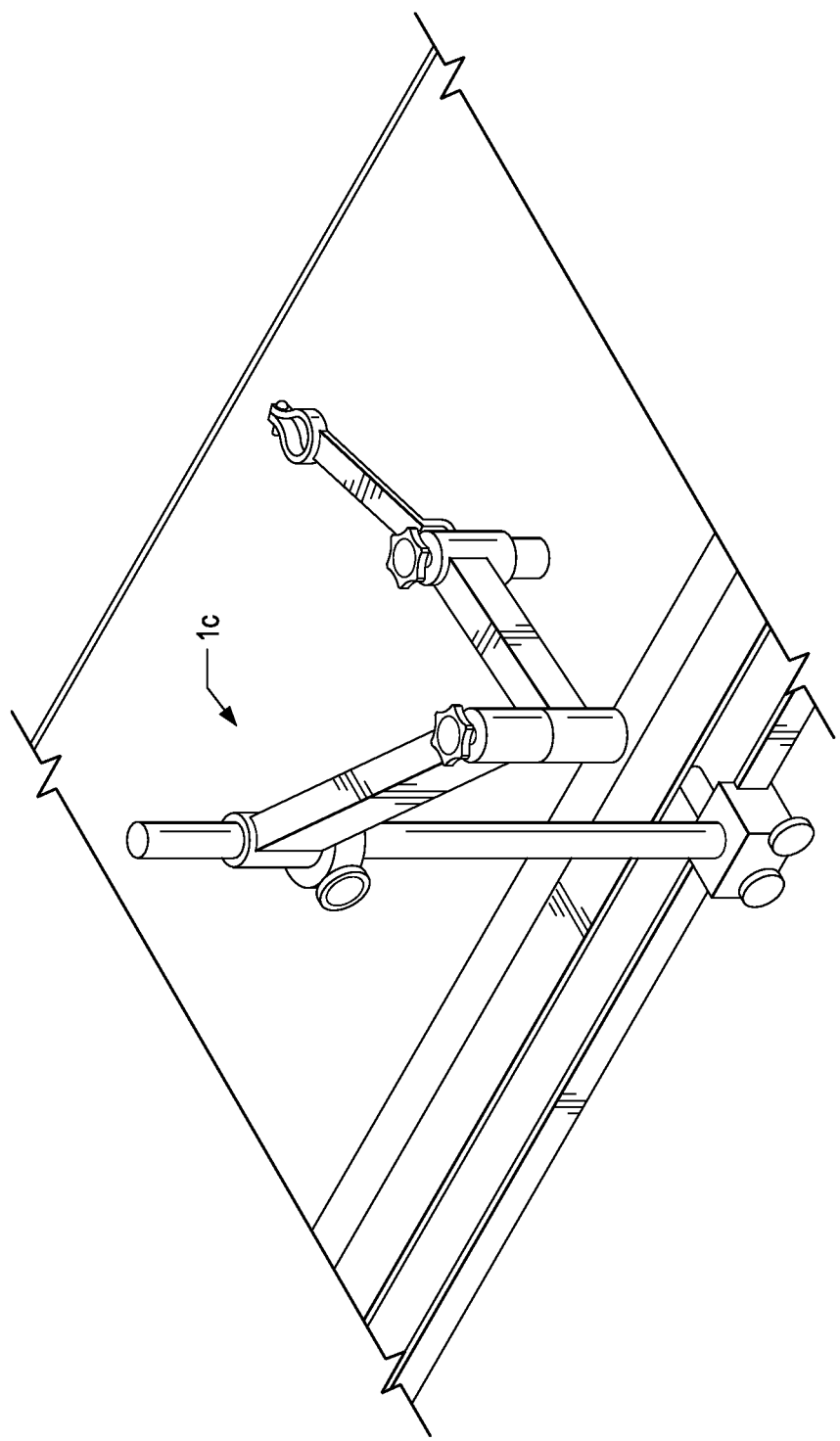
FIGS. 40A and 40B are perspective views of an exemplary support structure.
Figure 40B:
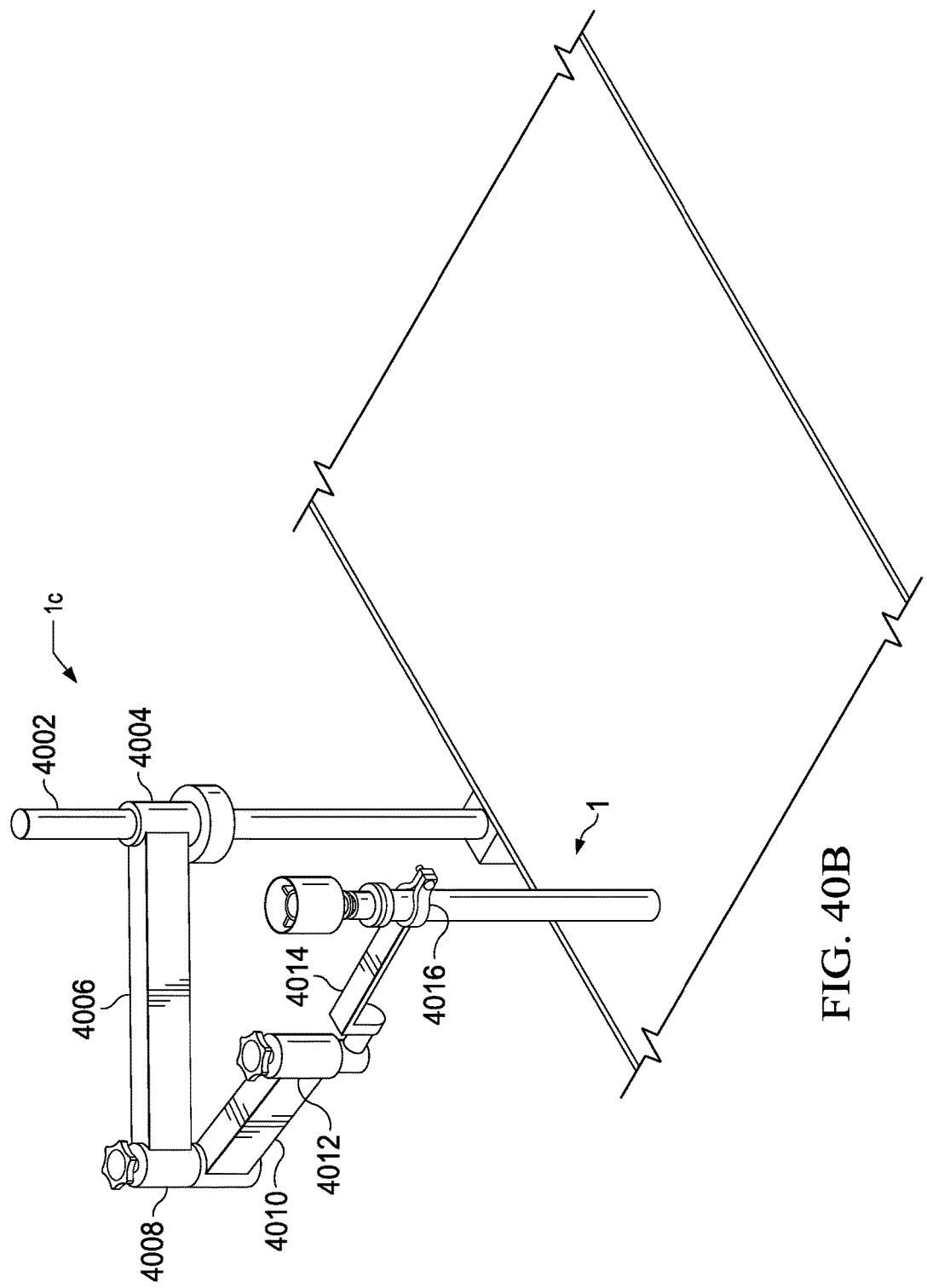

As illustrated in FIGS. 40A and 40B, an example embodiment of a support structure 1*c* may comprise a plurality of segments 4002, 4006, 4010, and 4014 in communication with one another via joints or connecting portions 4004, 4008, and 4012, and external anchor assembly contact portion 4016. The support structure 1*c* may be operable to securely fix the position and/or orientation (hereinafter "position") of the external anchor assembly 1, and may also be operable to provide sufficient anchoring and/or reactive forces to stabilize against forces desired and/or necessary to be applied by at least one or more instruments of the instrument assembly 2, during a surgical action or procedure.

The support structure 1*c* may be further configurable to move the external anchor assembly 1, including controlling, decreasing, and/or increasing a separation distance between the external anchor assembly 1 and the internal anchor assembly 17, in example embodiments. In this regard, it is recognized in the present disclosure that the controlling, decreasing, and/or increasing of the separation distance between the external anchor assembly 1 and the internal anchor assembly 17 may be performed by the support structure 1*c* and/or the intermediary member 1*d* in example embodiments.

Figure 41:
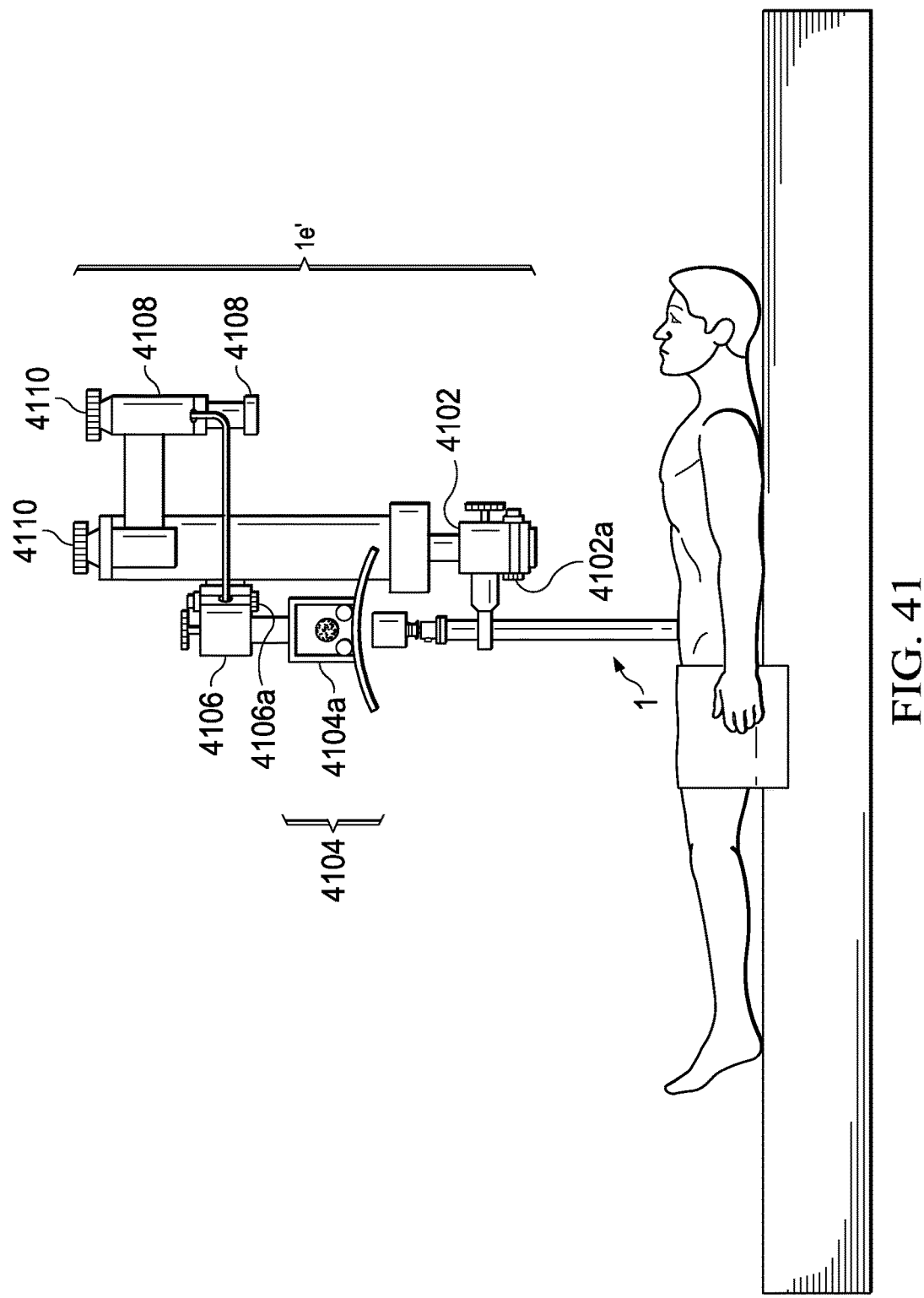
FIG. 41 is a side view of an exemplary controllable swivel assembly of an exemplary support structure.

The support structure 1*c* may further include a controllable swivel assembly 1*e*', as illustrated in FIG. 41) comprising one or more of a first swivel portion 4102, second swivel portion 4104, and/or third swivel portion 4106. The controllable swivel assembly 1*e*' may further comprise a motor 4102*a* for the first swivel portion 4102, a motor 4104*a* for the second swivel portion 4104, a motor 4106*a* for the third swivel portion 4106, one or more supporting arms 4108, and one or more locks 4110.

The support structure 1*e*', including the controllable swivel assembly 1*e*', may be anchored to one or more stationary objects, such as a side rail of a surgical table/bed illustrated in FIG. 40A.

Method of Configuring a Surgical System (e.g., Method 4200)

Figure 42:
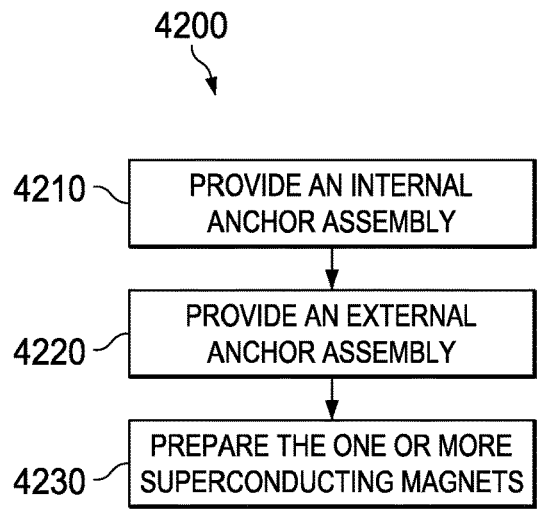
FIG. 42 is an example illustration of a method of configuring a surgical system.

As illustrated in FIG. 42, an example embodiment of a method of configuring a surgical system (e.g., method 4200) may comprise providing an internal anchor assembly (e.g., action 4210). The internal anchor assembly provided may include example embodiments of the internal anchor assembly (e.g., elements 17, 21, 22, and/or 156) described above and in the present disclosure. The internal anchor assembly may be configurable to be inserted into and positioned inside a cavity of a body (i.e., patient body).

The method (e.g., method 4200) may further comprise providing an external anchor assembly (e.g., action 4220). The external anchor assembly provided may include example embodiments of the external anchor assembly (e.g., element 1) described above and in the present disclosure. In an example embodiment, the external anchor assembly may comprise a magnetic assembly, a temperature control section, and an external anchor body.

The magnetic assembly provided may include example embodiments of the magnetic assembly 3510 described above and in the present disclosure. In an example embodiment, the magnetic assembly may comprise one or more superconducting magnets configurable to generate a magnetic field. The one or more superconducting magnets may include example embodiments of the superconducting magnet 3512, and configurations and arrangements thereof, described above and in the present disclosure. The magnetic assembly may further comprise a conductive housing for receiving the one or more superconducting magnets. The conductive housing may include example embodiments of the conductive housing 3514, including receiving sections thereof, described above and in the present disclosure.

The temperature control section provided may include example embodiments of the cryo-cooler assembly 3520 and the one or more heat rods 3530 described above and in the present disclosure. For example, the cryo-cooler assembly may comprise a cryo-cooler 3522 and a receiving portion for receiving an end of the one or more heat rods 3530. Furthermore, the one or more heat rods 3530 may be in direct physical contact with the cryo-cooler assembly and the conductive housing of the magnetic assembly.

The external anchor body provided may include example embodiments of the external anchor body 3502, including ends 3502*a* and 3502*b*, described above and in the present disclosure. In an example embodiment, the external anchor body is configurable to receive the magnetic assembly at end 3502*a* and the temperature control section, including the cryo-cooler assembly, at end 3502*b*. The external anchor body may be further configurable to receive the one or more heat rods.

The method (e.g., method 4200) may further comprise preparing the one or more superconducting magnets (e.g., action 4230).

Figure 43:
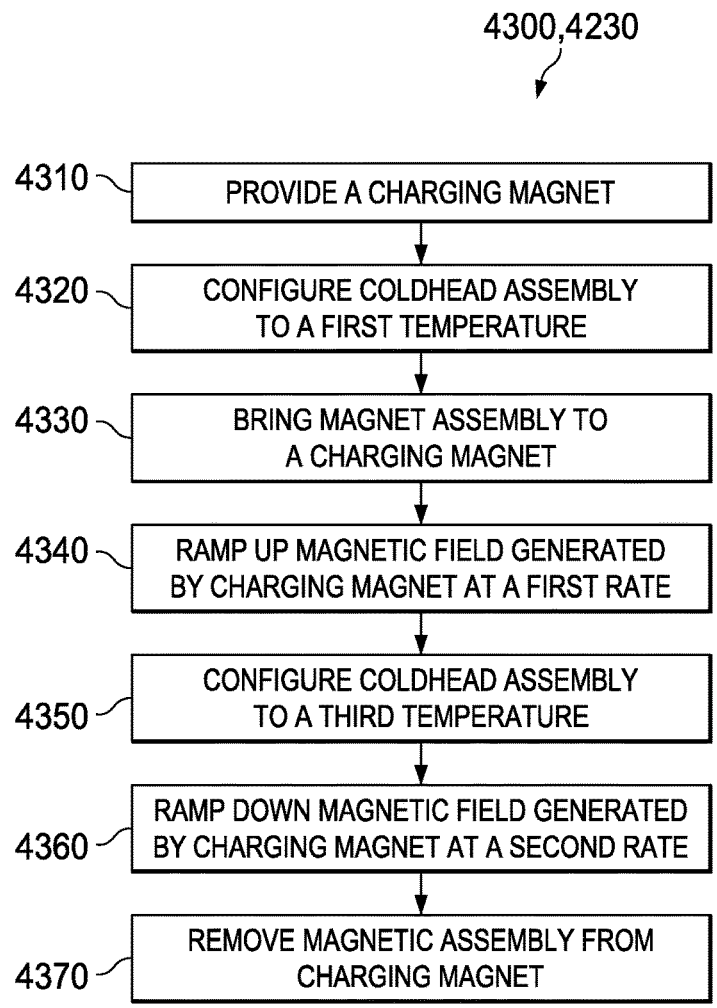
FIG. 43 is an example illustration of a method of preparing one or more superconducting magnets.

As illustrated in FIG. 43, a method (e.g., method 4300, action 4230) of preparing the one or more superconducting magnets may include providing a charging magnet (e.g., action 4310). The charging magnet provided may be any magnet operable to interact (or charge) the one or more superconducting magnets, and may include an electromagnet, superconducting magnet, or the like.

The method (e.g., method 4300) may further comprise configuring the cryo-cooler assembly (i.e., cryo-cooler) to a first temperature (e.g., action 4320). The first temperature may be between about 90 to 300 K. In an example embodiment, the first temperature may be a temperature operable to bring a temperature of the one or more superconducting magnets to be lesser than or equal to a second temperature. The second temperature may be between about 90 to 100 K. For example, the first temperature may be a set point temperature of about 90 K and the second temperature may be a temperature of about 100 K.

The method (e.g., method 4300) may further comprise bringing the magnetic assembly to the charging field (or magnet) (e.g., action 4330). For example, the end 3502*a* of the external anchor assembly 3502 to which the magnetic assembly 3510 is positioned may be brought in contact with or near to the charging field.

The method (e.g., method 4300) may further comprise ramping up (or gradually increase) a magnetic field generated by the charging field at a first rate (e.g., action 4340). The first rate may be between about 0.01 to 5 Tesla/minute. For example, the first rate may be a rate of about 0.5 Tesla/minute.

The method (e.g., method 4300) may further comprise configuring the cryo-cooler assembly (i.e., cryo-cooler) to a third temperature (e.g., action 4350). The third temperature may be less than the first temperature. The third temperature may be between about 50 K to 65 K. In an example embodiment, the third temperature may be a temperature operable to bring the temperature of the one or more superconducting magnets to be lesser than or equal to a fourth temperature. The fourth temperature may be less than the second temperature. The fourth temperature may be between about 50 K to 65 K. For example, the third temperature may be about 50 to 70 K and the fourth temperature may be about 60 to 80 K.

The method (e.g., method 4300) may further comprise ramping down (or gradually decreasing) the magnetic field generated by the charging field at a second rate (e.g., action 4360). The second rate may be between about 0.01 to 5 Tesla/minute. For example, the second rate may be a rate of about 0.5 Tesla/minute.

The method (e.g., method 4300) may further comprise removing the magnetic assembly from the charging field (e.g., action 4370). That is, the end 3502*a* of the external anchor assembly 3502 to which the magnetic assembly 3510 is housed may be brought (or moved) away from the charging field. In an example embodiment, this action (e.g., action 4370) may be performed when (i.e., at the time of, or after) the magnetic field generated by the charging field reaches a final magnetic field value. The final magnetic field value may be between about 0 to +/−0.1 Tesla. For example, the final magnetic field value may be about 0 Tesla.

Either before, during, or after completion of the preparing of the one or more superconducting magnets (e.g., method 4300 and action 4230), the internal anchor assembly may be inserted into a cavity of a body (i.e., patient body) and positioned at an interior surface of the cavity of the body.

Either before, during, or after completion of the preparing of the one or more superconducting magnets (e.g., method 4300 and action 4230), a support structure may be configured. The support structure may include example embodiments of the support structure (e.g., element 1*c*) and/or controllable swivel assembly (e.g., element 1*c*') described above and in the present disclosure. The support structure may be configured to receive and fixably position the external anchor assembly at an exterior surface of the body (i.e., patient body). In example embodiments, the external anchor assembly is fixably positioned based on the position or desired position of the internal anchor assembly. For example, after the internal anchor assembly is inserted into and positioned inside the cavity of the body, the support structure may fix the position of the external anchor assembly based on the position of the internal anchor assembly inside the cavity of the body. As another example, before (or at the same time as) the internal anchor assembly is inserted into and positioned inside the cavity of the body at a desired position, the support structure may fix the position of the external anchor assembly based on the desired position of the internal anchor assembly inside the cavity of the body.

The external anchor assembly may then be magnetically coupled to the internal anchor assembly via the magnetic field generated by the one or more superconducting magnets of the magnetic assembly.

Either before, during, or after the insertion and positioning of the internal anchor assembly in the cavity of the body (i.e., patient body), an instrument assembly may be provided. The instrument assembly may include example embodiments of the instrument assembly (e.g., elements 2, 18, 19, 150, and/or 1000) described above and in the present disclosure. In an example embodiment, the instrument assembly may comprise an instrument (such as an end effector, gripper, cutting tool, camera, video camera, light, etc.) at a first end of the instrument assembly and an instrument assembly attaching section at a second end of the instrument assembly.

Either before, during, or after the insertion and positioning of the internal anchor assembly in the cavity of the body (i.e., patient body), the instrument assembly may be inserted into the cavity of the body. After the internal anchor assembly is inserted into the cavity of the body, the instrument assembly may be secured to the internal anchor assembly. The instrument assembly may be secured to the internal anchor assembly by securing an internal anchor attaching section of the internal anchor assembly to the instrument assembly attaching section.

It is recognized in the present disclosure that the internal anchor assembly and the instrument assembly may be already attached/secured together, or alternatively, formed as a unitary article in example embodiments.

In an example embodiment, the magnetic assembly may be configurable to generate a magnetic field with a magnitude of about 0 to 1.5 Tesla (when measured at the anchor surface). The magnetic assembly may be configurable to generate a peak or all of the magnetic field in a particular or desired direction, area, or volume (i.e., towards the internal anchor assembly and/or the desired position of the internal anchor assembly within the cavity of the patient body).

In an example embodiment, the external anchor assembly may be configurable to selectively vary the magnetic field applied to the internal anchor assembly between a magnitude of about 0 to 2 Tesla. For example, when the external anchor assembly magnetically couples to the internal anchor assembly, and when the magnetic assembly is magnetically coupled to the internal anchor assembly at a first separation distance, such as a first separation distance of about 0 to 50 mm, from the internal anchor assembly, the external anchor assembly may be configurable to vary the magnitude of the magnetic field applied to (or at) the internal anchor assembly by varying the first separation distance. In an example embodiment, the magnetic field applied at the internal anchor assembly may be reduced by selectively configuring the support structure to increase the first separation distance. Similarly, the magnetic field applied at the internal anchor assembly may be increased by selectively configuring the support structure to decrease the first separation distance.

As another example, the first separation distance may be varied by the intermediary member. For example, if the intermediary member is an inflatable bladder, the first separation distance may be varied by varying a dimension (such as thickness) of the intermediary member.

In an example embodiment, the external anchor assembly may be configurable to selectively vary the generated magnetic field between a magnitude of about 0 to 5 Tesla. The external anchor assembly may be configurable to selectively vary the generated magnetic field by varying a temperature of the one or more superconducting magnets. Furthermore, the external anchor assembly may be configurable to selectively diminish the generated magnetic field by increasing the temperature of the one or more superconducting magnets to be equal to or greater than a critical temperature of between about 90 to 100 K. In such a case, the magnetic field may be diminished to zero.

In example embodiments, when the external anchor assembly is magnetically coupled to the internal anchor assembly via the applied magnetic field and the instrument assembly is secured to the internal anchor assembly, the instrument of the instrument assembly is operable to provide an applied force of between about 1 to 5 N.

Example embodiments may further comprise a controller, or the like. The controller may be configurable to configure a magnitude of the magnetic field applied, by the magnetic assembly, at the internal anchor assembly. The controller may be further configurable to configure the temperature control section to control the temperature of the one or more superconducting magnets. The controller may be selectively configurable to perform the configuring and/or selective configuring of any element of the surgical system described above and in the present disclosure. Such selective configuring may be based on, among other things, user/operator instructions, feedback from user/operator instructions and/or actions, measurements and/or readings from one or more sensors and/or elements of the surgical system, historic information (such as measurements, readings, user/operator instructions, feedback from user/operator instructions and/or actions), specific patient information and/or records, pre-programmed and/or defaulted information, etc. The controller may be any device operable to communicate with one or more elements of surgical system, and may include a computing device, communication device, virtual machine, computer, node, instance, host, or machine in a networked computing environment. The controller may comprise logic stored in non-transitory computer readable medium which, when executed by controller and/or a processor of or associated with controller, is operable to perform one or more operations, configuring actions, and/or communications with one or more elements of surgical system, as described in the present disclosure. For example, controller may be operable to communicate with and/or configure one or more of the temperature control section (including the cryo-cooler assembly), support structure, intermediary member, instrument assembly, etc.

It is to be understood in the present disclosure that one or more instrument assemblies and/or internal anchor assemblies may be inserted into and positioned inside the cavity of the body (i.e., patient body), and one or more external anchor assemblies may be configurable to magnetically couple (or magnetically secure) to the one or more internal anchor assemblies (and one or more instrument assemblies). For example, one external anchor assembly may be configurable to magnetically couple (or magnetically secure) to a plurality of internal anchor assemblies (and one or more instrument assemblies). Furthermore, a plurality of external anchor assemblies may be configurable to magnetically couple (or magnetically secure) to an internal anchor assembly (and one or more instrument assemblies).

Although the above described provision of additional anchorage force has been described in the context of a micro robotic manipulator and an external magnet, it will be appreciated that this is merely an exemplary application and the described apparatus and methods can also be applied to any of a variety of other instruments in which anchorage onto a stable platform inside a body cavity is desired.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages. In particular, and unless otherwise stated, the various features and aspects of the described embodiments may be used separately and/or interchangeably in any combination and are not limited to the arrangements described above.

For example, as referred to in the present disclosure, a controller may be any controller, computing device, processor, and/or communication device, and may include a virtual machine, computer, node, instance, host, and/or machine in a networked computing environment. Also as referred to in the present disclosure, a network, cloud, or networked computing environment may be a collection of machines connected by communication channels that facilitate communications between machines and allow for machines to share resources. Network may also refer to a communication medium between processes on the same machine. Also as referred to herein, a network element, node, or server may be a machine deployed to execute a program operating as a socket listener and may include software instances.

Furthermore, as referred to in the present disclosure, terms such as "assembly," "apparatus," "portion," "segment," "member," "body," "section," "subsystem," "system," or other similar and/or equivalent terms should generally be construed broadly to include one part or more than one part or element attached, connected, secured, and/or coupled together.

Various terms used herein have special meanings within the present technical field. Whether a particular term should be construed as such a "term of art" depends on the context in which that term is used. For example, "connect," "connected," "connecting," "connectable," "attach," "attached," "attaching," "attachable," "secure," "secured," "securing,"

"securable," "lock," "locked," "locking," "lockable," "anchor," "anchored," "anchoring," "anchorable," "install," "installed," "installing," "installable," "couple," "coupled," "coupling," "in communication with," "communicating with," "associated with," "associating with," or other similar terms should generally be construed broadly to include situations where attachments, connections, installations, and anchoring are direct between referenced elements or through one or more intermediaries between the referenced elements. As another example, "un-connect," "un-connected," "un-connecting," "un-connectable," "un-attach," "un-attached," "un-attaching," "un-attachable," "un-secure," "un-secured," "un-securing," "un-securable," "unlock," "unlocked," "unlocking," "unlockable," "un-anchor," "un-anchored," "un-anchoring," "un-anchorable," "uninstall," "uninstalled," "uninstalling," "uninstallable," "uncouple," "uncoupled," "uncoupling," or other similar terms should generally be construed broadly to include situations where separation, removal, and detaching are direct between referenced elements or from one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. An external anchor assembly for use with a surgical system, the surgical system having an internal anchor assembly configurable to be inserted into and positioned inside a cavity of a body, the external anchor assembly comprising:
   a magnetic assembly having one or more superconducting magnets configurable to generate a magnetic field and a conductive housing for receiving the one or more superconducting magnets;
   a temperature control section configurable to control a temperature of the one or more superconducting magnets via the conductive housing; and
   an external anchor body configurable to receive the magnetic assembly and the temperature control section, the external anchor body fixably positionable outside of the body;
   wherein the magnetic assembly is configurable to magnetically couple to the internal anchor assembly via the magnetic field.

2. The external anchor assembly of claim 1, wherein the magnetic assembly is configurable to generate the magnetic field with a magnitude of about 0 to 5 Tesla.

3. The external anchor assembly of claim 1, wherein the external anchor assembly is configurable to selectively vary the magnetic field applied at the internal anchor assembly between a magnitude of about 0 to 2 Tesla.

4. The external anchor assembly of claim 3, wherein, when the external anchor assembly magnetically couples to the internal anchor assembly, and when the magnetic assembly is magnetically coupled to the internal anchor assembly at a first separation distance from the internal anchor assembly, the external anchor assembly is configurable to vary the magnitude of the magnetic field applied at the internal anchor assembly by varying the first separation distance.

5. The external anchor assembly of claim 3, wherein
   the external anchor assembly further comprises a support structure, the support structure selectively configurable to fixably position the external anchor body outside of the body,
   the magnetic field applied at the internal anchor assembly is reduced by selectively configuring the support structure to increase the first separation distance, and
   the magnetic field applied at the internal anchor assembly is increased by selectively configuring the support structure to decrease the first separation distance.

6. The external anchor assembly of claim 3, further comprising an intermediary member positionable between the external anchor body and the internal anchor assembly,
   wherein the first separation distance is varied by selectively varying a dimension of the intermediary member.

7. The external anchor assembly of claim 6, wherein the intermediary member is an inflatable bladder.

8. The external anchor assembly of claim 1, wherein the external anchor assembly is configurable to selectively vary the generated magnetic field between a magnitude of about 0 to 5 Tesla.

9. The external anchor assembly of claim 8, wherein the external anchor assembly is configurable to selectively vary the generated magnetic field by varying a temperature of the one or more superconducting magnets.

10. The external anchor assembly of claim 9, wherein the external anchor assembly is configurable to selectively diminish the generated magnetic field by increasing the temperature of the one or more superconducting magnets to be equal to or greater than a critical temperature of between about 90 to 100 K.

11. The external anchor assembly of claim 1, wherein the magnetic assembly comprises a plurality of superconducting magnets configured in one or more vertically stacked arrangements.

12. The external anchor assembly of claim 11, wherein
   each of the superconducting magnets comprise a circular cross-sectional shape with a radius,
   each of the one or more vertically stacked arrangements of superconducting magnets has a collective height, and
   the collective height is equal to or greater than the radius.

13. The external anchor assembly of claim 11, wherein
each of the superconducting magnets comprise a hexagonal cross-sectional shape with a first distance between opposing corners,
each of the one or more vertically stacked arrangements of superconducting magnets has a collective height, and
the collective height is equal to or greater than the first distance between opposing corners.

14. The external anchor assembly of claim 1, wherein the one or more superconducting magnets comprise Ba, Cu, and O.

15. The external anchor assembly of claim 1, wherein
the temperature control section comprises a heat rod and a cryo-cooler,
the heat rod is in contact with the conductive housing and the cryo-cooler,
the cryo-cooler is configurable to control the temperature of the superconducting magnets via the heat rod and the conductive housing,
the external anchor body includes an elongated body comprising a first end and a second end opposite the first end,
the elongated body of the external anchor body is configurable to receive the magnetic assembly at the first end,
the elongated body of the external anchor body is configurable to receive the cryo-cooler at the second end, and
the elongated body of the external anchor body is configurable to receive the heat rod at least between the first end and the second end.

16. The external anchor assembly of claim 1, further comprising an instrument assembly having an instrument at a first end and an instrument assembly attaching section at a second end,
wherein the internal anchor assembly further comprises an internal anchor attaching section, and
wherein the instrument assembly is configurable to secure to the internal anchor assembly by securing the instrument assembly attaching section to the internal anchor attaching section.

17. The external anchor assembly of claim 15, wherein, when the external anchor assembly is magnetically coupled to the internal anchor assembly via the applied magnetic field and the instrument assembly is secured to the internal anchor assembly, the instrument of the instrument assembly is operable to provide an applied force of between about 0 to 5 N.

18. The external anchor assembly of claim 1, further comprising a controller, the controller configurable to:
configure a magnitude of the magnetic field applied, by the magnetic assembly, at the internal anchor assembly; and
configure the temperature control section to control the temperature of the one or more superconducting magnets.

19. A surgical system comprising:
an internal anchor assembly, the internal anchor assembly configurable to be inserted into and positioned inside a cavity of a body; and
an external anchor assembly configurable to magnetically couple to the internal anchor assembly, the external anchor assembly including:
a magnetic assembly having one or more superconducting magnets configurable to generate a magnetic field and a conductive housing for receiving the one or more superconducting magnets;
a temperature control section configurable to control a temperature of the one or more superconducting magnets via the conductive housing; and
an external anchor body configurable to receive the magnetic assembly and the temperature control section, the external anchor body fixably positionable outside of the body.

20. The surgical system of claim 19, wherein the magnetic assembly is configurable to generate the magnetic field with a magnitude of about 0 to 5 Tesla.

21. The surgical system of claim 19, wherein the external anchor assembly is configurable to selectively vary the magnetic field applied at the internal anchor assembly between a magnitude of about 0 to 2 Tesla.

22. The surgical system of claim 21, wherein, when the external anchor assembly magnetically couples to the internal anchor assembly, and when the magnetic assembly is magnetically coupled to the internal anchor assembly at a first separation distance from the internal anchor assembly, the external anchor assembly is configurable to vary the magnitude of the magnetic field applied to the internal anchor assembly by varying the first separation distance.

23. The surgical system of claim 22, wherein
the external anchor assembly further comprises a support structure, the support structure selectively configurable to fixably position the external anchor body outside of the body,
the magnetic field applied at the internal anchor assembly is reduced by selectively configuring the support structure to increase the first separation distance, and
the magnetic field applied at the internal anchor assembly is increased by selectively configuring the support structure to decrease the first separation distance.

24. The surgical system of claim 22, further comprising an intermediary member positionable between the external anchor assembly and the internal anchor assembly,
wherein the first separation distance is varied by selectively varying a dimension of the intermediary member.

25. The surgical system of claim 24, wherein the intermediary member is an inflatable bladder.

26. The surgical system of claim 19, wherein the external anchor assembly is configurable to selectively vary the generated magnetic field between a magnitude of about 0 to 5 Tesla.

27. The surgical system of claim 26, wherein the external anchor assembly is configurable to selectively vary the generated magnetic field by varying a temperature of the one or more superconducting magnets.

28. The surgical system of claim 27, wherein the external anchor assembly is configurable to selectively diminish the generated magnetic field by increasing the temperature of the one or more superconducting magnets to be equal to or greater than a critical temperature of between about 90 to 100 K.

29. The surgical system of claim 19, wherein the magnetic assembly comprises a plurality of superconducting magnets configured in one or more vertically stacked arrangements.

30. The surgical system of claim 29, wherein
each of the superconducting magnets comprise a circular cross-sectional shape with a radius,
each of the one or more vertically stacked arrangements of superconducting magnets has a collective height, and
the collective height is equal to or greater than the radius.

31. The surgical system of claim 29, wherein
each of the superconducting magnets comprise a hexagonal cross-sectional shape with a first distance between opposing corners,
each of the one or more vertically stacked arrangements of superconducting magnets has a collective height, and
the collective height is equal to or greater than the first distance between opposing corners.

32. The surgical system of claim 19, wherein the one or more superconducting magnets comprise Ba, Cu, and O.

33. The surgical system of claim 19, wherein:
the temperature control section comprises a heat rod and a cryo-cooler,
the heat rod is in contact with the conductive housing and the cryo-cooler,
the cryo-cooler is configurable to control the temperature of the superconducting magnets via the heat rod and the conductive housing,
the external anchor body includes an elongated body comprising a first end and a second end opposite the first end,
the elongated body of the external anchor body is configurable to receive the magnetic assembly at the first end,
the elongated body of the external anchor body is configurable to receive the cryo-cooler at the second end, and
the elongated body of the external anchor body is configurable to receive the heat rod at least between the first end and the second end.

34. The surgical system of claim 19, further comprising an instrument assembly having an instrument at a first end and an instrument assembly attaching section at a second end,
wherein the internal anchor assembly further comprises an internal anchor attaching section, and
wherein the instrument assembly is configurable to secure to the internal anchor assembly by securing the instrument assembly attaching section to the internal anchor attaching section.

35. The surgical system of claim 34, wherein, when the external anchor assembly is magnetically coupled to the internal anchor assembly via the applied magnetic field and the instrument assembly is secured to the internal anchor assembly, the instrument of the instrument assembly is operable to provide an applied force of between about 0 to 5 N.

36. The surgical system of claim 19, further comprising a controller, the controller configurable to:
configure a magnitude of the magnetic field applied, by the magnetic assembly, at the internal anchor assembly; and
configure the temperature control section to control the temperature of the one or more superconducting magnets.

* * * * *